United States Patent
Shin et al.

(10) Patent No.: US 12,412,271 B2
(45) Date of Patent: Sep. 9, 2025

(54) METHOD FOR MONITORING THYROID EYE DISEASE CONDITION, AND SYSTEM FOR PERFORMING SAME

(71) Applicant: THYROSCOPE INC., Ulsan (KR)

(72) Inventors: Kyubo Shin, Ulsan (KR); Jongchan Kim, Ulsan (KR); Jaemin Park, Ulsan (KR)

(73) Assignee: THYROSCOPE INC., Ulsan (KR)

( * ) Notice: Subject to any disclaimer, the term of this patent is extended or adjusted under 35 U.S.C. 154(b) by 0 days.

(21) Appl. No.: 19/079,747

(22) Filed: Mar. 14, 2025

(65) Prior Publication Data

US 2025/0209624 A1   Jun. 26, 2025

Related U.S. Application Data

(63) Continuation of application No. 19/049,194, filed on Feb. 10, 2025, which is a continuation-in-part of
(Continued)

(30) Foreign Application Priority Data

Aug. 9, 2022 (KR) .................... 10-2022-0099530

(51) Int. Cl.
*G06T 7/00* (2017.01)
*G06V 10/24* (2022.01)
(Continued)

(52) U.S. Cl.
CPC ............ *G06T 7/0012* (2013.01); *G06V 10/24* (2022.01); *G06V 10/26* (2022.01); *G06V 10/774* (2022.01);
(Continued)

(58) Field of Classification Search
CPC ......... G06T 7/0012; G06T 2207/20081; G06T 2207/20084; G06T 2207/30041;
(Continued)

(56) References Cited

U.S. PATENT DOCUMENTS

2014/0348403 A1   11/2014   Kurtz et al.
2015/0161472 A1*   6/2015   Yoshioka ............. G06V 40/193
                                                                382/197
(Continued)

FOREIGN PATENT DOCUMENTS

| KR | 1020200133923 A | 12/2020 |
| KR | 1020200136950 A | 12/2020 |
| KR | 102379061 B1 | 4/2022 |

OTHER PUBLICATIONS

Huang, Xiao, et al. "An intelligent diagnostic system for thyroid-associated ophthalmopathy based on facial images." Frontiers in Medicine 9 (2022): 920716. (Year: 2022).*
(Continued)

*Primary Examiner* — Van D Huynh
(74) *Attorney, Agent, or Firm* — Dinsmore & Shohl LLP; Yongsok Choi, Esq.

(57) ABSTRACT

A method of monitoring an overall thyroid ophthalmopathy treatment includes requesting a user device to take a facial image and enter a questionnaire survey content according to treatment monitoring cycle; obtaining the facial image and the questionnaire survey content from the user device; obtaining, using the facial image and the questionnaire survey content obtained from the user device, a personalized estimate of the user corresponding to exophthalmos information, CAS (Clinical Activity Score) information, and diplopia information among an indicator proven at an approval stage of the medicine; and displaying, which comprises visualizing the personalized estimate of the user
(Continued)

in a time-series order from the time the user started administering the medicine on the user device.

20 Claims, 33 Drawing Sheets

Related U.S. Application Data application No. PCT/KR2023/011788, filed on Aug. 9, 2023.

(51) Int. Cl.
  *G06V 10/26* (2022.01)
  *G06V 10/774* (2022.01)
  *G06V 10/82* (2022.01)

(52) U.S. Cl.
  CPC .... *G06V 10/82* (2022.01); *G06T 2207/20081* (2013.01); *G06T 2207/20084* (2013.01); *G06T 2207/30041* (2013.01); *G06T 2207/30201* (2013.01); *G06V 2201/03* (2022.01)

(58) Field of Classification Search
  CPC .......... G06T 2207/30201; G06V 10/24; G06V 10/26; G06V 10/774; G06V 10/82; G06V 2201/03
  See application file for complete search history.

(56) References Cited

U.S. PATENT DOCUMENTS

| | | | |
|---|---|---|---|
| 2019/0000349 A1 | 1/2019 | Narayan et al. | |
| 2019/0225696 A1* | 7/2019 | Madden | C07K 16/2863 |
| 2019/0276529 A1* | 9/2019 | Lee | C07K 14/475 |
| 2019/0370959 A1* | 12/2019 | Krishna | G06T 7/60 |
| 2020/0364441 A1* | 11/2020 | O'Sullivan | G06V 40/193 |
| 2021/0027891 A1 | 1/2021 | Rajput et al. | |
| 2021/0085174 A1* | 3/2021 | Kojima | G06T 7/0012 |
| 2022/0301204 A1* | 9/2022 | Ohno | G01B 11/00 |
| 2022/0313077 A1* | 10/2022 | Singh | A61B 3/14 |
| 2023/0005144 A1 | 1/2023 | Shin et al. | |
| 2023/0013792 A1* | 1/2023 | Shin | G06T 7/0014 |
| 2023/0210365 A1* | 7/2023 | Chan | G02B 27/0093 345/8 |
| 2023/0284899 A1* | 9/2023 | Warburton | G06F 3/013 |
| 2024/0343812 A1* | 10/2024 | O'Shaughnessy | C07K 16/2863 |
| 2024/0366144 A1* | 11/2024 | Kwon | A61B 5/7267 |

OTHER PUBLICATIONS

Milbratz GH, Garcia DM, Guimarães FC, Cruz AA. Multiple radial midpupil lid distances: a simple method for lid contour analysis. Ophthalmology. Mar. 2012;119(3):625-8. doi: 10.1016/j.ophtha.2011.08.039. Epub Dec. 22, 2011. PMID: 22197435. (Year: 2011).*

Yolcu, Demet, and Sibel Ozdogan. "A novel method to measure margin reflex distance using the autorefractometer." International Ophthalmology (2022): 1-7. (Year: 2022).*

International Search Report of PCT/KR2023/011788 dated Nov. 20, 2023.

Written Opinion of the International Searching Authority of PCT/KR2023/011788 dated Nov. 20, 2023.

Extended European search report for EP Application No. 25164121.3 issued May 19, 2025.

Sun Yiming et al: "A Fully Automatic Postoperative Appearance Prediction System for Blepharoptosis Surgery with Image-based Deep Learning", Ophthalmology Science, vol. 2, No. 3, Jul. 1, 2022.

* cited by examiner

FIG. 26

| | | | | 2610 |
|---|---|---|---|---|
| personalized estimates | | | | |
| date | exophthalmos degree | CAS | diplopia | |
| August 6 | 14.8 mm | 2 | absent | —2620 |
| October 2 | 15.2 mm | 3 | absent | —2630 |
| difference | +0.4 mm | +1 | - | —2640 |

17. 8. 2024.

5. 11. 2024.

METHOD FOR MONITORING THYROID EYE DISEASE CONDITION, AND SYSTEM FOR PERFORMING SAME

CROSS-REFERENCE TO RELATED APPLICATIONS

This application is a continuation of U.S. patent application Ser. No. 19/049,194 filed Feb. 10, 2025, which is a continuation-in-part of International Application No. PCT/KR2023/011788 filed on Aug. 9, 2023, which claims priority to Korean Patent Application No. 10-2022-0099530 filed on Aug. 9, 2022, the entire contents of which are herein incorporated by reference.

TECHNICAL FIELD

The present disclosure relates to a method for monitoring conditions of thyroid eye disease according to medication administration for alleviating exophthalmos, and a system for performing the same.

BACKGROUND ART

Typical thyroid ophthalmopathy may be caused by hyperthyroidism, but thyroid ophthalmopathy may also be caused by other causes.

Thyroid ophthalmopathy may cause exophthalmos, which may cause cosmetic or physical discomfort to patients.

A common method for treating exophthalmos is physical surgery. In this case, the physical surgery is conducted by using a method in which an eyeball is extracted, a part of a bone inside the eye is removed, and the eyeball is put back in place.

Patients with thyroid ophthalmopathy may alleviate their exophthalmos through physical surgery, but the patients are usually reluctant to undergo the physical surgery on their eyes. Therefore, there are needs to develop a medicine for alleviating thyroid ophthalmopathy by using a drug rather than the physical surgery.

Accordingly, a clinical trial for a medicine for the purpose of treating thyroid ophthalmopathy has been conducted, and recently, the US Food and Drug Administration (FDA) has granted first approval to the medicine for the purpose of treating thyroid ophthalmopathy. Specifically, the FDA has granted the first approval to Horizon Therapeutics' TEPEZZA.

Meanwhile, in the case of the medicine for the purpose of treating thyroid ophthalmopathy, this medicine costs a lot and cyclical administration is required a plurality of times over a predetermined period of time rather than a single administration. Therefore, for patients receiving treatment, they are interested in how their conditions such as exophthalmos change according to medicine administration.

However, a patient's own exophthalmos condition may only be measured by medical staff when the patient visits a hospital for the medicine administration, so there is a limitation that the patient may check only limited condition information provided.

Accordingly, a method for monitoring a drug efficacy process according to the administration of a medicine for the purpose of treating thyroid ophthalmopathy without visiting a hospital is needed.

SUMMARY

Technical Problem

In a problem to be solved by the content disclosed by the present application, an objective of the present disclosure for solving the problem is to provide a method for monitoring thyroid ophthalmopathy treatment, the method obtaining, sequentially arranging, and displaying a patient's personalized estimates corresponding to exophthalmos degree information, CAS information, and diplopia information, which are proven through the effectiveness of medicine during the patient is administered a medicine for the purpose of treating thyroid ophthalmopathy.

In the problem to be solved by the content disclosed by the present application, another objective of the present disclosure for solving the problem is to provide a method for monitoring thyroid ophthalmopathy treatment, the method comparing a patient's personalized estimate corresponding to exophthalmos degrees with an exophthalmos degree at a time point at which the medicine administration period has ended, so as to suggest a hospital visit to the patient after the administration period of a medicine for the purpose of treating the patient's thyroid ophthalmopathy has ended.

In the problem to be solved by the content disclosed by the present application, a yet another objective of the present disclosure for solving the problem is to provide a method for monitoring the effectiveness of medicine, the method obtaining facial images at two time points different from each other while a patient is administered a medicine for the purpose of treating thyroid ophthalmopathy, so as to determine a trend of changes in exophthalmos degrees between the two time points on the basis of a comparison of the facial images, thereby determining whether the medicine is effective or not.

The problem to be solved in the present application is not limited to the above-mentioned problem, and the problems not mentioned will be clearly understood by those skilled in the art, to which the technology disclosed by the present application belongs, from accompanying drawings.

Technical Solution

According to an exemplary embodiment of the present disclosure, a method of monitoring an overall thyroid ophthalmopathy treatment, the method comprising: during a treatment period in which a user is prescribed and administered a medicine that has been proven to be effective in treating thyroid ophthalmopathy treatment through clinical trials, requesting a user device to take a facial image and enter a questionnaire survey content according to treatment monitoring cycle; obtaining the facial image and the questionnaire survey content from the user device; obtaining, using the facial image and the questionnaire survey content obtained from the user device, a personalized estimate of the user corresponding to exophthalmos information, CAS (Clinical Activity Score) information, and diplopia information among an indicator proven at an approval stage of the medicine; and displaying, which comprises visualizing the personalized estimate of the user in a time-series order from the time the user started administering the medicine on the user device; after the treatment period is ended, requesting the user device to take the facial image according to a post-treatment monitoring cycle; obtaining the facial image from the user device; obtaining the personalized estimate of the user corresponding to at least the exophthalmos information by using the facial image obtained from the user device; displaying, which comprises visualizing the personalized estimate of the user corresponding to the exophthalmos information by comparing with the exophthalmos information at the end of the administration of the medicine on the user device; and displaying a message about a suggestion to visit a hospital based on a difference between the personalized estimate of the user corresponding to the exophthalmos information and the exophthalmos information at the end of the administration of the medicine.

According to an exemplary embodiment of the present disclosure, the post-treatment monitoring cycle is different from the cycle of monitoring treatment.

According to an exemplary embodiment of the present disclosure, the treatment monitoring cycle and the post-treatment monitoring cycle is determined by the medicine.

According to an exemplary embodiment of the present disclosure, the treatment monitoring cycle is determined by considering an administration cycle of the medicine, the post-treatment monitoring cycle is determined by considering time of symptom recurrence after the administration of the medicine has ended.

According to an exemplary embodiment of the present disclosure, the questionnaire survey content comprises a question related to side effects based on a result of the clinical trials, determining whether a side effect occurs by using the questionnaire survey content obtained from the user device during the treatment period.

According to an exemplary embodiment of the present disclosure, during the treatment period, if the user experiences side effects, displaying a message on the user device suggesting at least one of a telephone call to the hospital and access to the hospital's internet site.

According to an exemplary embodiment of the present disclosure, during the treatment period, displaying comparative data obtained based on a result of the clinical trials on the user device in correspondence with an acquisition date of the personalized estimate of the user.

According to an exemplary embodiment of the present disclosure, the comparative data is obtained by adjusting standard data included in the result of the clinical trials according to the personalized estimate.

According to an exemplary embodiment of the present disclosure, the personalized estimate of the user corresponding to the exophthalmos information comprises a numerical value about exophthalmos, the personalized estimate of the user corresponding to CAS information comprises a numerical value about CAS, the personalized estimate of the user corresponding to diplopia information comprises a grade about diplopia, wherein visualizing and displaying the personalized estimate of the user in a time-series order from the time the user started administering the medicine comprises displaying the numerical value about exophthalmos, the numerical value about CAS and the grade about diplopia in at least one of a time-series order data table and a time-series order data graph on the user device.

According to an exemplary embodiment of the present disclosure, wherein displaying a message about a suggestion to visit a hospital based on a difference between the personalized estimate of the user corresponding to the exophthalmos information and the exophthalmos information at the administration end time of the medicine comprises, determining whether a difference between the personalized estimate of the user corresponding to the exophthalmos information and an exophthalmos numerical value included in the exophthalmos information at the administration end time of the medicine is greater than 2 mm; and if the difference in the exophthalmos numerical value is equal to or greater than 2 mm, displaying a message about a suggestion to visit a hospital on the user device.

According to an exemplary embodiment of the present disclosure, after the treatment period has ended, obtaining by requesting input of the questionnaire survey content to the user device according to the post-treatment monitoring cycle; by using the facial image and the questionnaire survey content obtained from the user device, obtaining the personalized estimate of the user corresponding to the CAS information; determining whether the personalized estimate of the user corresponding to the CAS information is equal to or greater than 3; and if the personalized estimate of the user corresponding to the CAS information is equal to or greater than 3, displaying the message about the suggestion to visit the hospital to the user device.

According to an exemplary embodiment of the present disclosure, obtaining a personalized estimate of the user corresponding to exophthalmos information, CAS (Clinical Activity Score) information, and diplopia information using the facial image and the questionnaire survey content obtained from the user device, comprising: obtaining the personalized estimate of the user corresponding to the exophthalmos information by using the facial image; obtaining the personalized estimate of the user corresponding to the CAS information by using the facial image; and obtaining the personalized estimate of the user corresponding to the diplopia information by using the facial image.

According to an exemplary embodiment of the present disclosure, obtaining an actual measurement of the numerical value about exophthalmos for the user and a facial image corresponding to an actual measurement of the numerical value about exophthalmos, wherein the personalized estimate of the user corresponding to the exophthalmos information is obtained by using the facial image obtained from the user device, the facial image corresponding to an actual measurement of the numerical value about exophthalmos and the actual measurement of exophthalmos.

According to an exemplary embodiment of the present disclosure, wherein obtaining the facial image and the questionnaire survey content from the user device during the treatment period, comprising: providing a photographing guide to the user device; taking a facial image if the photographing guide is satisfied; displaying the questionnaire survey content to the user device; and obtaining a result of a questionnaire survey; wherein obtaining a facial image from the user device after the treatment period has ended, comprising: providing the photographing guide to the user device; and taking a facial image if the photographing guide is satisfied.

According to an exemplary embodiment of the present disclosure, wherein the photographing guide is a guide to guide at least one of a left and right angles of a face, an up and down angles of the face, an expression of the face and a position of eyes in an image.

According to an exemplary embodiment of the present disclosure, wherein the photographing guide comprises an indicator of whether the left and right angles of the face, the up and down angles of the face, the expression of the face, and the position of the eyes in the image are each satisfied, wherein taking a facial image if the photographing guide is satisfied comprises, determining whether the photographing guide is satisfied according to whether the left and right angles of the face, the up and down angles of the face, and the position of the eyes on the image satisfy criteria; when the photographing guide is satisfied, changing a display status of the indicator that indicates whether the left and right angles of the face, the up and down angles of the face, the expression of the face, and the position of the eyes in the image are satisfied; and taking the facial image if the photographing guide is satisfied.

According to an exemplary embodiment of the present disclosure, wherein the user visits a hospital to be administered the medicine, wherein the method of monitoring an overall treatment of thyroid ophthalmopathy treatment comprises, obtaining thyroid dysfunction management history for the user; and providing thyroid dysfunction management history to a medical staff device when the user visits the hospital.

According to an exemplary embodiment of the present disclosure, a non-transitory computer-readable recording medium storing a computer program for executing the method of monitoring an overall thyroid ophthalmopathy treatment.

According to the exemplary embodiment of the present disclosure, A method for determining a therapeutic effect of a medicine, the method comprising: while a user is prescribed and administered a medicine that has been proven to be effective in treating thyroid ophthalmopathy treatment through clinical trials, obtaining a first image representing the user's eyes captured according to a photographing guide at a first time; obtaining a first exophthalmos-related variable based on the first image; obtaining a second image representing the user's eyes captured according to a photographing guide at a second time later than the first time; obtaining a second exophthalmos-related variable based on the second image; determining a trend regarding the exophthalmos of the user by comparing the first exophthalmos-related variable and the second exophthalmos-related variable, wherein the trend is classified as increasing, decreasing or unchanged; and determining whether the medicine is effective based on the trend regarding the exophthalmos.

According to the exemplary embodiment of the present disclosure, wherein the exophthalmos-related variable comprises at least one of Radial MPLD values, a horizontal length of an eye and a 3D facial landmark coordinate value.

According to the exemplary embodiment of the present disclosure, wherein the exophthalmos-related variable is not the numerical value of exophthalmos.

According to the exemplary embodiment of the present disclosure, wherein determining whether the medicine is effective further comprises displaying a message on the user device suggesting a visit if the trend regarding the exophthalmos is an increasing trend.

The problem solutions of the present disclosure are not limited to the above-described solutions, and solutions that are not mentioned may be clearly understood to those skilled in the art, to which the present disclosure belongs, from the present specification and the accompanying drawings.

Advantageous Effects

According to the exemplary embodiment disclosed herein, there is provided a method for monitoring the effectiveness of medicine, the method including: obtaining and displaying, as time-series data, a patient's personalized estimates corresponding to exophthalmos degree information, CAS information, and diplopia information while the patient is administered a medicine for the purpose of treating thyroid ophthalmopathy; and comparing the patient's personalized estimate corresponding to exophthalmos degrees with an exophthalmos degree at an end time point of the medicine administration, thereby suggesting a hospital visit to the patient after the medicine administration has ended.

In the problem to be solved by the content disclosed by the present application, there may be provided a method for determining whether a medicine is effective or not, the method including: obtaining facial images at two time points different from each other during a patient is administered a medicine for the purpose of treating thyroid ophthalmopathy; and determining a trend in exophthalmos degrees between the two time points on the basis of a comparison of the facial images obtained, thereby determining whether the medicine is effective or not according to whether the trend is increasing, decreasing, or unchanged without determining the exact numerical values of the exophthalmos degrees.

The effects of the present disclosure are not limited to the above-described effects, and effects not mentioned herein may be clearly understood by those skilled in the art, to which the present disclosure belongs, from the present specification and accompanying drawings.

DESCRIPTION OF DRAWINGS

FIG. 26 is a view illustrating a UI for displaying a patient's personalized estimates according to the exemplary embodiment.

DETAILED DESCRIPTION

Figure 1:
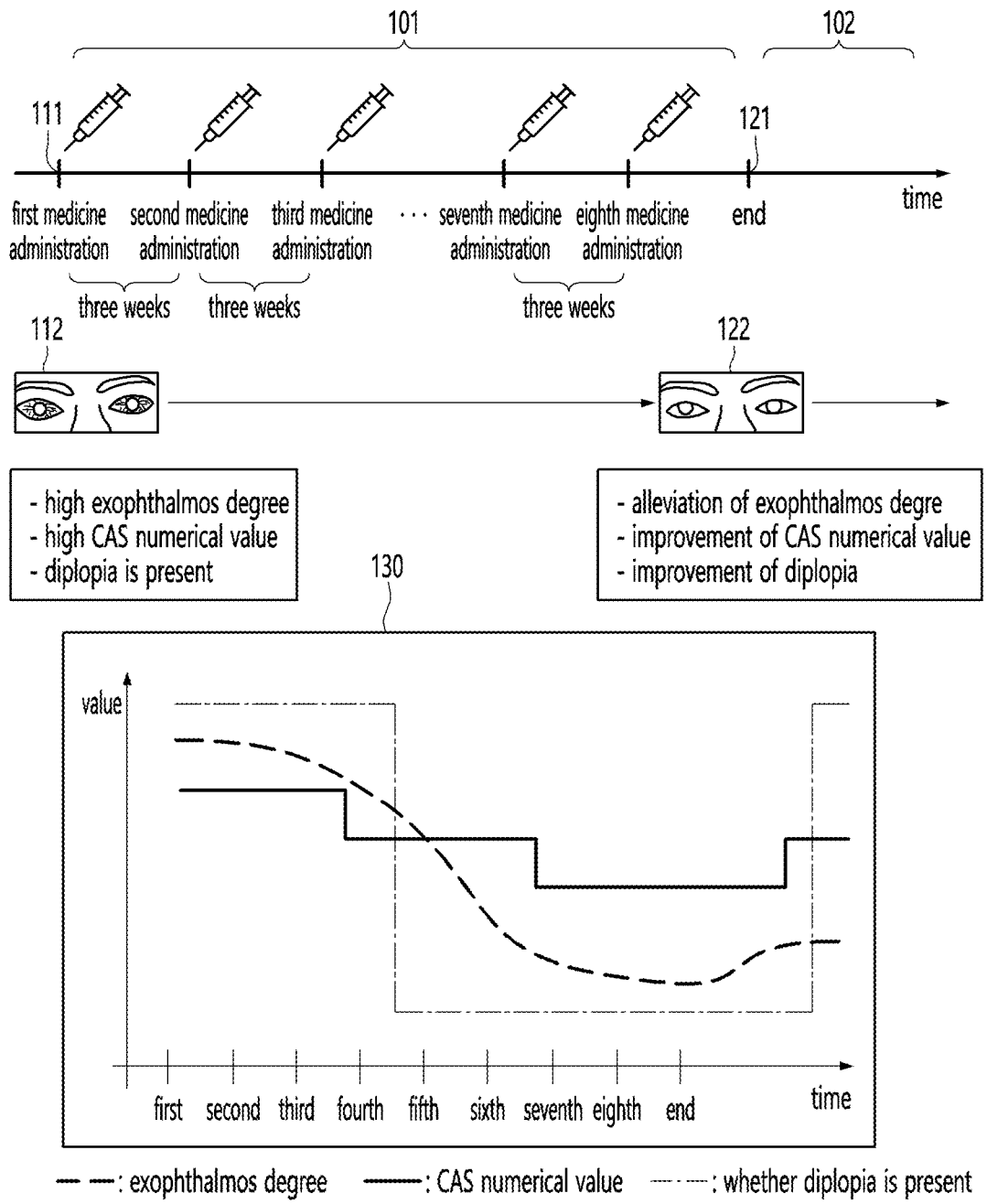
FIG. 1 is a view illustrating a method for monitoring overall thyroid ophthalmopathy treatment according to an exemplary embodiment.

Exemplary embodiments described in the present specification are intended to clearly describe the idea of the present disclosure to those skilled in the art. Therefore, the present disclosure is not limited by the exemplary embodiments, and the scope of the present disclosure should be interpreted as encompassing modifications and variations without departing from the idea of the present disclosure.

Terms used in the present specification are selected from among general terms, which are currently widely used, in consideration of functions in the present disclosure and may have meanings varying depending on intentions of those skilled in the art, customs in the field of art, the emergence of new technologies, or the like. However, in contrast, in a case where a specific term is defined and used with an arbitrary meaning, the meaning of the term will be described separately. Accordingly, the terms used in the present specification should be interpreted on the basis of the actual meanings and the whole context throughout the present specification rather than based on just names for the terms.

Numbers (e.g., first, second, etc.) used in a process of describing the present specification are merely identification symbols for distinguishing one element and/or component from other elements and/or components.

In the exemplary embodiments below, the singular forms are intended to include the plural forms as well, unless the context clearly indicates otherwise.

In the following exemplary embodiments, terms such as "comprise", "include", or "have" mean that a feature or a component described in the specification exists, and the possibility that one or more other features or components may be added is not precluded.

The accompanying drawings of the present specification are intended to easily describe the present disclosure, and shapes shown in the drawings may be exaggerated as necessary in order to facilitate in understanding the present disclosure. Therefore, the present disclosure is not limited by the drawings.

Where certain exemplary embodiments are otherwise implementable, a specific process order may also be performed different from the described order. For example, two processes described in succession may be performed substantially and simultaneously, or may be performed in an order opposite to the described order.

When it is determined that detailed descriptions of well-known components or functions related to the present disclosure may obscure the subject matter of the present disclosure, detailed descriptions thereof may be omitted herein as necessary.

According to an exemplary embodiment of the present disclosure, a method of monitoring an overall thyroid ophthalmopathy treatment, the method comprising: during a treatment period in which a user is prescribed and administered a medicine that has been proven to be effective in treating thyroid ophthalmopathy treatment through clinical trials, requesting a user device to take a facial image and enter a questionnaire survey content according to treatment monitoring cycle; obtaining the facial image and the questionnaire survey content from the user device; obtaining, using the facial image and the questionnaire survey content obtained from the user device, a personalized estimate of the user corresponding to exophthalmos information, CAS (Clinical Activity Score) information, and diplopia information among an indicator proven at an approval stage of the medicine; and displaying, which comprises visualizing the personalized estimate of the user in a time-series order from the time the user started administering the medicine on the user device; after the treatment period is ended, requesting the user device to take the facial image according to a post-treatment monitoring cycle; obtaining the facial image from the user device; obtaining the personalized estimate of the user corresponding to at least the exophthalmos information by using the facial image obtained from the user device; displaying, which comprises visualizing the personalized estimate of the user corresponding to the exophthalmos information by comparing with the exophthalmos information at the end of the administration of the medicine on the user device; and displaying a message about a suggestion to visit a hospital based on a difference between the personalized estimate of the user corresponding to the exophthalmos information and the exophthalmos information at the end of the administration of the medicine.

According to an exemplary embodiment of the present disclosure, the post-treatment monitoring cycle is different from the cycle of monitoring treatment.

According to an exemplary embodiment of the present disclosure, the treatment monitoring cycle and the post-treatment monitoring cycle is determined by the medicine.

According to an exemplary embodiment of the present disclosure, the treatment monitoring cycle is determined by considering an administration cycle of the medicine, the post-treatment monitoring cycle is determined by considering time of symptom recurrence after the administration of the medicine has ended.

According to an exemplary embodiment of the present disclosure, the questionnaire survey content comprises a question related to side effects based on a result of the clinical trials, determining whether a side effect occurs by using the questionnaire survey content obtained from the user device during the treatment period.

According to an exemplary embodiment of the present disclosure, during the treatment period, if the user experiences side effects, displaying a message on the user device suggesting at least one of a telephone call to the hospital and access to the hospital's internet site.

According to an exemplary embodiment of the present disclosure, during the treatment period, displaying comparative data obtained based on a result of the clinical trials on the user device in correspondence with an acquisition date of the personalized estimate of the user.

According to an exemplary embodiment of the present disclosure, the comparative data is obtained by adjusting standard data included in the result of the clinical trials according to the personalized estimate.

According to an exemplary embodiment of the present disclosure, the personalized estimate of the user corresponding to the exophthalmos information comprises a numerical value about exophthalmos, the personalized estimate of the user corresponding to CAS information comprises a numerical value about CAS, the personalized estimate of the user corresponding to diplopia information comprises a grade about diplopia, wherein visualizing and displaying the personalized estimate of the user in a time-series order from the time the user started administering the medicine comprises displaying the numerical value about exophthalmos, the numerical value about CAS and the grade about diplopia in at least one of a time-series order data table and a time-series order data graph on the user device.

According to an exemplary embodiment of the present disclosure, wherein displaying a message about a suggestion to visit a hospital based on a difference between the personalized estimate of the user corresponding to the exophthalmos information and the exophthalmos information at the administration end time of the medicine comprises, determining whether a difference between the personalized estimate of the user corresponding to the exophthalmos information and an exophthalmos numerical value included in the exophthalmos information at the administration end time of the medicine is greater than 2 mm; and if the difference in the exophthalmos numerical value is equal to or greater than 2 mm, displaying a message about a suggestion to visit a hospital on the user device.

According to an exemplary embodiment of the present disclosure, after the treatment period has ended, obtaining by requesting input of the questionnaire survey content to the user device according to the post-treatment monitoring cycle; by using the facial image and the questionnaire survey content obtained from the user device, obtaining the personalized estimate of the user corresponding to the CAS information; determining whether the personalized estimate of the user corresponding to the CAS information is equal to or greater than 3; and if the personalized estimate of the user corresponding to the CAS information is equal to or greater than 3, displaying the message about the suggestion to visit the hospital to the user device.

According to an exemplary embodiment of the present disclosure, obtaining a personalized estimate of the user corresponding to exophthalmos information, CAS (Clinical Activity Score) information, and diplopia information using the facial image and the questionnaire survey content obtained from the user device, comprising: obtaining the personalized estimate of the user corresponding to the exophthalmos information by using the facial image; obtaining the personalized estimate of the user corresponding to the CAS information by using the facial image; and obtaining the personalized estimate of the user corresponding to the diplopia information by using the facial image.

According to an exemplary embodiment of the present disclosure, obtaining an actual measurement of the numerical value about exophthalmos for the user and a facial image corresponding to an actual measurement of the numerical value about exophthalmos, wherein the personalized estimate of the user corresponding to the exophthalmos information is obtained by using the facial image obtained from the user device, the facial image corresponding to an actual measurement of the numerical value about exophthalmos and the actual measurement of exophthalmos.

According to an exemplary embodiment of the present disclosure, wherein obtaining the facial image and the questionnaire survey content from the user device during the treatment period, comprising: providing a photographing guide to the user device; taking a facial image if the photographing guide is satisfied; displaying the questionnaire survey content to the user device; and obtaining a result of a questionnaire survey; wherein obtaining a facial image from the user device after the treatment period has ended, comprising: providing the photographing guide to the user device; and taking a facial image if the photographing guide is satisfied.

According to an exemplary embodiment of the present disclosure, wherein the photographing guide is a guide to guide at least one of a left and right angles of a face, an up and down angles of the face, an expression of the face and a position of eyes in an image.

According to an exemplary embodiment of the present disclosure, wherein the photographing guide comprises an indicator of whether the left and right angles of the face, the up and down angles of the face, the expression of the face, and the position of the eyes in the image are each satisfied, wherein taking a facial image if the photographing guide is satisfied comprises, determining whether the photographing guide is satisfied according to whether the left and right angles of the face, the up and down angles of the face, and the position of the eyes on the image satisfy criteria; when the photographing guide is satisfied, changing a display status of the indicator that indicates whether the left and right angles of the face, the up and down angles of the face, the expression of the face, and the position of the eyes in the image are satisfied; and taking the facial image if the photographing guide is satisfied.

According to an exemplary embodiment of the present disclosure, wherein the user visits a hospital to be administered the medicine, wherein the method of monitoring an overall treatment of thyroid ophthalmopathy treatment comprises, obtaining thyroid dysfunction management history for the user; and providing thyroid dysfunction management history to a medical staff device when the user visits the hospital.

According to an exemplary embodiment of the present disclosure, a non-transitory computer-readable recording medium storing a computer program for executing the method of monitoring an overall thyroid ophthalmopathy treatment.

According to the exemplary embodiment of the present disclosure, A method for determining a therapeutic effect of a medicine, the method comprising: while a user is prescribed and administered a medicine that has been proven to be effective in treating thyroid ophthalmopathy treatment through clinical trials, obtaining a first image representing the user's eyes captured according to a photographing guide at a first time; obtaining a first exophthalmos-related variable based on the first image; obtaining a second image representing the user's eyes captured according to a photographing guide at a second time later than the first time; obtaining a second exophthalmos-related variable based on the second image; determining a trend regarding the exophthalmos of the user by comparing the first exophthalmos-related variable and the second exophthalmos-related variable, wherein the trend is classified as increasing, decreasing or unchanged; and determining whether the medicine is effective based on the trend regarding the exophthalmos.

According to the exemplary embodiment of the present disclosure, wherein the exophthalmos-related variable comprises at least one of Radial MPLD values, a horizontal length of an eye and a 3D facial landmark coordinate value.

According to the exemplary embodiment of the present disclosure, wherein the exophthalmos-related variable is not the numerical value of exophthalmos.

According to the exemplary embodiment of the present disclosure, wherein determining whether the medicine is effective further comprises displaying a message on the user device suggesting a visit if the trend regarding the exophthalmos is an increasing trend.

Hereinafter, a monitoring method and a monitoring system according to the exemplary embodiment are described.

1. Medicine Effectiveness Monitoring

FIG. 1 is a view illustrating a method for monitoring overall thyroid ophthalmopathy treatment according to the exemplary embodiment.

Referring to FIG. 1, based on the method for monitoring the overall thyroid ophthalmopathy treatment according to the exemplary embodiment, a patient and/or medical staff may monitor the condition of a patient following administration of a medicine for the purpose of treating thyroid ophthalmopathy.

The medicine for the purpose of treating thyroid ophthalmopathy may be a medicine that has been proven to be effective through a clinical trial in alleviating exophthalmos, reducing a Clinical Activity Score (CAS) numerical value, and improving diplopia in a patient who is administered the medicine. That is, the medicine may mean a medicine that is sold and prescribed after undergoing the clinical trial.

The condition of the patient may include an exophthalmos degree, a CAS numerical value, and whether the patient has diplopia, but it is not limited thereto. The patient's condition may include the condition of the patient in relation to the improved effectiveness of medicine submitted at the time of approval for the medicine.

Referring to FIG. 1, according to the method for monitoring the medicine effectiveness according to the exemplary embodiment, a patient's condition may be monitored during a treatment period 101 in which a medicine is administered and during a post-treatment period 102 after the medicine administration is ended.

Referring to FIG. 1, the medicine is illustrated as being administered a total of eight times at three-week intervals, but a medication administration regimen is not limited thereto.

Referring to FIG. 1, a patient at a time point 111 of first administration of a medicine may be in a condition 112 of having symptoms of thyroid ophthalmopathy. In this case, the patient may have a high exophthalmos degree, a high CAS numerical value, and diplopia.

Referring to FIG. 1, at an end time point 121 of administering a medicine, the patient may be in a condition 122 where the symptoms of thyroid ophthalmopathy have been completely cured. In this case, the patient may have the condition of the alleviated exophthalmos degree, improved CAS numerical value, and improved diplopia.

The patient visits a hospital every three-week intervals in order to be administered a medicine, and at each time point of visiting the hospital, medical staff may measure an exophthalmos degree and evaluate a CAS numerical value.

That is, in a case of general patient monitoring, only data on a patient's condition measured by medical staff at a time when the patient visits a hospital may be obtained, and data on the patient's condition during a period when the patient does not visit the hospital is unable to be obtained.

However, the patient's condition is required to be confirmed between hospital visits and after the medicine administration has ended.

More specifically, since thyroid ophthalmopathy is an externally visible symptom, a patient is sensitive to changes in his or her condition and has a need to check in real time whether a medicine is effective or not and the degree of medicine effectiveness according to the medicine administration.

In addition, the medical staff has a need to check how the patient's condition has changed in between the patient's hospital visits because an interval between the hospital visits is long.

According to the method for monitoring the medicine effectiveness according to the exemplary embodiment, even at a time point at which the patient does not visit the hospital, the patient's condition may be monitored, and information related to the medicine effectiveness (such as the exophthalmos degree, CAS numerical value, and whether the patient has diplopia) may be obtained. Specific details regarding the method for monitoring the patient's condition are described below.

Referring to a graph 130 in FIG. 1, patient condition data may be obtained even for a time point at which a patient does not visit a hospital, so that consecutive data on the patient's condition may be obtained even when hospital visit time points are spaced at three-week intervals, which are long time intervals. In this case, the patient condition data may include exophthalmos degree information, CAS information, and/or diplopia information about the patient. This is not limited thereto, and the patient condition data may include information on eyelid retraction, information on thyroid ophthalmopathy severity, and/or information on side effects, which are information for the patient, and the specific details of each of which are described below.

The patient and/or medical staff may check the patient condition data in real time, and required actions and the like may be taken depending on the patient's condition.

In addition, referring to the graph 130 in FIG. 1, it may be confirmed how the patient's condition changes even when the patient does not visit the hospital during a period 102 after the medicine administration has ended.

Accordingly, as shown in the graph 130, even in a case where the patient's condition is worsened again (e.g., an exophthalmos degree increases, a CAS numerical value increases, or diplopia occurs) during the period 102 after the medicine administration has ended, the patient's condition may be monitored, so that the required actions and the like may be taken according to the patient's condition even during periods when the patient does not visit the hospital periodically due to the end of treatment for the patient.

For example, depending on the patient's condition, an action may be taken such as guiding the patient to visit the hospital, and alerting the medical staff to the patient's condition.

Hereinafter, determination indicators related to thyroid ophthalmopathy are described.

With regard to thyroid ophthalmopathy, there may be two determination indicators: thyroid ophthalmopathy activity and thyroid ophthalmopathy severity.

2. Thyroid Ophthalmopathy Activity

Thyroid ophthalmopathy has no clear warning symptoms, making early diagnosis difficult.

Therefore, the medical world has been making efforts to enable early diagnosing thyroid ophthalmopathy through a method for evaluating Clinical Activity Score (CAS), which has been proposed since 1989.

Thyroid ophthalmopathy activity may be determined by a clinical activity score, which may be calculated by considering seven items.

Figure 2:
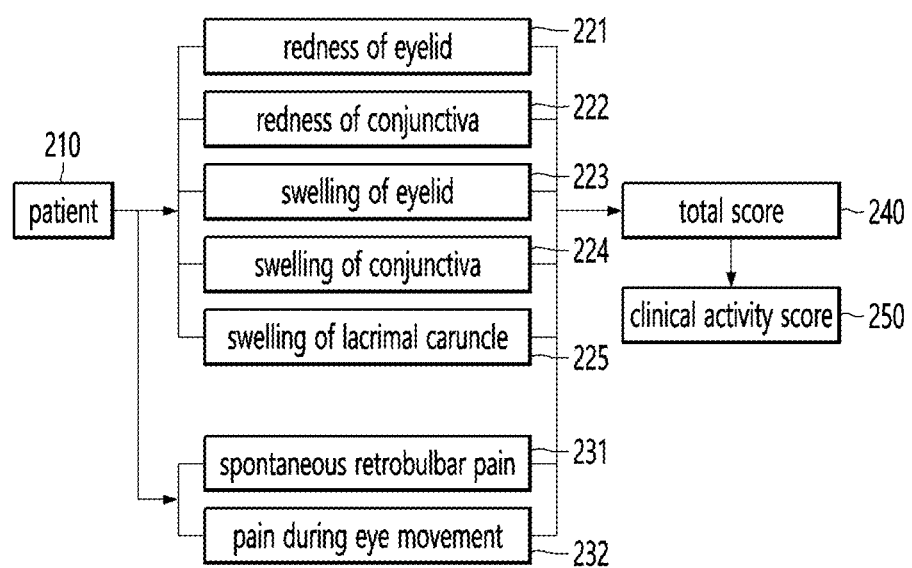
FIG. 2 is a view illustrating a method for determining a clinical activity score for thyroid ophthalmopathy activity.

FIG. 2 is a view illustrating a method for determining a clinical activity score for thyroid ophthalmopathy activity.

Referring to FIG. 2, a total of seven items may be considered for a clinical activity score 250. The total seven items considered include: (1) Redness of eyelid 221, (2) Redness of conjunctiva 222, (3) Swelling of eyelid 223, (4) Swelling of conjunctiva 224, (5) Swelling of lacrimal caruncle 225, (6) Spontaneous retrobulbar pain 231, and (7) Pain on attempted upward or downward gaze 232.

Among these items, five symptoms, namely the redness of eyelid 221, redness of conjunctiva 222, swelling of eyelid 223, swelling of conjunctiva 224, and swelling of lacrimal caruncle 225, may be determined from the eyes of a patient 210. Specifically, the five symptoms of redness of eyelid 221, redness of conjunctiva 222, swelling of eyelid 223, swelling of conjunctiva 224, and swelling of lacrimal caruncle 225 may be determined from the actual eyes of the patient 210 or from an eye image of the patient 210.

The two symptoms of spontaneous retrobulbar pain 231 and pain on attempted upward or downward gaze 232 may be determined by conducting a questionnaire survey on the patient 210.

Depending on the presence or absence of symptoms of each of the seven items, a score is calculated for each symptom, with 1 point for the presence of symptoms and 0 points for the absence of symptoms, so that a total score 240 may be calculated by adding up the calculated scores. The maximum score for a clinical activity score 250 is seven points, and in a case where the total score 240 is greater than or equal to three points, it may be determined that thyroid ophthalmopathy activity is present.

The presence or absence of five symptoms 221, 222, 223, 224, and 225 that may be determined from the eyes of the patient 210 may be determined by medical staff evaluating the symptoms by examining the patient's eyes. Alternatively, the presence or absence of the five symptoms 221, 222, 223, 224, and 225 that may be determined from the eyes of the patient 210 may be determined by evaluating the presence or absence of the symptoms on the basis of an image that is captured of a face or eye of the patient 210.

Meanwhile, the five symptoms 221, 222, 223, 224, and 225 that may be determined from the eyes of the patient 210 may also be determined by using a trained prediction model.

Specifically, the presence or absence of each of the five symptoms may be predicted from the patient's facial image by using a model for predicting redness of eyelid from the facial image, a model for predicting redness of conjunctiva from the facial image, a model for predicting swelling of eyelid from the facial image, a model for predicting swelling of conjunctiva from the facial image, and a model for predicting swelling of lacrimal caruncle from the facial image.

This is not limited thereto, and the presence or absence of each of the five symptoms may also be predicted from the patient's facial image by using a single prediction model that predicts all the redness of eyelid, the redness of conjunctiva, the swelling of eyelid, the swelling of conjunctiva, and the swelling of lacrimal caruncle.

3. Thyroid Ophthalmopathy Severity

Thyroid ophthalmopathy severity is an indicator for classifying and indicating the level of thyroid ophthalmopathy in a patient, and there may be various classification criteria.

For example, thyroid ophthalmopathy severities may be classified on the basis of the European Group on Graves Orbitopathy (EUGOGO).

Figure 3:
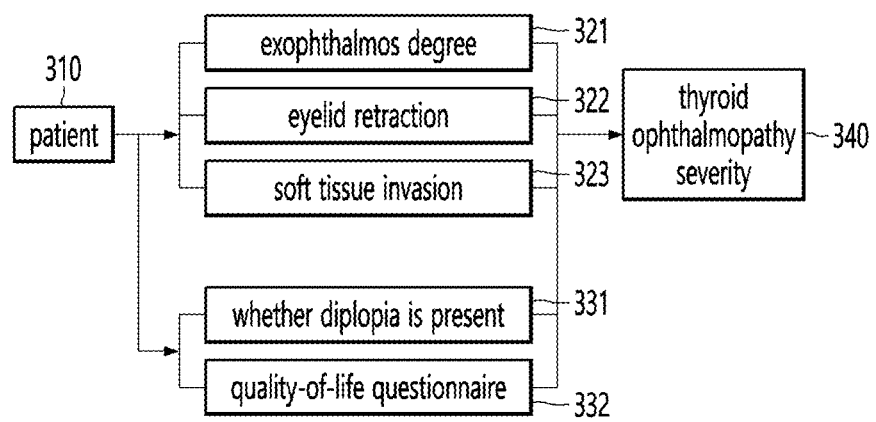
FIG. 3 is a view illustrating a method for determining thyroid ophthalmopathy severity on the basis of European Group on Graves Orbitopathy (EUGOGO) criteria.

FIG. 3 is a view illustrating a method for determining thyroid ophthalmopathy severity on the basis of EUGOGO criteria.

Referring to FIG. 3, a thyroid ophthalmopathy severity 340 may be determined on the basis of determinations including: whether or not an exophthalmos degree 321 is greater than or equal to 3 mm higher than that of the normal condition for race and gender; whether or not eyelid retraction 322 has increased by 2 mm or more; whether or not a rating for soft tissue invasion 323 has increased; whether or not diplopia 331 is present or not; and/or a score according to the content of quality-of-life questionnaire 332 (i.e., a Graves' Orbitopathy Quality of Life (Go-QoL) Questionnaire).

In this case, the thyroid ophthalmopathy severity 340 may be divided into none, mild (moderate), or severe (serious).

The exophthalmos degree 321, eyelid retraction 322, and soft tissue invasion 323 may be determined on the basis of the eyes of the patient 310, and whether diplopia 331 is present or not, and the quality-of-life questionnaire 332 may be determined by conducting a questionnaire survey on the patient 310.

Specifically, the exophthalmos degree 321 may be measured by using an exophthalmometer. Meanwhile, the exophthalmos degree may be determined or estimated by using a facial image, and the details thereof are described later.

The eyelid retraction 322 may be determined or estimated by using a facial image, and the specific details thereof are described later in 7. Facial image-based eyelid retraction determination method.

The soft tissue invasion 323 may be determined by considering whether a rating of one of the four symptoms has increased or not. The four symptoms may include symptoms of swelling of eyelid, redness of eyelid, redness of conjunctiva, and swelling of conjunctiva.

The ratings for the swelling of eyelid, redness of eyelid, redness of conjunctiva, and swelling of conjunctiva which are included in the four symptoms may be determined from the eyes of the patient 310. Specifically, the four symptoms may be determined from the actual eyes of the patient 310 or from an eye image of the patient 310.

A prediction model trained to predict a rating for each of the four symptoms may be used in order to determine the rating for each of the four symptoms from the eye image of the patient 310.

Whether diplopia 331 is present or not may be determined by using Gorman criteria.

According to the Gorman criteria, diplopia may be determined as a grade for one of no diplopia, intermittent diplopia, diplopia at extreme gaze, and persistent diplopia.

Meanwhile, the thyroid ophthalmopathy severities may also be classified on the basis of NOSPECS and/or VISA.

Hereinafter, treatment process monitoring that may be performed during a medicine administration process is described.

4. Treatment Process Monitoring (1) General Monitoring Method

Figure 4:
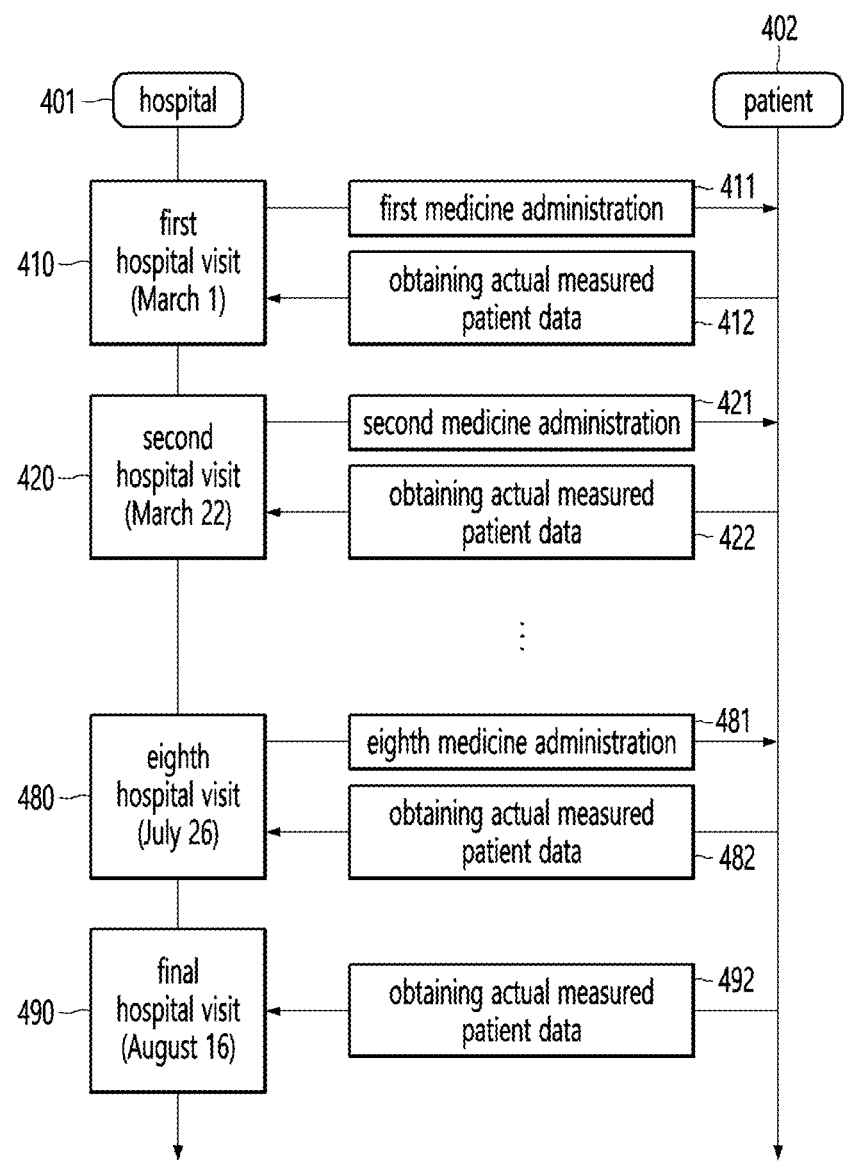
FIG. 4 is a view illustrating a general treatment process according to medicine administration.

FIG. 4 is a view illustrating a general treatment process according to medicine administration.

Referring to FIG. 4, a patient 402 may be administered a medicine when visiting a hospital 401.

The medicine may be a medicine for the purpose of treating thyroid ophthalmopathy and may be a medicine of which the administration is required a plurality of times during a treatment period. FIG. 4 illustrates the medicine that requires a total of eight times of administration at three-week intervals, but a medication administration regimen is not limited thereto.

For example, the medicine may be administered at one-week intervals for the first five doses, and then at one-month intervals thereafter. For another example, the medicine may be one that requires two doses at three-week intervals. For a yet another example, the medicine may be one that requires daily oral administration, and this is not limited to the examples described above.

The hospital 401 may mean a hospital where medical staff is assigned and/or work. Hereinafter, the actions performed by the hospital may be understood as to be performed by the medical staff assigned at the hospital, a hospital server, medical staff server, and/or medical staff device, and a duplicate description will be omitted hereinafter.

The patient 402 may be a patient with thyroid ophthalmopathy and may be a patient prescribed and administered a medicine for the purpose of treating the thyroid ophthalmopathy.

Referring to FIG. 4, the patient 402 may receive a first medicine administration 411 during a first visit 410 to the hospital 401, and in this case, the hospital 401 may obtain actual measured patient data 412 from the patient 402.

Thereafter, the patient 402 may receive a second medicine administration 421 during a second visit 420 to the hospital 401, and in this case, the hospital 401 may obtain actual measured patient data 422 from the patient 402.

In the same manner, similar procedures may be performed for the patient 402 during the third, fourth, fifth, sixth, and seventh visits to the hospital 401.

The patient 402 may be administered a medicine at the hospital 401 until an eighth visit 480 to the hospital, and at each visit, the hospital 401 may obtain actual measured patient data from the patient 402.

After the eighth medicine administration, the patient 402 may make a final visit 490 to the hospital 401, and at this time, the hospital 401 may also obtain actual measured patient data 492 from the patient 402.

Finally, according to the existing methods, the hospital 401 may obtain the total of nine patient data over 24 weeks, but since the interval between time points of obtaining the patient data is long, the continuity of data is weak, and the hospital 401 and the patient 402 may obtain only a limited number of patient data.

(2) Monitoring Method According to the Present Disclosure

Figure 5:
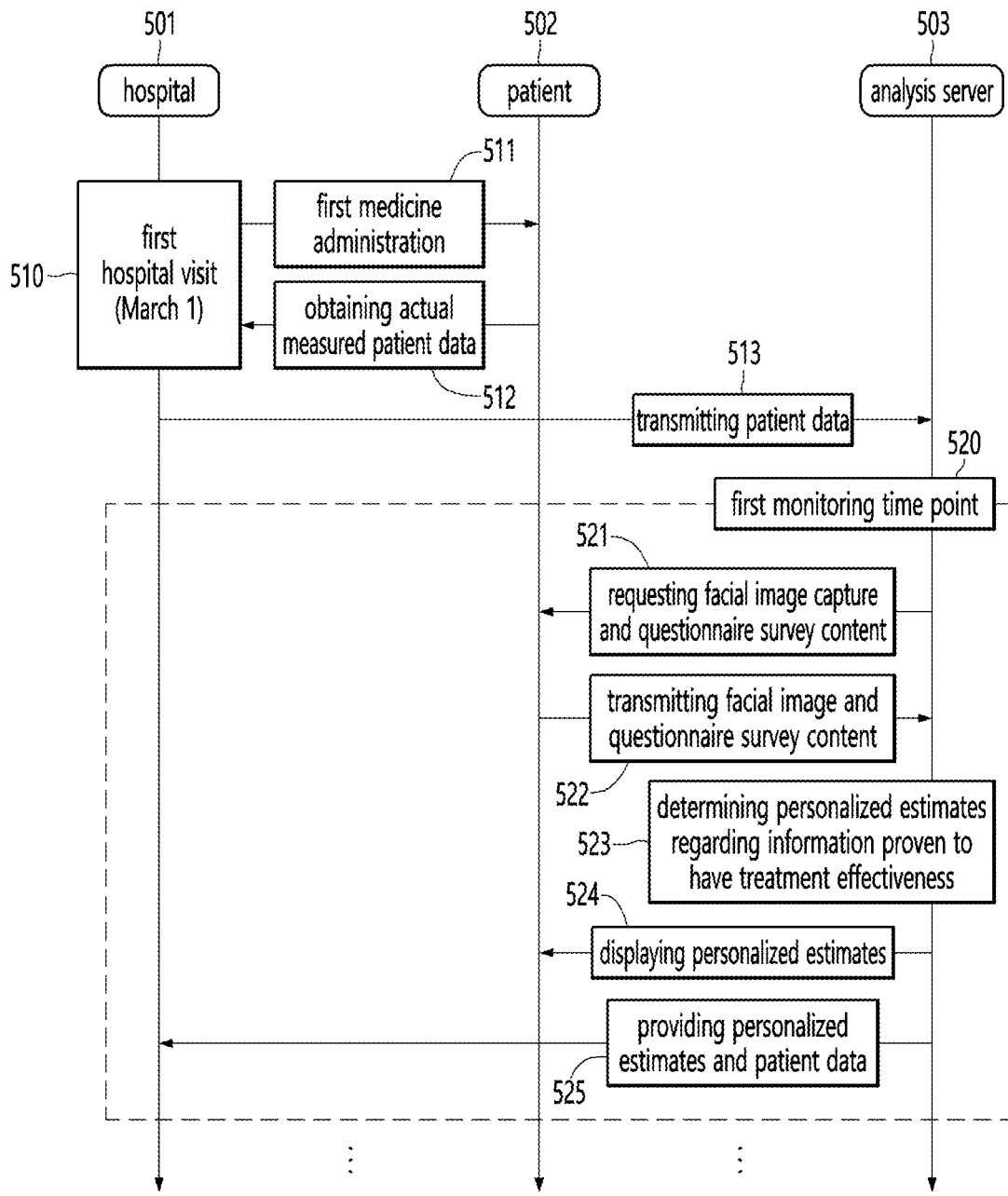
FIG. 5 is a view illustrating a method for monitoring a treatment process based on the medicine administration according to the exemplary embodiment.

FIG. 5 is a view illustrating a method for monitoring a treatment process based on the medicine administration according to the exemplary embodiment.

Referring to FIG. 5, a patient 502 may be administered a medicine when visiting a hospital 501. Specifically, when the patient 502 visits the hospital 501, medical staff assigned at the hospital 501 may administer the medicine to the patient 502. Hereinafter, it may be understood that a process of administering the medicine to the patient when visiting the hospital is carried out by the medical staff assigned at the hospital.

The medicine may be a medicine for the purpose of treating thyroid ophthalmopathy and may be a medicine of which the administration is required a plurality of times during a treatment period.

The hospital 501 may mean a hospital with the medical staff assigned thereat. Meanwhile, the actions performed by the hospital 501 may be understood as to be performed by the medical staff assigned at the hospital, a hospital server, medical staff server, and/or medical staff device, and a duplicate description is omitted below.

The patient 502 may be a patient with thyroid ophthalmopathy and may be a patient prescribed and administered a medicine for the purpose of treating thyroid ophthalmopathy. Meanwhile, hereinafter, actions performed by the patient 502 may be understood as being performed by the patient and/or the patient's user device, and a duplicate description is omitted below.

Referring to FIG. 5, the patient 502 may be provided with first medicine administration 511 during a first visit 510 to the hospital 501, and the hospital 501 may obtain actual measured patient data 512 from the patient 502. Specifically, when the patient 502 makes the first visit 510 to the hospital 501, the medical staff assigned at the hospital 501 may administer a first medicine to the patient 502, and the medical staff assigned at the hospital 501 may perform obtaining 512 actual measured patient data from the patient 502. Below, the process of obtaining, by the hospital, the patient data when the patient visits the hospital may be understood as being performed by the medical staff assigned at the hospital.

In addition, the hospital 501 may perform transmitting 513 the obtained patient data to an analysis server 503. Specifically, the hospital server, the medical staff server, and/or the medical staff device, which are disposed in the hospital 501 may perform transmitting 513 the patient data to the analysis server 503. Hereinafter, the process of transmitting, by the hospital, data to the analysis server may be understood as being performed by the hospital server, the medical staff server, and/or the medical staff device, which are disposed in the hospital.

The analysis server 503 may be a device that performs data transmission and reception with the hospital 501 and the patient 502, obtains patient data about the patient 502, determines and/or estimates the patient's condition, and provides the determined and/or estimated patient data to the hospital 501 and/or the patient 502. Specifically, the analysis server 503 performs the data transmission and reception with the hospital server, medical staff server, and/or medical staff device, which are disposed in the hospital 501, and may perform the data transmission and reception with a user device of the patient 502. In addition, the analysis server 503 transmits the determined and/or estimated patient data to the hospital server, the medical staff server, and/or the medical staff device, which are disposed in the hospital 501, and may transmit the determined and/or estimated patient data to the user device of the patient 502.

In addition, the analysis server 503 may be a device that stores the patient data and/or information related to thyroid ophthalmopathy, which are obtained from the hospital 501 and/or the patient 502, and provides the stored information to the hospital 501 and/or the patient 502. Specifically, the analysis server 503 transmits the stored information to the hospital server, the medical staff server, and/or the medical staff device, which are disposed in the hospital 501, and may transmit the stored information to the user device of the patient 502.

Meanwhile, a time point at which medicine administration begins may be understood as a time point at which treatment begins. This is not limited thereto, and medicine administration may begin after a time point at which the treatment begins.

Meanwhile, in the following, a time point at which the medicine administration has ended may be understood as a time point at which the treatment has ended. This is not limited thereto, and the treatment may also end after the time point at which the medicine administration has ended.

Meanwhile, in the following, a time point of medicine administration may be understood as a time point at which a patient visits the hospital and is administered a medicine. This is not limited thereto, and may also mean a time point at which the patient self-administers or orally takes the medicine, without visiting the hospital.

The patient data transmitted to the analysis server 503 by the hospital 501 may include an exophthalmos degree measurement value, a facial image of the patient at the time of measuring an exophthalmos degree, thyroid dysfunction management history, thyroid ophthalmopathy treatment information, patient physical information, and/or patient health information, which are obtained from the patient 502.

The exophthalmos degree measurement value may be an actual measured exophthalmos numerical value obtained directly from the patient by the medical staff, but it is not limited thereto. This value may also be an exophthalmos numerical value estimated from the patient's facial image captured when the patient visits the hospital.

The patient's facial image at the time of measuring the exophthalmos degree may mean a facial image corresponding to an exophthalmos degree measurement value. For example, in a case where the exophthalmos degree measurement value is an actual measured exophthalmos degree value, the patient's facial image at the time of the exophthalmos degree measurement may mean the facial image corresponding to the actual measured exophthalmos degree value.

The patient's thyroid dysfunction management history may include: a diagnosis name of thyroid dysfunction, a time point of the thyroid dysfunction diagnosis, blood test results, information on surgery and/or procedures due to the thyroid dysfunction, the type, dosage, and/or dose period of medicine administration for treating a thyroid dysfunction, but it is not limited thereto.

The thyroid dysfunction may indicate hyperthyroidism, but it is not limited thereto. The thyroid dysfunction may be understood to include symptoms related to the thyroid dysfunction. Specifically, the symptoms related to the thyroid dysfunction may include the hypothyroidism, thyroiditis, and/or thyroid nodules, but this is not limited to the examples described herein.

The blood test results may include hormone levels and antibody levels.

The hormone levels may be numerical values for hormones related to hyperthyroidism. For example, the hormones related to the hyperthyroidism may include Free T4 (Thyroxine), Thyroid-Stimulating Hormone (TSH), Free T3 (Triiodothyronine), and/or Total T3 (Triiodothyronine), but it is not limited thereto.

The antibody levels may be numerical values for antibodies related to hyperthyroidism. For example, the antibodies related to the hyperthyroidism may include Anti-TSH receptor Ab, Anti-TPO Ab, and/or Anti-Tg Ab, but it is not limited thereto.

In addition, the blood test results may also include levels of thyroglobulin (TG) and thyroxine-binding globulin (TBG).

Thyroid ophthalmopathy treatment information may include the type, dosage, and dose period of a medicine administered for treating thyroid ophthalmopathy, a steroid prescription date; a steroid prescription dose, a radiation treatment date, a thyroid ophthalmopathy surgery date, and/or a triamcinolone administration date, but it is not limited thereto.

The patient physical information and health information may include information based on the patient's physical characteristics, such as the patient's age, gender, race, and weight, but it is not limited thereto.

Meanwhile, in FIG. 5, it is shown that the hospital 501 performs transmitting 513 the patient data to the analysis server 503 after administering 511 the medicine to the patient 502, but it is not limited thereto, and the hospital 501 may also transmit the patient data to the analysis server 503 before administering the medicine to the patient 502. For example, the hospital may have the patient data for a patient having a thyroid dysfunction, and may also transmit the patient data to the analysis server before and/or after the patient is prescribed the medicine for the purpose of treating thyroid ophthalmopathy.

Referring to FIG. 5, patient monitoring may be performed at each first monitoring time point 520.

According to the exemplary embodiment, the first monitoring time point 520 may be a time point of a period during which the patient 502 visits the hospital 501 in order to be administered a medicine. Specifically, the first monitoring time point 520 may be any one time point of a treatment period during which the patient 502 visits the hospital 501 in order to be administered the medicine of which the administration is required a plurality of times.

Meanwhile, the treatment period may also include a period during which the patient 502 visits the hospital 501 for observing a condition thereof and the like, even after being administered all the medicines of which the administration requires the plurality of times.

According to the exemplary embodiment, the first monitoring time point 520 may be determined on the basis of a treatment monitoring cycle that is set.

In this case, the treatment monitoring cycle may be set on the basis of factors such as the characteristics of a medicine, a patient's condition, and/or the design of treatment process.

For example, the treatment monitoring cycle may be set such that monitoring is performed at specific intervals.

For a specific example, a treatment monitoring cycle may be set such that monitoring is performed at two-day intervals. Alternatively, the treatment monitoring cycle may be set such that monitoring is performed once every one to three weeks. In this case, the treatment monitoring cycle may be set such that monitoring is performed once every 1 to 1.5 weeks. Preferably, the treatment monitoring cycle may be set such that monitoring is performed once a week, but it is not limited thereto, and a specific period may be freely determined.

For another example, since an administration cycle may be different for each medicine, a treatment monitoring cycle may be set by considering the administration cycle of each medicine.

Specifically, the treatment monitoring cycle may be set to perform monitoring a set number of times between time points of medicine administration. For example, in a case where the medicine is administered at three-week intervals, the treatment monitoring cycle may be set such that monitoring is performed at one-week intervals, but it is not limited thereto.

As another example, since a time point at which a medicine takes effect may be different for each medicine, the treatment monitoring cycle may be set by considering the time point at which the medicine takes effect.

Specifically, a treatment monitoring cycle may be set to perform monitoring more frequently starting from a period when the treatment effectiveness begins to appear according to clinical trial results. Alternatively, the treatment monitoring cycle may be set to perform more frequent monitoring during a period where the treatment effectiveness appears steep according to the clinical trial results. For example, in a case where the treatment effectiveness is not noticeable in an early stage of the treatment and becomes noticeable after the sixth week, the treatment monitoring cycle may be set to monitor more frequently after the sixth week, but it is not limited thereto.

Meanwhile, the treatment monitoring cycle may also be distinguished into a monitoring cycle set by a hospital and a monitoring cycle desired by a patient.

Specifically, as described above, the monitoring cycle set by the hospital may be set according to the characteristics of the medicine, the patient's condition, and/or the design of the treatment process. The monitoring cycle desired by the patient is not limited to the monitoring cycle that is set by the hospital and may be freely set according to the patient's needs.

For example, the monitoring cycle set by the hospital is set to at least once between time points of medicine administration, and the monitoring cycle desired by the patient may be set to once every two days, but it is not limited thereto.

Alternatively, as described above, the monitoring cycle set by the hospital may be set according to the characteristics of the medicine, the patient's condition, and/or the design of the treatment process, but monitoring may be performed arbitrarily at any time desired by the patient without setting separately the monitoring cycle desired by the patient.

For example, in a case where the monitoring cycle set by the hospital is set to at least once between the time points of medicine administration, the monitoring is performed at least once between the time points of medicine administration according to the monitoring cycle set by the hospital, but additional monitoring may be performed at any time desired by the patient, and it is not limited thereto.

Meanwhile, according to the exemplary embodiment, without setting a separate treatment monitoring cycle, a first monitoring time point 520 may also be determined as an arbitrary time point at which the patient 502 desires monitoring.

In this case, the patient 502 may transmit a monitoring request to the analysis server 503 at any time, and the analysis server 503 may determine a time point of receiving the monitoring request from the patient 502 as a first monitoring time point 520, but it is not limited thereto.

Meanwhile, details related to the specific action performed at the first monitoring time point 520 will be described after describing FIG. 6.

Figure 6:
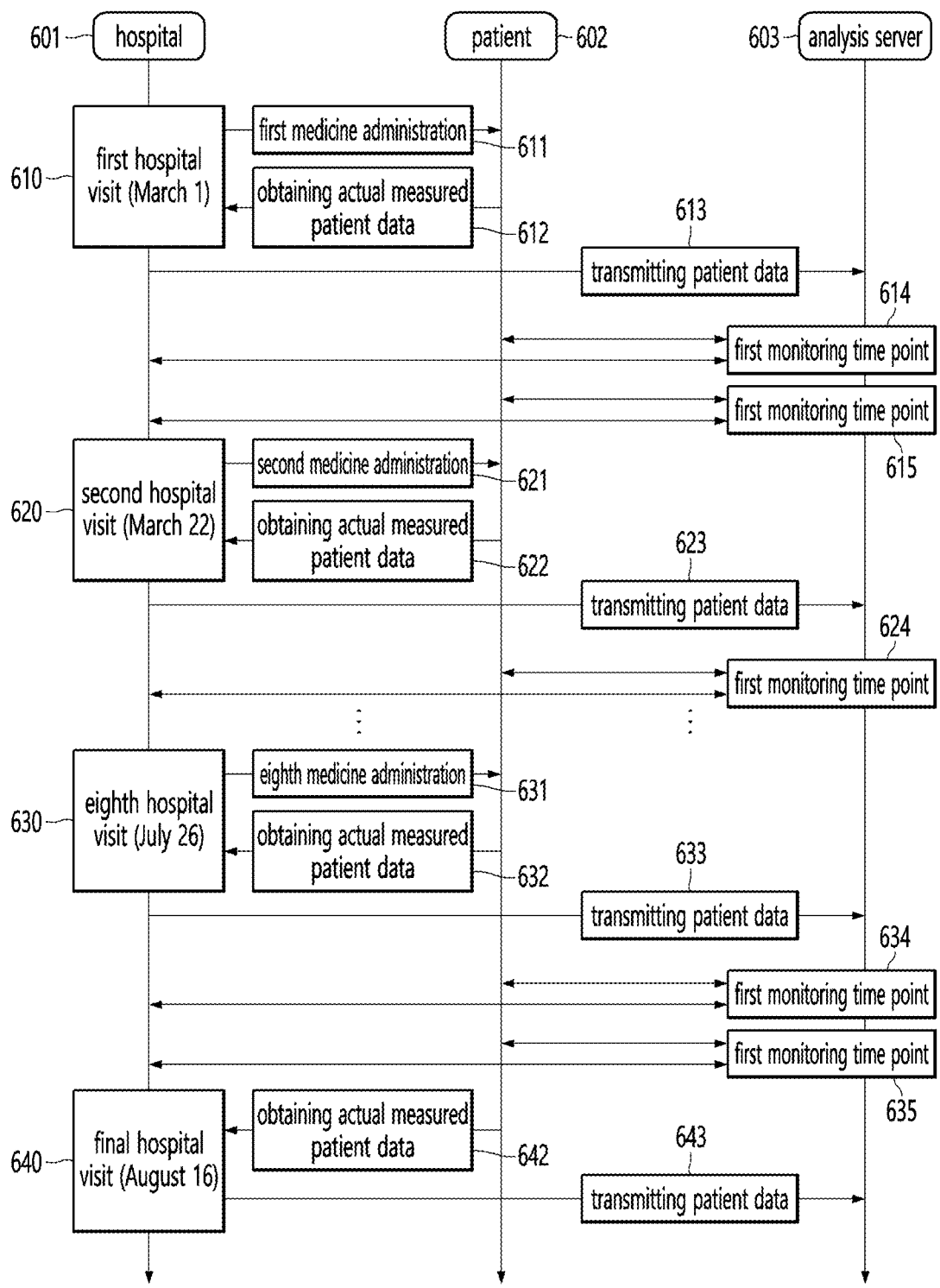
FIG. 6 is a view illustrating the overall monitoring treatment process based on the medicine administration according to the exemplary embodiment.

FIG. 6 is a view illustrating the overall monitoring treatment process based on the medicine administration according to the exemplary embodiment.

Referring to FIG. 6, a patient 602 may be administered a medicine when visiting a hospital 601. Specifically, when the patient 602 visits the hospital 601, medical staff assigned at the hospital 601 may administer the medicine to the patient 602. Hereinafter, it may be understood that a process of administering the medicine to the patient when visiting the hospital is carried out by the medical staff assigned at the hospital.

The medicine may be a medicine for the purpose of treating thyroid ophthalmopathy and may be a medicine of which the administration is required a plurality of times during a treatment period. FIG. 6 illustrates monitoring for the medicine that requires a total of eight times of administration at 3-week intervals, but a medication administration regimen is not limited thereto.

Meanwhile, with respect to the hospital 601, the patient 602, and an analysis server 603 in FIG. 6, the content of the hospital 501, patient 502, and analysis server 503 described above in FIG. 5 may be applied, so a duplicate description is omitted.

Referring to FIG. 6, the patient 602 may be administered a first medicine 611 at a time point 610 of a first visit to the hospital 601, and the hospital 601 may obtain actual measured patient data 612 from the patient 602. Specifically, at the time point 610 of the patient's 602 first visit to the hospital 601, the medical staff assigned at the hospital 601 may administer the first medicine to the patient 602, and the medical staff assigned at the hospital 601 may perform obtaining 612 the actual measured patient data from the patient 602. Below, the process of obtaining, by the hospital, the patient data when the patient visits the hospital may be understood as being performed by the medical staff assigned at the hospital.

In addition, the hospital 601 may perform transmitting 613 the obtained patient data to the analysis server 603. Specifically, a hospital server, medical staff server, and/or medical staff device, which are disposed in the hospital 601, may perform transmitting 613 the patient data to the analysis server 603. Hereinafter, the process of transmitting data to the analysis server by the hospital may be understood as being performed by the hospital server, the medical staff server, and/or the medical staff device, which are disposed in the hospital.

The details related to the transmitting the patient data to the analysis server 603 by the hospital 601 may be applied with the details described above in the description where the hospital 501 performs transmitting 513 the patient data to the analysis server 503 in FIG. 5, so a duplicate description is omitted.

Referring to FIG. 6, patient monitoring may be performed at a first monitoring time point 614 given for the first time after the first hospital visit time point 610, and patient monitoring may be performed at a first monitoring time point 615 given for the second time after the first monitoring time point 614 given for the first time. With respect to the determining of the first monitoring time point, the content described above in the description where the first monitoring time point 520 is determined in FIG. 5 may be applied with, so a duplicate description is omitted.

Referring to FIG. 6, after the first monitoring time point 615 given for the second time, the patient 602 may be administered a second medicine 621 at a time point 620 of a second visit to the hospital 601, and the hospital 601 may obtain actual measured patient data 622 from the patient 602.

Items of actual measured patient data obtained at the time point 620 of the second hospital visit and the actual measured patient data obtained at the time point 610 of the first hospital visit may be the same with each other, but it is not limited thereto. Some of the data items may be the same and some may be different, or the data items may also be different from each other. For example, the actual measured patient data obtained at the time point 610 of the first hospital visit may include an exophthalmos degree measurement value obtained from the patient 602, a facial image of the patient 602 at a time point of exophthalmos degree measurement, thyroid dysfunction management history, patient physical information, and patient health information. The actual measured patient data obtained at the time point 620 of the second hospital visit may include only an exophthalmos degree measurement value obtained from the patient 602 and a facial image of the patient 602 at a time point of exophthalmos degree measurement. That is, the thyroid dysfunction management history, the patient physical information, and the patient health information, which are obtained at the time point 610 of the first hospital visit may be used as is, as the patient's 602 thyroid dysfunction management history, patient physical information, and patient health information at the time point 620 of the second hospital visit, and the data items are not limited to the examples described above.

The hospital 601 may perform transmitting 623 the obtained patient data to the analysis server 603.

The items of the patient data transmitted to the analysis server 603 by the hospital 601 at the time point 620 of the second hospital visit and the patient data transmitted to the analysis server 603 by the hospital 601 at the time point 610 of the first hospital visit may be the same with each other, but it is not limited thereto. Some of the data items may be the same and some may be different, or the data items may also be different from each other. For example, the patient data transmitted to the analysis server 603 by the hospital 601 at the time point 610 of the first hospital visit may include an exophthalmos degree measurement value obtained from the patient 602, a facial image of the patient 602 at a time point of exophthalmos degree measurement, thyroid dysfunction management history, patient physical information, and patient health information. The patient data transmitted to the analysis server 603 by the hospital 601 at the time point 620 of the second hospital visit may include only an exophthalmos degree measurement value obtained from the patient 602 and a facial image of the patient 602 at a time point of exophthalmos degree measurement. That is, the analysis server 603 may use the thyroid dysfunction management history, the patient physical information, and the patient health information, which are obtained at the time point 610 of the first hospital visit as is, as the patient's 602 thyroid dysfunction management history, the patient physical information, and the patient health information that are corresponding to the time point 620 of the second hospital visit, and the data items are not limited to the examples described above.

Meanwhile, in FIG. 6, it is illustrated that there are two first monitoring time points 614 and 615 between the time point 610 of the first hospital visit and the time point 620 of the second hospital visit, but the number of first monitoring time points is not limited thereto, and the first monitoring time points may be arranged at various numbers on the basis of a set monitoring cycle. For example, there may be one first monitoring time point between the time point 610 of the first hospital visit and the time point 620 of the second hospital visit, or there may also be three or more first monitoring time points.

Referring to FIG. 6, patient monitoring may be performed at a first monitoring time point 624 given for the third time after the time point 620 of the second hospital visit.

Thereafter, each first monitoring and hospital visits may be performed continuedly.

Referring to FIG. 6, the patient 602 may have administration 631 of an eighth medicine at a time point 630 of an eighth visit to the hospital 601, and the hospital 601 may obtain actual measured patient data 632 from the patient 602.

In addition, the hospital 601 may perform transmitting 633 the obtained patient data to the analysis server 603.

Referring to FIG. 6, two sessions 634 and 635 of performing first monitoring may be conducted after the time point 630 of the eighth hospital visit, and the number of times of first monitoring is not limited thereto.

Referring to FIG. 6, after the eighth medicine administration, the patient 602 may make a final visit 640 to the hospital 601, and in this case, the hospital 601 may obtain actual measured patient data 642 from the patient 602 and perform transmitting 643 the obtained patient data to the analysis server 603.

During the medicine administration process, the first monitoring may be performed multiple times throughout the medicine administration process as described in FIG. 6, but it is not limited thereto and the first monitoring may also be performed only in some intervals.

Meanwhile, in FIG. 6, a time interval between the time points of medicine administration is three weeks, and since the time interval between the time points of medicine administration is long, it is illustrated such that a plurality of times of first monitoring is performed between the time points of medicine administration, but it is not limited thereto. For example, in a case of a medicine administered orally daily according to a medication administration regimen, the first monitoring may be performed once after a plurality of time points of medicine doses, or the first monitoring may be performed once between the time points of the medicine doses, but it is not limited thereto.

Referring back to FIG. 5, at the first monitoring time point 520, the patient 502 may be requested to capture a facial image and fill out questionnaire survey content.

In this case, a subject that is requested to capture the facial image and fill out the questionnaire survey content may be a user device of the patient 502. Hereinafter, the process where the patient is requested to capture the facial image and fill out the questionnaire survey content may be understood to be performed by the user device.

The patient 502 may capture a facial image and transmit the facial image upon request for facial image capture. For example, the patient 502 may capture the facial image in response to a facial image capture request 521 from the analysis server 503 and perform transmitting 522 the facial image to the analysis server 503. For a more specific example, the patient 502 may capture the facial image in response to the facial image capture request 521 from the analysis server 503 by using the user device, and perform transmitting 522 the facial image to the analysis server 503 through the user device. Below, it may be understood that the process of capturing, by the patient, the facial image and transmitting the facial image to the analysis server is performed by using the user device.

In this case, the facial image may mean a front facial image and/or a side facial image of the patient, but it is not limited thereto, and the facial image may include: a panoramic image from the front to the side of the patient; a video obtained by recording the face; and/or a facial image at any angle between the front and the side of the patient.

Meanwhile, in a case where the patient's face is rotated left and right and/or up and down when a facial image is captured, distortion may also occur in the facial image. In a case when there is the distortion in the facial image, the accuracy of facial image analysis may decrease, so the patient 502 may be provided with a photographing guide in order to obtain a preferable facial image. By capturing the facial image following the photographing guide, the patient 402 may capture the facial image with the same composition each time a facial image is captured. Specific details regarding the photographing guide will be described later.

Meanwhile, since facial appearance (e.g. swelling, etc.) may change according to the time of day, the patient 502 may receive a facial image capture request at a preset image capturing time.

On the other hand, since facial appearance may change depending on the time of day, the patient 502 may also be requested to capture his or her facial image at a plurality of time points different from each other during the day. In this case, analysis results for each of the obtained facial images may be obtained, and an average value and the like of the obtained analysis results may be determined as a correction value for that day. Alternatively, an analysis result with the highest accuracy among the analysis results for each of the obtained facial images may also be determined as a value for that day. Alternatively, an analysis result for a facial image, which best satisfies the photographing guide, among the obtained facial images may also be determined as a value for that day.

On the other hand, the patient 502 may also receive a facial image capture request so as to capture multiple facial images at a time point of facial image capture. In this case, an analysis result for a facial image, which best satisfies the criteria of the photographing guide, among the obtained facial images may also be determined as a value for that time point. Alternatively, analysis results for each of the obtained facial images may be obtained, and an average value or a median value of the obtained analysis results may be determined as a correction value at that time point. Alternatively, an analysis result with the highest accuracy among the analysis results for each of the obtained facial images may also be determined as a value for that time point.

On the other hand, the patient 502 may receive a facial image capture request so as to capture a facial video at a time point of facial image capture. In this case, an analysis result for a frame, which best satisfies the criteria of the photographing guide, among the frames included in the obtained facial video may also be determined as a value at that time point. Alternatively, analysis results for each frame included in the obtained facial video may be obtained, and an average value or a median value of the obtained analysis results may be determined as a correction value at that time point. Alternatively, an analysis result with the highest accuracy among the analysis results for each of frames included in the obtained facial video may also be determined as a value for that time point.

As described above, as the patient 502 receives the facial image capture request, the influence of changes in the patient's facial appearance may be reduced, the changes occurring depending on the degree to which the patient exerts force on his or her face during the facial image capture, the patient's condition, the patient's intention, etc.

The patient 502 may fill out questionnaire survey content and transmit the questionnaire survey content in response to a questionnaire survey content request. For example, the patient 502 may fill out the questionnaire survey content in response to the questionnaire survey content request 521 from the analysis server 503, and perform transmitting 522 the questionnaire survey content to the analysis server 503.

For a more specific example, the patient 502 may fill out the questionnaire survey content by using his or her user device in response to the questionnaire survey content request 521 from the analysis server 503, and transmit the written questionnaire survey results to the analysis server 503 through the user device. Below, it may be understood that the process of filling out, by the patient, the questionnaire survey content and transmitting the questionnaire survey results to the analysis server is performed by using the user device.

In filling out questionnaire survey content, the questionnaire survey content may be filled out in a manner of entering, by the patient, text into the user device and/or in a manner of checking separate check boxes for preset questionnaire survey items. This is not limited thereto, and in addition to the preset questionnaire survey items, the questionnaire survey content may also be filled out in a manner of entering content by the patient into the user device, the content being desired to be transmitted to the analysis server 503 and/or the hospital 501 by the patient.

The questionnaire survey content requested from the patient 502 may include: questionnaire survey content related to determining thyroid ophthalmopathy activity and questionnaire survey content related to determining thyroid ophthalmopathy severity.

For example, the questionnaire survey content related to determining the thyroid ophthalmopathy activity may include whether there is spontaneous pain in a posterior part of an eye and whether there is pain during eye movement, but it is not limited thereto.

For example, the questionnaire survey content related to the determining of the thyroid ophthalmopathy severity may include whether diplopia is present or not and the content of quality-of-life questionnaire (Go-QoL), but it is not limited thereto.

Based on the facial image and questionnaire survey content obtained from the patient 502, the patient's 502 personalized estimates regarding information proven to have the treatment effectiveness through the clinical trial of the medicine for the purpose of treating thyroid ophthalmopathy may be obtained.

Specifically, referring back to FIG. 5, the analysis server 503 may perform determining 523 the patient's 502 personalized estimates regarding information proven to have the treatment effectiveness through the clinical trial of the medicine for the purpose of treating thyroid ophthalmopathy by using the facial image and questionnaire survey content, which are obtained from the patient 502. More specifically, the analysis server 503 may perform the determining 523 the patient's 502 personalized estimates regarding the information proven to have the medicine effectiveness through the clinical trial of the medicine for the purpose of treating thyroid ophthalmopathy by using the facial image and questionnaire survey content, which are received from the patient's user device. Below, the facial image and questionnaire survey content obtained from the patient may be understood as the facial image and questionnaire survey content received from the patient's user device.

The treatment effectiveness proven through the clinical trial of the medicine for the purpose of treating thyroid ophthalmopathy may include alleviation of exophthalmos degrees, improvement in CAS numerical values, and improvement in diplopia. Accordingly, the information proven to have the treatment effectiveness may be exophthalmos degree information, CAS information, and/or diplopia information.

Meanwhile, the patient's 502 personalized estimates regarding indicators proven with the effectiveness of medicine at an approval stage for the medicine for the purpose of treating thyroid ophthalmopathy may be obtained on the basis of the facial image and questionnaire survey content obtained from the patient 502.

Specifically, the analysis server 503 may determine the patient's 502 personalized estimates for the indicators proven to have the effectiveness of medicine in the approval stage of the medicine for the purpose of treating thyroid ophthalmopathy by using the facial images and questionnaire survey content obtained from the patient 502.

In this case, the indicators proven with the effectiveness of medicine at the approval stage of the medicine for the purpose of treating thyroid ophthalmopathy may include the exophthalmos degree information, CAS information, and diplopia information.

A numerical value of an exophthalmos degree shown in a facial image obtained from the patient 502 may be obtained as a personalized estimate of exophthalmos degree information of the patient 502. For example, the analysis server 503 may determine the exophthalmos numerical value shown in the facial image obtained from the patient 502 as the patient's 502 personalized estimate of the exophthalmos degree information.

For a more specific example, the analysis server 503 may determine an exophthalmos numerical value by using a single facial image in a case where a facial image obtained from the patient 502 is the single facial image (e.g., in a case where a facial image is captured for the first time). A method for determining the exophthalmos numerical value by using the single facial image is described later in (1) Exophthalmos degree determination method based on a facial image—1, (2) Exophthalmos degree determination method based on a facial image—2, and (4) Exophthalmos degree determination method based on a facial image—4 of 5. Exophthalmos degree determination method based on a facial image.

In a case of obtaining two facial images from the patient 502 (e.g., a case where there is included one facial image taken previously, and the two facial images may include a facial image at a first time point and a facial image at a second time point later than the first time point), the analysis server 503 may determine an exophthalmos numerical value by using the two facial images obtained from the patient 502.

Specifically, an exophthalmos numerical value at the second time point may be determined by using the facial image at the first time point, the facial image at the second time point, and an exophthalmos numerical value at the first time point. Alternatively, the exophthalmos numerical value at the first time point may be determined by using the facial image at the first time point, the facial image at the second time point, and the exophthalmos numerical value at the second time point. The method for determining the exophthalmos numerical value by using two facial images is described later in (3) Facial image-based exophthalmos degree determination method—3 of 5. Facial image-based exophthalmos degree determination method.

The analysis server 503, in a case of three facial images obtained from the patient 502, may determine an exophthalmos numerical value at the third time point (e.g., a case where there are included two facial images taken previously, and the three facial images may include a facial image at a first time point, a facial image at a second time point later than the first time point, and a facial image at a third time point later than the second time point) by using the facial image at the first time point, the facial image at the third time point, and the exophthalmos numerical value at the first time point, and the analysis server 503 may determine an exophthalmos numerical value at the third time point by using the facial image at the second time point, the facial image at the third time point, and the exophthalmos numerical value at the second time point. Thereafter, an average value of these two determined exophthalmos numerical values at the third time point may be determined as an exophthalmos numerical value at the third time point.

That is, by using the facial images and exophthalmos numerical values at the respective time points other than the third time point at which an exophthalmos degree is to be determined, and by using the facial image at the third time point at which the exophthalmos degree is to be determined, the plurality of exophthalmos numerical values at third time point is determined, and then an average value of the plurality of determined exophthalmos numerical values at the third time point may be determined as a final exophthalmos numerical value at the third time point.

Alternatively, the analysis server 503 may also determine the exophthalmos numerical value at the third time point by using the facial image at the second time point closest to the third time point, the exophthalmos numerical value at the second time point, and the facial image at the third time point. The method for determining an exophthalmos numerical value by using two facial images is described later in (3) Facial image-based exophthalmos degree determination method—3 of 5. Facial image-based exophthalmos degree determination method.

In a case where there are four or more facial images obtained from the patient 502, the analysis server 503 may determine a plurality of exophthalmos numerical values as in the case of the three facial images described above by using not only facial images and exophthalmos numerical values at respective time points other than a time point at which an exophthalmos degree is to be determined but also a facial image at the time point at which the exophthalmos degree is to be determined, thereby determining an average value of the determined plurality of exophthalmos numerical values as an exophthalmos numerical value at the time point at which the exophthalmos degree is to be determined.

The method for determining an exophthalmos numerical value by using two facial images is described later in (3) Facial image-based exophthalmos degree determination method—3 of 5. Facial image-based exophthalmos degree determination method.

Alternatively, the analysis server 503 may determine an exophthalmos numerical value at a time point at which the exophthalmos numerical value is to be determined by using a facial image at the time point at which the exophthalmos numerical value is to be determined and by using a facial image and exophthalmos numerical value at a time point closest to the time point at which the exophthalmos numerical value is to be determined. The method for determining an exophthalmos numerical value by using two facial images is described later in (3) Facial image-based exophthalmos degree determination method—3 of 5. Facial image-based exophthalmos degree determination method.

In addition, even in a case where there is a plurality of facial images obtained from the patient 502, the analysis server 503 may also determine an exophthalmos numerical value by using the method for determining an exophthalmos numerical value by using a single facial image.

The effectiveness of medicine is to alleviate exophthalmos degrees, so in a case where an exophthalmos numerical value decreases at a later time point rather than a previous time point, it may be determined that a medicine is effective.

Meanwhile, a trend in exophthalmos degrees may be obtained on the basis of facial images obtained from the patient 502 as the patient's 502 personalized estimate of the exophthalmos degree information. For example, the analysis server 503 may determine the trend in the exophthalmos degrees on the basis of the facial images obtained from the patient 502 as the patient's 502 personalized estimate for the exophthalmos degree information.

Since the effectiveness of medicine is to alleviate exophthalmos degrees, so in a case where an exophthalmos degree is determined to have decreased between a previous time point and a later time point even without determining an actual exophthalmos numerical value, it may be determined that a medicine is effective, whereby a trend in the exophthalmos degrees may be obtained as the patient's 502 personalized estimate for the exophthalmos degree information. In this case, the trend in the exophthalmos degrees may mean the trend of changes in the exophthalmos degrees.

That is, in a case where a trend in the exophthalmos degrees based on facial images obtained from the patient 502 is determined to be a decreasing trend, it may be determined that a medicine is effective.

A trend in exophthalmos degrees may be determined on the basis of the patient's 502 facial images obtained at two time points. In this case, the trend in the exophthalmos degrees may mean the trend of changes in the exophthalmos degrees.

Specifically, a variable related to an exophthalmos degree is obtained from each of the patient's 502 facial images obtained at two time points, and the trend in the exophthalmos degrees may be determined on the basis of a comparison of the variables related to the exophthalmos degrees. A more specific method for determining the trend in the exophthalmos degrees is described later.

Meanwhile, two time points at which a trend in exophthalmos degrees is to be determined may be two adjacent time points among time points at which facial images are obtained from the patient 502. For example, by comparing a facial image obtained at a first monitoring time point given for the n-th time with a facial image obtained at a first monitoring time point given for the (n+1)-th time, a trend in the exophthalmos degrees between the first monitoring time point given for the n-th time and the first monitoring time point given for the (n+1)-th time may be determined. Based on the trend of the determined exophthalmos degrees, it may be determined whether a medicine is effective or not.

This is not limited thereto, and two time points may be freely selected depending on the purpose of determining a trend in exophthalmos degrees. For example, by comparing a facial image obtained at one time point between a first medicine administration time point and a second medicine administration time point and a facial image obtained at one time point between the second medicine administration time point and a third medicine administration time point, the trend in the exophthalmos degrees according to second medicine administration may be determined. The effectiveness of medicine may be determined on the basis of the trend in the determined exophthalmos degrees, but it is not limited thereto.

Meanwhile, a trend in exophthalmos degree may also be determined by having one fixed time point out of two time points that are for determining the trend in the exophthalmos degrees and by allowing the other time point to be changed. For example, based on a facial image obtained at a first monitoring time point given for the n-th time, a trend in exophthalmos degrees between an (n−1)-th time point and an n-th time point is determined by a comparison with a facial image obtained for the (n−1)-th time, and a trend in exophthalmos degrees between an (n—2)-th time point and the n-th time point is determined by a comparison with a facial image obtained for the (n—2)-th time, whereby trend determination for various exophthalmos degrees are possible, but this is not limited to the example described above.

A CAS numerical value based on a facial image and questionnaire survey content obtained from the patient 502 may be obtained as the patient's 502 personalized estimate for CAS information. For example, the analysis server 503 may determine the CAS numerical value by using the facial image and questionnaire survey content obtained from the patient 502 as the patient's 502 personalized estimate for the CAS information.

Specifically, whether redness of eyelid is present or not, whether redness of conjunctiva is present or not, whether swelling of eyelid is present or not, whether swelling of conjunctiva is present or not, and whether swelling of lacrimal caruncle is present or not may be determined by using the obtained facial images and a trained prediction model. A CAS numerical value may be determined on the basis of content on whether spontaneous pain in a posterior part of an eye is present or not and whether pain during eye movement is present or not, the content being included in the questionnaire survey content.

Since the effectiveness of medicine is a decrease in a CAS numerical value, it may be determined that a medicine is effective in a case where the CAS numerical value decreases at a later time point rather than a previous time point.

Meanwhile, a trend in CAS may be obtained on the basis of the facial images and questionnaire survey content obtained from the patient 502 as the patient's 502 personalized estimate for the CAS information. For example, the analysis server 503 may determine the trend in CAS by using the facial images and questionnaire survey content obtained from the patient 502 as the patient's 502 personalized estimate for the CAS information.

Since the effectiveness of medicine is a decrease in a CAS numerical value, the trend in CAS may be obtained as the patient's 502 personalized estimate for the CAS information in a case where a trend of changes in CAS between a previous time point and a later time point is determined to be a decreasing trend because it may be determined that a medicine is effective. In this case, the trend in CAS may mean the trend of changes in CAS.

The trend in CAS may be determined on the basis of the patient's 502 facial images and questionnaire survey content obtained at two time points.

Specifically, CAS numerical values are obtained from the patient's 502 facial images and questionnaire survey content obtained at two time points, respectively, and a trend in CAS may be determined on the basis of a comparison of the obtained CAS numerical values. The method for determining CAS numerical values by using facial images and questionnaire survey content has been described above, so a duplicate description is omitted.

Meanwhile, the two time points at which the trend in CAS is determined may be adjacent time points among the time points at which the facial images and questionnaire survey content are obtained from the patient 502. The description for the case where the two time points for determining the trend are adjacent time points has been described above in the describing of the trend determination for exophthalmos degrees, so a duplicate description is omitted.

This is not limited thereto, and two time points may be freely selected depending on the purpose of determining a trend in CAS. The description for the case where two time points for determining a trend are freely selected has been described above in the describing of the trend determination for exophthalmos degrees, so a duplicate description is omitted.

Meanwhile, a trend in CAS may also be determined by having one fixed time point out of two time points that are for determining the trend in CAS and by allowing the other time point to be changed. The description for the case where one of the two time points for determining the trend is fixed has been described above in the describing of the trend determination for exophthalmos degrees, so a duplicate description is omitted.

A value for determining whether the patient has diplopia may be obtained on the basis of questionnaire survey content obtained from the patient 502 as the patient's 502 personalized estimate for diplopia information. For example, the analysis server 503 may obtain the value for determining whether the patient has diplopia by using the questionnaire survey content obtained from the patient 502 as the patient's 502 personalized estimate for the diplopia information.

The value for determining whether the patient has diplopia may be a value indicating either the presence of diplopia or the absence of diplopia. Meanwhile, in a case of determining whether the patient has diplopia by using the Gorman criteria, the value for determining whether the patient has diplopia may be a value indicating one of grades for no diplopia, intermittent diplopia, diplopia at extreme gaze, and persistent diplopia.

Specifically, a value for determining whether the patient has diplopia may be obtained on the basis of the patient's response content, regarding whether diplopia is present or not, included in the obtained questionnaire survey content.

Since the effectiveness of medicine is the improvement of diplopia, it may be determined that a medicine is effective in a case where the diplopia is present at a previous time point and then disappeared at a later time point.

Meanwhile, a trend in diplopia may be obtained on the basis of questionnaire survey content obtained from the patient 502 as the patient's 502 personalized estimate for diplopia information. For example, the analysis server 503 may determine the trend in diplopia on the basis of the questionnaire survey content obtained from the patient 502 as the patient's 502 personalized estimate for the diplopia information.

Since the effectiveness of medicine is the improvement of diplopia, it may be determined that a medicine is effective in a case where it is determined that a trend in diplopia is a decreasing trend between a previous time point and a later time point, whereby the trend in diplopia may be obtained as the patient's 502 personalized estimate for the diplopia information. In this case, the trend in diplopia may mean a trend of changes in diplopia.

The trend in diplopia may be determined on the basis of the patient's 502 questionnaire survey content obtained at two time points.

Specifically, a value for determining whether the patient has diplopia or not is obtained from each of the patient's 502 questionnaire survey content obtained at two time points, and a trend in diplopia may be determined on the basis of a comparison of the obtained values for determining whether the patient has diplopia. The method for obtaining the value for determining whether the patient has diplopia by using the questionnaire survey content has been described above, so a duplicate description is omitted.

Meanwhile, two time points at which a trend in diplopia is determined may be time points adjacent to each other among the time points at which the questionnaire survey content is obtained from the patient 502. The description for the case where the two time points for determining the trend are adjacent time points has been described above in the describing of the trend determination for exophthalmos degrees, so a duplicate description is omitted.

This is not limited thereto, and two time points may be freely selected depending on the purpose of determining a trend in diplopia. The description for the case where two time points for determining a trend are freely selected has been described above in the describing of the trend determination for exophthalmos degrees, so a duplicate description is omitted.

Meanwhile, a trend in diplopia may also be determined by having one fixed time point out of two time points that are for determining the trend in diplopia and by allowing the other time point to be changed. The description for the case where one of the two time points for determining the trend is fixed has been described above in the describing of the trend determination for exophthalmos degrees, so a duplicate description is omitted.

Meanwhile, the patient's 502 personalized estimate for eyelid retraction information may be obtained on the basis of a facial image obtained from the patient 502. For example, the analysis server 503 may determine the patient's 502 personalized estimate for eyelid retraction information by using a facial image obtained from the patient 502.

A numerical value of eyelid retraction shown in the facial image obtained from the patient 502 may be obtained as the patient's 502 personalized estimate for the eyelid retraction information. For example, the analysis server 503 may determine the value of eyelid retraction shown in the facial image obtained from the patient 502 as the patient's 502 personalized estimate of the eyelid retraction information. The specific method for determining an eyelid retraction numerical value by using the facial image is described below.

Meanwhile, a trend in eyelid retraction based on facial images obtained from the patient 502 as the patient's 502 personalized estimate for the eyelid retraction information may be obtained. For example, the analysis server 503 may determine the trend in the eyelid traction based on the facial images obtained from the patient 502 as the patient's 502 personalized estimate for the eyelid traction information. In this case, the trend in eyelid retraction may mean a trend of changes in the eyelid retraction.

The trend in the eyelid retraction may be determined on the basis of facial images of the patient 502 obtained at two time points.

Specifically, a variable related to eyelid retraction is obtained from each of the patient's 502 facial images obtained at two time points, and a trend in eyelid retraction may be determined on the basis of a comparison of the obtained variables related to the eyelid retraction. A more specific method for determining a trend in eyelid retraction is described later.

Meanwhile, two time points at which a trend of eyelid retraction is to be determined may be two time points adjacent to each other among time points at which facial images are obtained from the patient 502. The description for the case where the two time points for determining the trend are adjacent time points has been described above in the describing of the trend determination for exophthalmos degrees, so a duplicate description is omitted.

This is not limited thereto, and two time points may be freely selected depending on the purpose of determining a trend in eyelid retraction. The description for the case where two time points for determining a trend are freely selected has been described above in the describing of the trend determination for exophthalmos degrees, so a duplicate description is omitted.

Meanwhile, a trend in eyelid retraction may also be determined by having one fixed time point out of two time points that are for determining the trend in the eyelid retraction and by allowing the other time point to be changed. The description for the case where one of the two time points for determining the trend is fixed has been described above in the describing of the trend determination for exophthalmos degrees, so a duplicate description is omitted.

Meanwhile, the patient's 502 personalized estimate for thyroid ophthalmopathy severity information may be obtained on the basis of a facial image and questionnaire survey content obtained from the patient 502. For example, the analysis server 503 may determine the patient's 502 personalized estimate for the thyroid ophthalmopathy severity information by using the facial image and questionnaire survey content obtained from the patient 502. In this case, the thyroid ophthalmopathy severity information may include one of states of none, mild (moderate), and severe (serious) of the thyroid ophthalmopathy severity, but it is not limited thereto.

An exophthalmos degree and an eyelid retraction numerical value, which are presented in a facial image obtained from the patient 502, may be obtained in order to obtain the patient's 502 personalized estimate for the thyroid ophthalmopathy severity. In addition, a rating of soft tissue invasion may be determined by using the facial image obtained from the patient 502 and a trained prediction model. In addition, a score for whether the patient has diplopia and a score for the content of quality-of-life questionnaire may be obtained on the basis of questionnaire survey content obtained from the patient 502.

The patient's 502 personalized estimate of the thyroid ophthalmopathy severity may be obtained on the basis of the obtained exophthalmos numerical value, eyelid retraction numerical value, rating for soft tissue invasion, score for whether the patient has diplopia, and score for the content of quality-of-life questionnaire.

Meanwhile, a trend in thyroid ophthalmopathy severities may be obtained on the basis of facial images and questionnaire survey content obtained from the patient 502 as the patient's 502 personalized estimate for the thyroid ophthalmopathy severities. For example, the analysis server 503 may determine a trend in the thyroid ophthalmopathy severities on the basis of the facial images and questionnaire survey content obtained from the patient 502 as the patient's 502 personalized estimate for the thyroid ophthalmopathy severities. In this case, the trend in thyroid ophthalmopathy severities may mean the trend of changes in thyroid ophthalmopathy.

A trend in thyroid ophthalmopathy severities may be determined on the basis of the patient's 502 facial images and questionnaire survey content obtained at two time points.

Specifically, thyroid ophthalmopathy severity information are obtained from the patient's 502 facial images and questionnaire survey content obtained at two time points, and a trend in thyroid ophthalmopathy severities may be determined on the basis of a comparison using the obtained thyroid ophthalmopathy severity information.

Meanwhile, the two time points at which the trend in the thyroid ophthalmopathy severities is determined may be time points adjacent to each other among time points at which the facial images and questionnaire survey content are obtained from the patient 502. The description for the case where two time points for determining a trend are adjacent time points has been described above in the describing of the trend determination for exophthalmos degrees, so a duplicate description is omitted.

This is not limited thereto, and two time points may be freely selected depending on the purpose of determining a trend of thyroid ophthalmopathy severities. The description for the case where two time points for determining a trend are freely selected has been described above in the describing of the trend determination for exophthalmos degrees, so a duplicate description is omitted.

Meanwhile, one of the two time points for determining the trend in the thyroid ophthalmopathy severities is fixed and the other time point is allowed to be changed, so that the trend in the thyroid ophthalmopathy severities may also be determined. The description for the case where one of the two time points for determining the trend is fixed has been described above in the describing of the trend determination for exophthalmos degrees, so a duplicate description is omitted.

Meanwhile, information on an injection reaction after administering a medicine may be obtained on the basis of questionnaire survey content obtained from the patient 502.

To this end, the questionnaire survey content requested from the patient 502 may include questionnaire survey content on signs and/or symptoms following the injection reaction. For example, the questionnaire survey content about the signs and/or symptoms following the injection reaction may include questions about whether blood pressure increases or not, whether fever is present or not, whether tachycardia is present or not, whether dyspnea is present or not, whether headache is present or not, and/or whether muscle pain is present or not, but it is not limited thereto.

Meanwhile, the patient 502 may first be provided with information related to the injection reaction before being requested to fill out questionnaire survey content about signs and/or symptoms related to the injection reaction.

Specifically, in a case where the patient 502 visits the hospital 501 and is administered a medicine, a user device of the patient 502 may display information about what symptoms may appear in relation to the injection reaction. In this case, the information related to the injection reaction may be information stored in the user device of the patient 502 or information received from the analysis server 503.

Accordingly, the patient 502 may first recognize the information related to the injection reaction that may occur due to the medicine administration before the injection reaction occurs, so that the patient 502 is able to more easily cope with a case when an injection reaction occurs thereafter.

In the case of the injection reaction following the medicine administration, the time taken to occur may vary depending on each medicine. For example, in a case of a medicine for the purpose of treating thyroid ophthalmopathy, an injection reaction may occur within a time of 1.5 hours after administration, and such time may vary depending on clinical trial results for each medicine.

Accordingly, the time requested to the patient 502 for filling out questionnaire survey content on the injection reaction may vary depending on the characteristics of each medicine. For example, the patient 502 may be requested to fill out the questionnaire survey content about the infusion reaction 1.5 hours after receiving the medicine administration, and a time point of receiving the request is not limited to the example described above.

Meanwhile, since a time point at which an injection reaction occurs in each patient 502 may vary from patient to patient depending on each patient's characteristics, a patient 502 may also fill out the questionnaire survey content about the injection reaction before receiving a separate request to fill out the questionnaire survey content. This is not limited thereto, and even when the patient 502 does not have an injection reaction at the time point of being requested to fill out the questionnaire survey content about the injection reaction and thus does not fill out the questionnaire survey content, the patient may also be able to fill out the questionnaire survey content separately in a case where any injection reaction occurs at a later time.

Meanwhile, the time point at which the injection reaction occurs may be determined on the basis of the questionnaire survey content obtained from the patient 502. For example, the time point at which the injection reaction occurs may be determined on the basis of information about the time point at which the injection reaction occurs, the information being included in the questionnaire survey content. Alternatively, the time point at which the injection reaction occurs may be determined on the basis of the time point at which the questionnaire survey content is filled out, but this is not limited to the example described above.

A time interval between the time point at which the injection reaction occurs and the time point at which the medicine is administered may be stored as data of the patient 502. For example, the analysis server 503 may determine the time point at which the injection reaction occurs on the basis of the questionnaire survey content obtained from the patient 502, so as to determine the time interval with the time point at which the medicine is administered, thereby storing the determined time interval as patient data.

Meanwhile, the information about the injection reaction of the patient 502 and/or the information about the time interval between the time point at which the medicine is administered and the time point at which the injection reaction occurs may be provided to the hospital 501. For example, at a time point of obtaining the information about the injection reaction and/or the information about the time interval between the time point when the medicine is administered and the time point when the injection reaction occurs, the hospital 501 may be provided with the information about the injection reaction and/or the hospital 501 may be provided with the information about the time interval between the time point when the medicine is administered and the time point when the injection reaction occurs. This is not limited thereto, and at a time point at which the patient 502 visits the hospital 501, the hospital 501 may be provided with the information about the injection reaction and/or the hospital 501 may be provided with the information about the time interval between the time point when the medicine is administered and the time point when the injection reaction occurs.

Accordingly, the hospital 501 may administer a medicine to the patient 502 by considering the information about the infusion reaction, so as to more easily respond when the patient 502 experiences an infusion reaction.

Meanwhile, the patient's strabismus information may be obtained on the basis of a facial image and/or questionnaire survey content obtained from the patient 502. To this end, the questionnaire survey content requested from the patient 502 may include questionnaire survey content regarding whether strabismus is present or not.

Specifically, whether the patient has strabismus or not may be determined from the obtained facial image. Alternatively, whether the patient has strabismus or not may be determined on the basis of the patient's content of responses to strabismus-related questions included in the obtained questionnaire survey content.

According to the exemplary embodiment, the patient's personalized estimates and patient data may be displayed to the patient 502 or provided to the hospital 501.

Specifically, referring back to FIG. 5, the analysis server 503 may perform displaying 524 of the patient's 502 determined personalized estimates to the patient 502 and perform providing 525 the patient's 502 determined personalized estimates and the obtained patient data to the hospital 501.

More specifically, the patient's personalized estimates may be provided to and displayed on the user device of the patient 502, and the patient's personalized estimates and/or patient data may be provided to and displayed on the medical staff device and/or hospital server of the hospital 501. Hereinafter, displaying the patient's personalized estimates and/or patient data to the patient may be understood as displaying it on the patient's user device, and providing and displaying the patient's personalized estimates and/or patient data to and on the hospital may be understood as providing and displaying it to and on the medical staff device and/or hospital server of the hospital.

Meanwhile, in FIG. 5, it is illustrated that the patient's personalized estimates are displayed to the patient 502 at a first monitoring time point 520, but the time point at which the patient's personalized estimates are displayed to the patient 502 is not limited to the first monitoring time point 520. For example, the patient 502 may check the patient's personalized estimates without having to capture a facial image or fill out questionnaire survey content. Specifically, the user device of the patient 502 may display the patient's personalized estimates obtained from the analysis server 503 at any time point desired by the patient 502.

Meanwhile, in FIG. 5, it is illustrated that the hospital 501 receives the patient's personalized estimates and patient data at the first monitoring time point 520, but the time point at which the hospital 501 receives the patient's personalized estimates and/or patient data is not limited to the first monitoring time point 520. For example, the hospital 501 may be provided with the patient's personalized estimates and/or patient data without the patient 502 having to capture the facial image and fill out questionnaire survey content. Specifically, the medical staff device and/or hospital server of the hospital 501 may receive the patient's personalized estimates and/or patient data from the analysis server 503 at any time point desired by the medical staff. As another example, the hospital 501 may be provided with the patient's personalized estimates and/or patient data at a time point at which the patient 502 visits the hospital 501. In addition, the hospital 501 may also be provided with the patient's personalized estimates and/or patient data even at a time point at which the patient 502 does not visit the hospital 501.

Hereinafter, a method for displaying a patient's personalized estimates is described.

Figure 7:
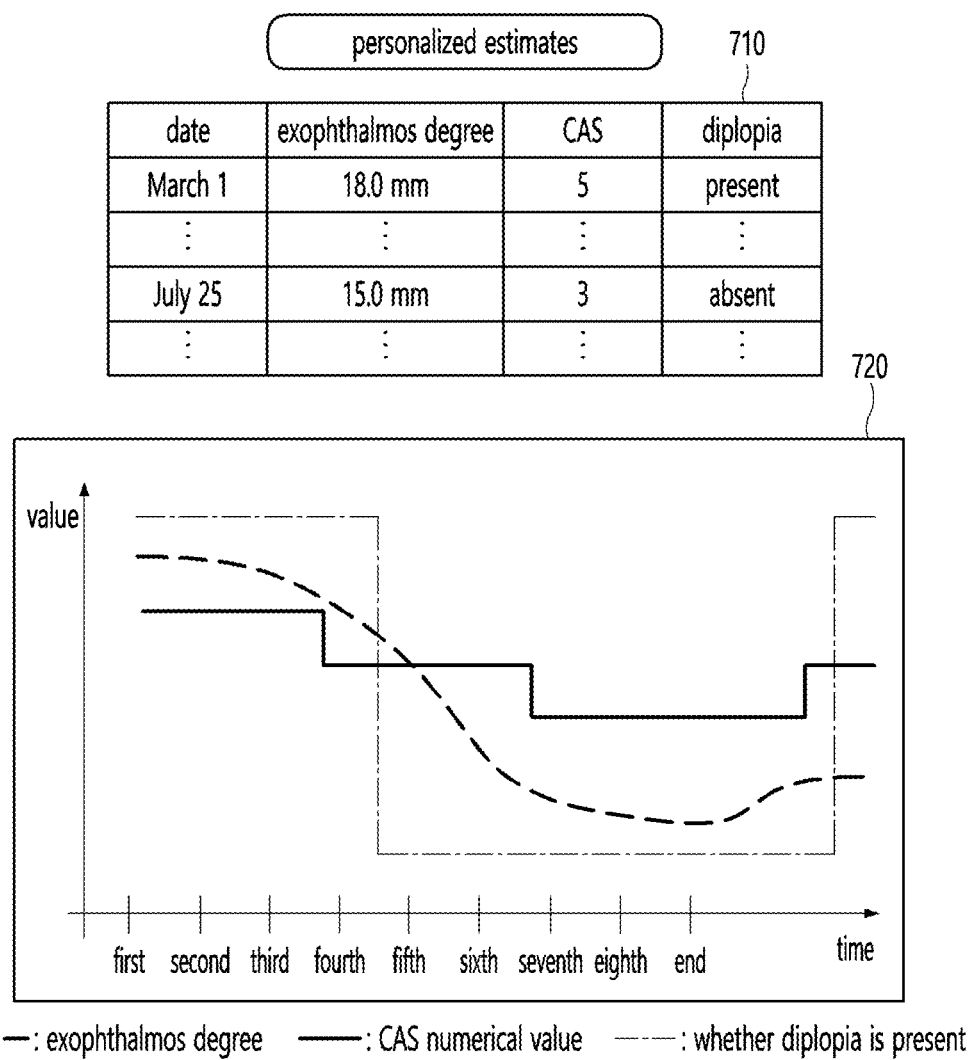
FIG. 7 is a view illustrating a user interface (UI) for displaying a patient's personalized estimates according to the exemplary embodiment.

FIG. 7 is a view illustrating a user interface (UI) for displaying the patient's personalized estimates according to the exemplary embodiment.

According to the exemplary embodiment, the patient's personalized estimates obtained may be displayed as time-series data. The time-series data may mean data arranged in time series.

For example, referring to FIG. 7, the patient's personalized estimates obtained may be displayed in a time-series data table 710 distinguished by date. The time-series data table 710 may include information by date on exophthalmos numerical values, CAS numerical values, and/or whether the patient has diplopia. In addition, although not shown in FIG. 7, the time-series data table may include information by date on eyelid retraction numerical values and/or thyroid ophthalmopathy severities.

Meanwhile, in the data table 710 in FIG. 7, the patient's personalized estimates are displayed as values itself by date, but it is not limited thereto, and the patient's personalized estimates may also be displayed as a trend by date. In this case, the trend by date may mean a change trend up to that date.

Specifically, the data table 710 in FIG. 7 includes, by date, values itself on exophthalmos degrees, CAS numerical values, and whether diplopia is present or not, but the data table may include, by date, a trend in the exophthalmos degrees, a trend in the CAS, and/or a trend in the diplopia. This is not limited thereto, and the data table may also include, by date, a trend in eyelid retraction and/or a trend in thyroid ophthalmopathy severities.

More specifically, for exophthalmos degree items, these items may be indicated as alleviated, worsened, or unchanged, rather than numerically, and may be indicated as decreased, increased, or unchanged, but it is not limited thereto. In addition, for CAS items, these items may be indicated as alleviated, worsened, or unchanged, rather than numerically, and may be indicated as decreased, increased, or unchanged, but it is not limited thereto. In addition, for diplopia items, these items may be indicated as alleviated, worsened, or unchanged, rather than present or absent. In addition, for eyelid retraction items, these items may be indicated as alleviated, worsened, or unchanged, rather than numerically, and may be indicated as decreased, increased, or unchanged, but it is not limited thereto. In addition, for thyroid ophthalmopathy severity items, these items may be indicated as alleviated, worsened, or unchanged, rather than none, mild (moderate), or severe (serious), but it is not limited thereto.

Meanwhile, as another example, referring to FIG. 7, the patient's personalized estimates obtained may be displayed in a time-series data graph 720. The time-series data graph may mean a graph that displays data arranged in time series.

The time-series data graph 720 may include exophthalmos numerical values, CAS numerical values, and/or values for whether the patient has diplopia, which are obtained over time. In addition, although not shown in FIG. 7, the time-series data graph may include eyelid retraction numerical values and/or values of thyroid ophthalmopathy severity, which are obtained over time.

Meanwhile, in the data graph 720 in FIG. 7, the patient's personalized estimates are displayed as one graph, but it is not limited thereto, and the patient's personalized estimates may also be displayed as separate graphs.

Specifically, in the graph 720 in FIG. 7, the exophthalmos numerical values, the CAS numerical values, and the values of whether the patient has diplopia, which are obtained over time, are displayed as one graph 720, but it is not limited thereto, and each of a graph of exophthalmos numerical values over time, a graph of CAS numerical values over time, and/or a graph of values for whether the patient has diplopia, which are obtained over time, may be displayed. In addition, each of a graph of eyelid retraction numerical values over time and/or a graph of values for thyroid ophthalmopathy severities over time may also be displayed.

Meanwhile, in the data graph 720 in FIG. 7, the patient's personalized estimates are displayed as values as it is, but it is not limited thereto, and the patient's personalized estimates may also be displayed as values in a smoothed form.

Figure 8:
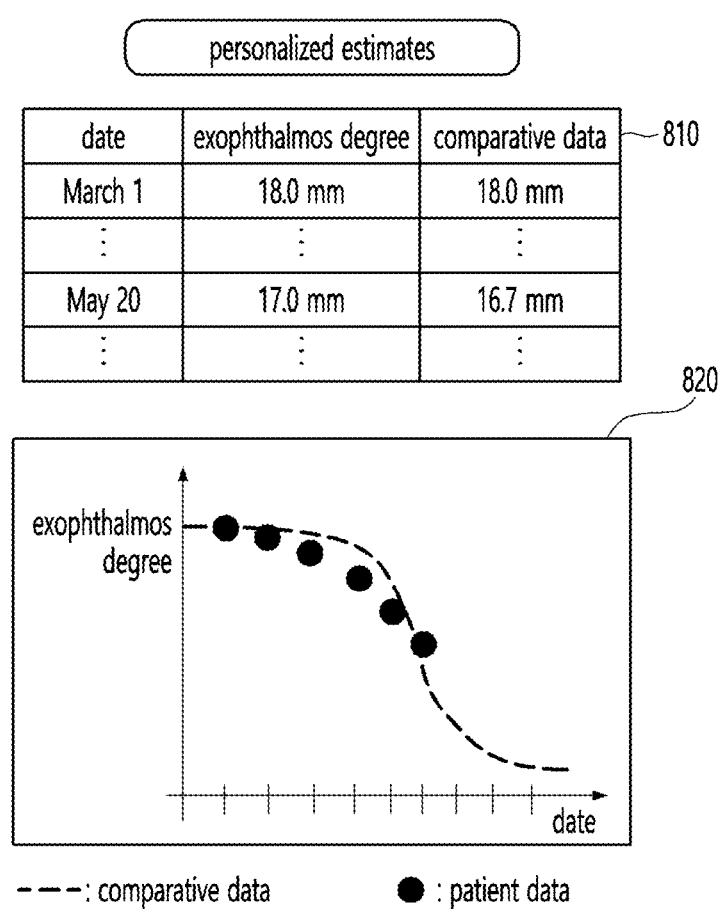
FIG. 8 is a view illustrating a UI for displaying the patient's personalized estimates according to the exemplary embodiment.

FIG. 8 is a view illustrating a UI for displaying the patient's personalized estimates according to the exemplary embodiment.

According to the exemplary embodiment, the patient's personalized estimates obtained may be displayed together with comparative data.

The comparative data may mean expectation data regarding the expected effectiveness of medicine.

Specifically, the comparative data may be obtained on the basis of clinical trial results.

More specifically, the comparative data may be obtained on the basis of average value data of the subjects' condition changes according to the effectiveness of medicine included in the clinical trial results. In this case, the average value data of the subjects' condition changes may mean standard data.

More specifically, the comparative data may be obtained by adjusting the standard data according to the patient's personalized estimates. For example, the comparative data may be obtained by calculating a difference value between an initial value on the standard data and an initial value of the patient's personalized estimates, and adding the calculated difference value to the standard data. Specifically, the comparative data may be obtained by adding the calculated difference value to each time-series value included in the standard data.

The comparative data on exophthalmos degrees may be obtained on the basis of average value data of the subject's exophthalmos numerical values over time included in the clinical trial results. In this case, the average value data of the subjects' exophthalmos numerical values over time may mean standard data for exophthalmos degrees.

Specifically, the comparative data on exophthalmos degrees may be obtained by adjusting the standard data on exophthalmos degrees according to an exophthalmos numerical value included in the patient's personalized estimate. For example, the comparative data for exophthalmos degrees may be obtained by calculating a difference value between an initial value on the standard data for exophthalmos degrees and an initial value of the exophthalmos numerical value included in the patient's personalized estimate and adding the calculated difference value to the standard data for exophthalmos degrees. For a more specific example, in a case where an initial value on the standard data for exophthalmos degrees is 17.0 mm and an initial value of an exophthalmos numerical value included in the patient's personalized estimate is 18.0 mm, a difference value is +1 mm, so the comparative data for exophthalmos degrees may be obtained by adding +1 mm to the standard data for exophthalmos degrees. Specifically, the comparative data on the exophthalmos degrees may be obtained by adding the calculated difference value to each of the time-series exophthalmos numerical values included in the standard data on exophthalmos degrees. Meanwhile, the specific numerical values are not limited to the example described above.

This is not limited thereto, and the comparative data may be obtained on the basis of average value data of a slope of changes in the subjects' exophthalmos numerical values over time included in the clinical trial results.

Referring to FIG. 8, the patient's obtained personalized estimates may be displayed in a time-series data table 810 distinguished by date together with the comparative data. The time-series data table may mean a table that displays data arranged in time series. Specifically, the time-series data table may display the patient's personalized estimates and comparative data such that dates in which the patient's personalized estimates are obtained respectively correspond to dates in the comparative data in order.

This is not limited thereto, and the patient's personalized estimates obtained may be displayed as a time-series data graph 820 together with the comparative data. The time-series data graph may mean a graph that displays data arranged in time series. Specifically, the time-series data graph may display the patient's personalized estimates and comparative data such that dates of the patient's obtained personalized estimates respectively correspond to dates in the comparative data in order.

The patient's personalized estimates obtained may be displayed together with the comparative data, so that whether the patient's condition is improving or not may be confirmed through the data.

Meanwhile, in FIG. 8, the exophthalmos numerical values are displayed as comparative data, but it is not limited thereto, and a change slope of the exophthalmos numerical values may be displayed as comparative data. In this case, the patient's personalized estimates may be displayed as the change slope of the exophthalmos numerical values.

Meanwhile, in FIG. 8, only the comparative data on exophthalmos degrees is shown, but it is not limited thereto, and the comparative data may include comparative data on CAS numerical values and/or whether the patient has diplopia. The method for obtaining comparative data on CAS numerical values and/or whether the patient has diplopia may be applied in a similar manner to the method for obtaining comparative data on exophthalmos degrees, so a duplicate description is omitted.

Meanwhile, although not shown in FIG. 8, the patient's personalized estimates obtained may be displayed together with an average value of the exophthalmos degrees of a group to which the patient belongs.

The group to which the patient belongs may be distinguished by gender and/or age. For example, patients of the same gender may be recognized as belonging to the same group. As another example, patients who fall within the same age range among preset age ranges may be recognized as belonging to the same group. For a yet another example, patients of the same race may be recognized as belonging to the same group, and each group to which the patients belongs is not limited to the examples described above.

The patient's personalized estimates obtained may be displayed together with the average value of the exophthalmos degrees of the group to which the patient belongs, so that the patient and/or the medical staff may check how the patient's condition differs from this average value.

Whether a medicine is effective or not may be determined on the basis of the patient's personalized estimates obtained according to the exemplary embodiment.

Specifically, whether the medicine is effective or not may be determined in cases where an exophthalmos numerical value decreases, a CAS numerical value decreases, and/or diplopia improves, which are included in the patient's personalized estimates obtained.

Alternatively, whether the medicine is effective or not may be determined in cases where a trend in the exophthalmos degrees decreases, a trend in CAS decreases, and/or a trend in diplopia decreases, which are included in the patient's personalized estimates obtained.

Whether the medicine is effective or not may be determined at each of monitoring time points. That is, at each monitoring time point, whether the patient's condition is a condition in which the medicine is effective may be determined.

This is not limited thereto, and whether the medicine is effective or not may be determined throughout the entire medicine administration process. That is, according to medicine administration, it may be determined whether or not the patient's current condition is a condition where the medicine is effective.

The determined results on whether the medicine is effective or not may be displayed together with the patient's personalized estimates obtained. This is not limited thereto, and only the results on whether the medicine is effective or not may be displayed separately.

A treatment score for a patient may be determined on the basis of the patient's personalized estimates obtained according to the exemplary embodiment.

The treatment score is a numerical score that indicates how well a treatment is effective for a current patient. The treatment score may range from 0 to 100 points, but a score range thereof is not limited thereto.

Specifically, the treatment score may be determined to be a high score in cases where an exophthalmos numerical value decreases, a CAS numerical value decreases, and/or diplopia improves, which are included in the patient's personalized estimates obtained. More specifically, the treatment score may be determined to be higher as the exophthalmos numerical value decreases more, the CAS numerical value decreases more, and/or the diplopia improves more, which are included in the patient's personalized estimated obtained.

Alternatively, the treatment score may be determined to be a high score in cases where a trend in exophthalmos degrees decreases, a trend in CAS numerical values decreases, and/or a trend in the diplopia decreases, which are included in the patient's personalized estimated obtained The treatment score for the patient may be determined at each of monitoring time points. That is, whether or not the treatment is well-effective for the patient may be expressed numerically at each monitoring time point.

This is not limited thereto, and the treatment score for the patient may be determined throughout the entire course of medicine administration. That is, whether or not a current treatment is well-effective for the patient according to the medicine administration may be determined.

The determined treatment score may be displayed together with the patient's personalized estimates obtained. This is not limited thereto, and only the treatment score may also be displayed separately.

Referring back to FIG. 5, the hospital 501 may also be provided with patient data together with the patient's personalized estimates. Specifically, the hospital 501 may also receive the patient data 525 together with the patient's 502 personalized estimates from the analysis server 503.

The patient data provided to the hospital 501 by the analysis server 503 may include: patient data obtained, by the hospital 501, as actual measured patient data when the patient 502 visits the hospital and which is transmitted to the analysis server 503; injection reaction information obtained on the basis of questionnaire survey content obtained from the patient 502; thyroid dysfunction management history of the patient 502; thyroid ophthalmopathy treatment information of the patient 502; and/or questionnaire survey content obtained from the patient 502. This is not limited thereto, and the patient data provided to the hospital 501 by the analysis server 503 may include various types of patient data described above as the patient data.

Meanwhile, in FIG. 5, it is illustrated that the hospital 501 receives the patient's personalized estimates and patient data at the first monitoring time point 520, but the time point at which the hospital 501 receives the patient's personalized estimates and/or patient data is not limited to the first monitoring time point 520. For example, the hospital 501 may be provided with the patient's personalized estimates and/or patient data at a time point at which the patient 502 visits the hospital 501. In addition, the hospital 501 may also be provided with the patient's personalized estimates and/or patient data even at a time point at which the patient 502 does not visit the hospital 501.

Meanwhile, according to the exemplary embodiment, the patient's facial image obtained may be displayed to the patient and/or the hospital in the form of comparative data so that a process of changes over time may be easily confirmed, and a method for displaying a facial image is specifically described later in 9. Displaying facial image comparative data.

Meanwhile, the patient 502 and/or the hospital 501 may be provided with a message and/or additional data on the basis of the patient's personalized estimates obtained.

Specifically, the patient 502 and/or the hospital 501 may be provided with the message and/or additional data in cases where an exophthalmos numerical value included in the patient's obtained personalized estimate increases by 1 mm or more, 2 mm or more, 3 mm or more, 4 mm or more, 5 mm or more, 6 mm or more, 7 mm or more, 8 mm or more, 9 mm or more, 10 mm or more, or 11 mm or more.

Preferably, in a case where an exophthalmos numerical value included in the patient's personalized estimate obtained increases by 2 mm or more, the patient 502 and/or the hospital 501 may be provided with the message and/or additional data.

Meanwhile, in a case where a CAS numerical value included in the patient's personalized estimate obtained is less than three points and then becomes three points or more, the patient 502 and/or the hospital 501 may be provided with a message and/or additional data.

Meanwhile, in a case where the CAS numerical value included in the patient's personalized estimate obtained increases by two points or more, the patient 502 and/or the hospital 501 may be provided with a message and/or additional data. In the case of CAS numerical values, depending on the patient's condition, the patient may also temporarily experience redness of eyelid, redness of conjunctiva, swelling of eyelid, swelling of conjunctiva, swelling of lacrimal caruncle, spontaneous retrobulbar pain, or pain on attempted upward or downward gaze. Therefore, it may be preferable for the patient 502 and/or the hospital 501 to be provided with the message and/or additional data in a case where the CAS numerical value increases by two points or more, rather than by one point or more.

Meanwhile, specific numeric values for the exophthalmos numerical value and CAS numerical value are not limited to the examples described above.

In relation to obtaining the message and/or additional data of the patient 502 and/or hospital 501, specifically, the patient 502 may obtain a message for suggesting a hospital visit, and the hospital 501 may obtain a warning message regarding the patient's condition.

More specifically, the message for suggesting a hospital visit may be displayed on the user device of the patient 502, and the warning message may be displayed on the medical staff device and/or medical server of the hospital 501, but it is not limited thereto.

Side effects may also occur when administering a medicine, and in some cases, rapid actions may be required. Therefore, whether side effects occur or not in the patient may also be monitored during treatment process monitoring.

Specifically, information regarding the side effects may also be obtained from the patient during the treatment process monitoring.

Side effect-related information to be obtained from the patient may be determined on the basis of clinical trial results of a medicine. For example, information related to side effects may include: whether muscle cramps are present or not, whether nausea is present or not, whether hair loss is present or not, whether diarrhea is present or not, whether fatigue is present or not, and/or whether hyperglycemia is present or not, and the information related to the side effects may vary from medicine to medicine.

Meanwhile, the information related to the side effects may be obtained on the basis of questionnaire survey content requested from a patient. Specifically, the questionnaire survey content that the patient is requested to fill out may include questionnaire survey content about signs and/or symptoms associated with the side effects. Since each medicine may have different side effects, the questionnaire survey content requested from the patient may be determined on the basis of which medicine the patient is administered.

Meanwhile, the patient may be provided with the information related to the side effects before being requested to fill out the questionnaire survey content related to the side effects.

Based on the information related to the side effects obtained from the patient, the patient and/or the hospital may be provided with a message and/or additional data.

The message and/or additional data provided to the patient and/or hospital may be determined on the basis of action details in accordance with side effects described in a medication manual for a medicine.

For example, in a case where the patient is determined to have experienced side effects on the basis of the information related to the side effects obtained from the patient, the patient may be provided with a message for suggesting a phone call to an administrative agency and/or regulatory agency responsible for managing the safety of medical supplies. In this case, the message may include the phone numbers of the administrative agency and/or regulatory agency that are responsible for managing the safety of medical supplies.

Alternatively, the patient may be provided with a message for suggesting access to Internet sites of the administrative agency and/or regulatory agency that manage the safety of medical supplies. In this case, the message may include the Internet addresses of websites of the administrative agency and/or regulatory agency that are responsible for managing the safety of medical supplies.

Alternatively, the patient may be provided with a message for suggesting a phone call to the hospital. In this case, the hospital may be a hospital where the patient is visiting and/or has visited, and the message may include a phone number of the hospital.

Alternatively, the patient may be provided with a message for suggesting access to the Internet site of the hospital. In this case, the hospital may be a hospital where the patient is visiting and/or has visited, and the message may include the Internet address of a website of the hospital.

Meanwhile, the hospital may be provided with a message for warning the patient that side effects have occurred, and may be provided with information related to the side effects, as additional data.

5. Facial Image-Based Exophthalmos Degree Determination Method

An exophthalmos degree is an indicator of how much an eyeball protrudes, and may be determined by a vertical distance between a corneal apex and a lateral orbital rim. That is, the exophthalmos degree is the vertical distance between the corneal apex and the lateral orbital rim, so it is previously difficult to determine the exophthalmos degree by using only a single front facial image.

However, according to exemplary embodiment of the present disclosure, an exophthalmos degree may be estimated by using a single front facial image. The specific method for estimating the exophthalmos degree is described below.

Meanwhile, a facial image may be obtained from a patient. Specifically, the facial image may be obtained from the patient's user device, and the facial image may be an image captured by the patient's user device. It is not limited to thereto, and a facial image may also be obtained from a hospital. Specifically, the facial image may be obtained by allowing medical staff assigned at the hospital to capture the patient's face when the patient visits the hospital.

The facial image may be an image of an area between the lower end of a nose and the upper end of an eyebrow. This is not limited thereto, and the facial image may mean an image that shows an eye region.

(1) Facial Image-Based Exophthalmos Degree Determination Method—1

In order to estimate an exophthalmos degree from a facial image, a three-dimensional (3D) facial landmark model trained may first be applied on facial images.

In this case, the facial images may be images including: a front facial image, facial images taken from angles different from each other, a panoramic face image, and/or video capturing a face.

The 3D facial landmark detection model is a model trained to predict 3D landmark coordinates from a facial image. Specifically, the 3D facial landmark detection model is a model trained to predict not only the x-axis and y-axis coordinates but also the z-axis coordinate of each of landmarks, i.e., each of feature points of a facial image, and may be a model trained by using, as a training data set, the facial image and the 3D coordinate values corresponding to the landmarks shown in the facial image. In this case, the x-axis may mean the horizontal axis of a two-dimensional (2D) image, the y-axis may mean the vertical axis of the 2D image, and the z-axis may mean the axis in a direction perpendicular to the x and y axes of the 2D image.

Meanwhile, the 3D facial landmark detection model according to the present disclosure may be a model configured to detect, from a facial image, landmarks positioned at a boundary between an eyeball and an eyelid and landmarks positioned at the outer edge of a pupil.

Accordingly, by applying a front facial image to the 3D facial landmark detection model, it is possible to obtain not only 3D coordinates of the landmarks positioned at the boundary between the eyeball and the eyelid but also 3D coordinates of the landmarks positioned at the outer edge of the pupil, the landmarks appearing in the front facial image.

Figure 9:
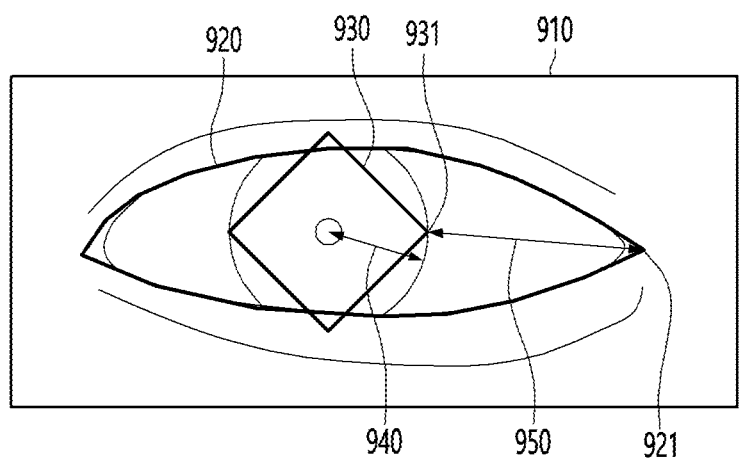
FIG. 9 is a view illustrating a method for estimating an exophthalmos degree from landmarks detected from a front facial image.

FIG. 9 is a view illustrating a method for estimating an exophthalmos degree from landmarks detected from a front facial image.

As illustrated in FIG. 9, by applying the 3D facial landmark detection model to the facial image 910, the landmarks positioned at the boundary between the eyeball and the eyelid may be detected. FIG. 9 illustrates a line 920 connecting the landmarks positioned at the boundary between the eyeball and the eyelid.

In addition, as illustrated in FIG. 9, by applying the 3D facial landmark detection model to the facial image 910, the landmarks positioned at the outer edge of the pupil may be detected. FIG. 9 illustrates a line 930 connecting the landmarks positioned at the outer edge of the pupil. The landmarks positioned at the outer edge of the pupil are positioned at the top, left, right, and bottom of the pupil, so the line 930 connecting the landmarks positioned at the outer edge of the pupil is illustrated in a square shape.

Among the landmarks detected from the facial image, it is possible to obtain a z-axis length between a landmark 931 positioned at the outer edge of the pupil and a landmark 921 positioned at the outer corner of the eye. In this case, the z-axis length may be calculated as a pixel distance.

A distance 940 corresponding to a radius of the pupil may be calculated from the facial image 910. In this case, the distance 940 corresponding to the radius of the pupil may be calculated as a pixel distance.

An actual length of a radius of a pupil is generally similar among people of the same type. Specifically, the actual length of the radius of the pupil may be 5.735 mm for men and 5.585 mm for women. Meanwhile, the actual length of the radius of the pupil may vary depending on people's race and/or age.

Since the actual length of the radius of the pupil is similar among people of the same type, it is possible to predetermine an actual length of a radius of a pupil, which is differentiated by gender, race, and/or age.

Accordingly, the actual length of the radius of the pupil corresponding to the facial image 910 may be obtained from the actual length of the radius of the pupil predetermined on the basis of the patient's gender, race, and/or age included in patient data.

An actual z-axis distance may be calculated by using a pixel distance corresponding to a radius of a pupil, an actual distance of the radius of the pupil, and a z-axis pixel distance.

Specifically, resolution of a pixel distance may be determined on the basis of a ratio of the pixel distance corresponding to the radius of the pupil and the actual distance of the radius of the pupil. The actual z-axis distance may be calculated by applying the determined resolution to the z-axis pixel distance.

Meanwhile, the calculated actual z-axis distance is a vertical distance from the outer edge of the pupil to the outer corner of the eye, so an estimation value of an exophthalmos degree may be calculated by adding, to the calculated actual z-axis distance, a vertical actual distance from a center position of pupil and iris to the outer edge of the pupil.

Meanwhile, it is generally true that the actual vertical distance from the center position of pupil and iris to the outer edge of the pupil is similar for each person. Specifically, an actual vertical distance from a center position of pupil and iris to the outer edge of a pupil may generally be between 0.2 mm and 0.3 mm.

Accordingly, the estimation value of the exophthalmos degree may be calculated by adding 0.25 mm, which is an average value of 0.2 mm and 0.3 mm, to the calculated actual z-axis distance.

Meanwhile, the actual vertical distance from the center position of pupil and iris to the outer edge of the pupil may be measured by the medical staff when the patient visits the hospital, and may also be used to estimate an exophthalmos degree, but it is not limited thereto.

(2) Facial Image-Based Exophthalmos Degree Determination Method—2

An exophthalmos degree may be predicted by inputting feature values obtainable from a facial image into a trained exophthalmos degree prediction model.

The exophthalmos degree prediction model may be a model trained by using training data that includes, as input data, feature values obtainable from a facial image and that includes, as a label value, an exophthalmos numerical value corresponding to the facial image.

The exophthalmos degree prediction model may be a regression model, a neural network model, a machine learning model, a deep learning model, or a combination thereof. For example, the exophthalmos degree prediction model may be a Linear Regression model, a Polynomial Regression model, a Ridge Regression model, a Lasso Regression model, a Support Vector Machines (SVM) model, a Decision Tree Regression model, a Random Forest Regression model, a K-Nearest Neighbors (KNN) model, a Feedforward Neural Networks model, a Convolutional Neural Networks (CNNs) model, a Recurrent Neural Networks (RNNs) model, a Long Short-Term Memory (LSTM) networks model, a Gated Recurrent Units (GRUs) model, a Gradient Boosting (e.g., XGBoost, LightGBM, and CatBoost) model, or an AdaBoost model, but it is not limited thereto.

The exophthalmos degree prediction model may be trained through various methods such as supervised training, unsupervised training, reinforcement training, and imitation training.

For example, the exophthalmos degree prediction model may be trained through the supervised learning. In this case, the exophthalmos degree prediction model may be trained by using feature values obtainable from a facial image and an exophthalmos numerical value corresponding to the facial image. For a more specific example, the exophthalmos degree prediction model may receive, as input, the feature values obtainable from the facial image and output an exophthalmos degree prediction value, and the exophthalmos degree prediction model may be trained on the basis of a difference between the output exophthalmos degree prediction value and the output exophthalmos numerical value corresponding to the facial image.

Feature values obtainable from a facial image may include: a z-axis length value between a landmark located at the outer edge of a pupil and a landmark located at the outer corner of an eye, the landmarks being obtained by applying a 3D facial landmark detection model to the facial image (hereinafter referred to as the z-axis length value); a value of an angular-specific distance (Multiple Radial Mid-Pupil Lid Distance or Multiple Radial MPLD) from a center position of pupil and iris the face image to a boundary between an eyeball and an eyelid (hereinafter referred to as a Radial MPLD value); a sum of a distance value corresponding to 0 degrees and a distance value corresponding to 180 degrees among the Radial MPLD values (hereinafter referred to as a 0-to-180 distance value); a distance value corresponding to 90 degrees among the Radial MPLD values; a distance value corresponding to 270 degrees among the Radial MPLD values; a sum of the distance value corresponding to 90 degrees and the distance value corresponding to 270 degrees among the Radial MPLD values (hereinafter referred to as a 90-to-270 distance value); a horizontal length of the eye connecting the leftmost and rightmost points of an eye region (hereinafter referred to as the eye horizontal length); a distance between a straight line indicating the eye horizontal length and the center position of pupil and iris (hereinafter referred to as the distance between the eye horizontal length and the center position); a vertical length of the eye connecting the uppermost and lowermost points of the eye area (hereinafter referred to as the eye vertical length); and a distance between a straight line representing the eye vertical length and the center position of pupil and iris (hereinafter referred to as the distance between the eye vertical length and the center position).

Among the feature values obtainable from the facial image, the z-axis length values between the landmarks positioned at the outer edge of the pupil and the landmark positioned at the outer corner of the eye, the landmarks being obtained by applying the 3D facial landmark detection model to the facial image, may be obtained from images including: the front facial image, the facial images taken from different angles, the panorama facial image, and/or the video capturing the face. The specific method for obtaining the z-axis length values has been described above in (1) Facial image-based exophthalmos degree determination method—1, so a duplicate description is omitted.

Meanwhile, in order to obtain other feature values from the facial image, an image segmentation model trained on front facial images may first be applied.

The image segmentation model may be an artificial neural network model trained to identify an object shown in an image and detect an area of the object in the image. The image segmentation model is a model commonly used to detect a specific object area from an image, so a detailed description of the structure of the image segmentation model is omitted.

Meanwhile, the image segmentation model according to the present disclosure may be a model that detects an eyeball area and a pupil and iris area, which are included in a front facial image.

By applying the front facial image to the image segmentation model, the eyeball area and pupil and iris area shown in the front facial image may be detected.

Figure 10:
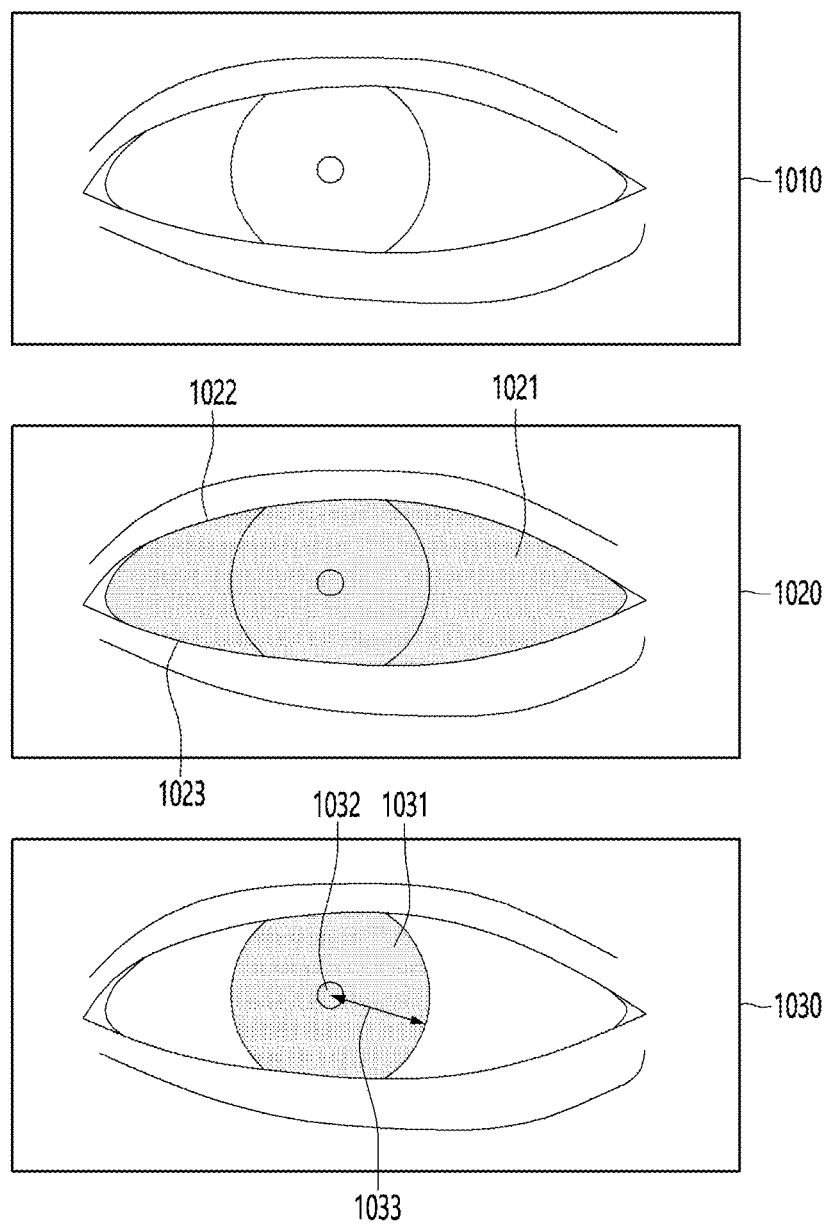
FIG. 10 is a view illustrating an eyeball area and pupil and iris area, which are detected from the front facial image.

FIG. 10 is a view illustrating an eyeball area and pupil and iris area, which are detected from a front facial image.

As illustrated in FIG. 10, a front facial image 1020 in which an eyeball area 1021 is detected and a front facial image 1030 in which a pupil and iris area 1031 is detected may be obtained by applying the image segmentation model to a front facial image 1010.

In FIG. 10, the eyeball area 1021 is illustrated as not including a lacrimal caruncle area, but the segmentation model may also detect the lacrimal caruncle area as the eyeball area 1021.

Meanwhile, the segmentation model used to detect the eyeball area and the segmentation model used to detect the pupil and iris area may be models different from each other. Specifically, the segmentation model used to detect the eyeball area and the segmentation model used to detect the pupil and iris area may be separate segmentation models that are trained by using training data sets different from each other. In this case, before the segmentation model used to detect the eyeball area and the segmentation model used to detect the pupil and iris area are trained, the structures of these segmentation models may be identical to each other. Alternatively, before the segmentation model used to detect the eyeball area and the segmentation model used to detect the pupil and iris area are trained, the structures of these segmentation models may also be different from each other.

Meanwhile, the image segmentation model may be a single segmentation model trained to detect both of the eyeball area and the pupil and iris area.

Eyeball and eyelid boundaries 1022 and 1023 may be identified on the basis of the detected eyeball area 1021. Specifically, the boundary 1022 between the eyeball and the upper eyelid may mean an upper boundary of the eyeball area 1021, and the boundary 1023 between the eyeball and the lower eyelid may mean a lower boundary of the eyeball area 1021.

A center position of pupil and iris 1032 may be identified on the basis of the detected pupil and iris area 1031. Specifically, the center position of pupil and iris may be a center position of a circle corresponding to the detected pupil and iris area 1031.

Distances from the identified center position of pupil and iris 1032 to both of the eyeball and eyelid boundaries 1022 and 1023 may be calculated.

Specifically, Radial MPLD values from the identified center position of pupil and iris 1032 to both of the eyeball and eyelid boundaries 1022 and 1023 may be calculated. In this case, each distance value may be calculated as a pixel distance.

Meanwhile, a pixel distance corresponding to a pupil radius 1033 may be calculated on the basis of the detected pupil and iris area 1031.

Figure 11:
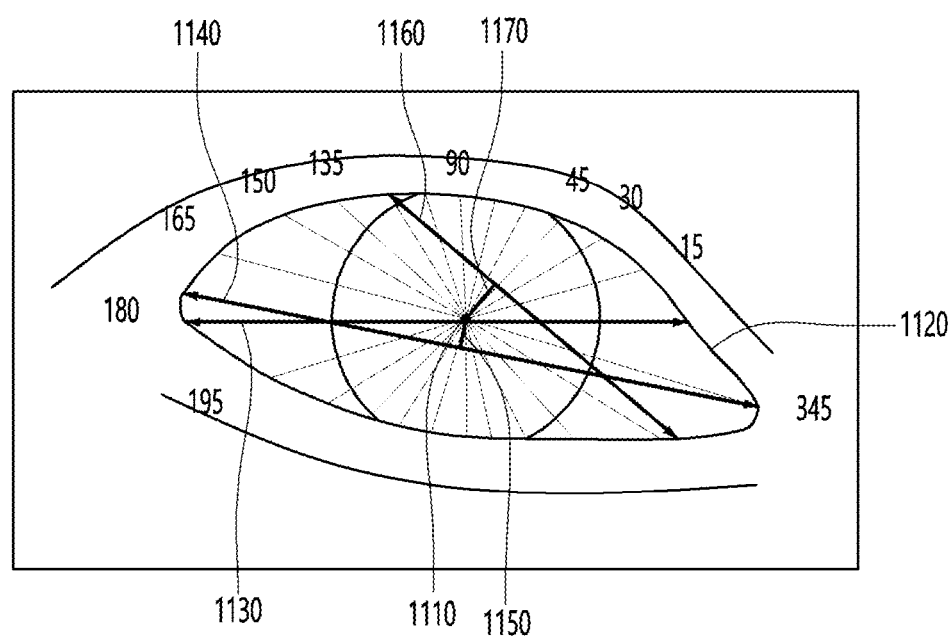
FIG. 11 is a view illustrating feature values obtainable from a facial image.

FIG. 11 is a view illustrating feature values obtainable from a facial image.

Referring to FIG. 11, in order to obtain Radial MPLD values from a center position of pupil and iris 1110 to a boundary 1120 between an eyeball and an eyelid on the facial image among feature values, the angles from the center position of pupil and iris 1110 to the boundary 1120 between the eyeball and the eyelid may be distinguished in 15-degree units while the x-axis direction of the image is set to 0 degrees, whereby a Radial MPLD value may be calculated for each distinguished angle. In this case, a direction for 0 degrees may be a direction toward a lacrimal caruncle from the center position of pupil and iris 1110 on the facial image.

Meanwhile, a Radial MPLD value for each angle is calculated while setting the x-axis direction of the image to 0 degrees, so the facial image is required to be aligned horizontally before the Radial MPLD value for each angle is calculated. In order to align the horizontal level of the facial image, the center position of pupil and iriss of both eyes on the facial image are determined, and the horizontal level of the image may be adjusted so that a straight line connecting the center position of pupil and iriss of both of the eyes becomes horizontal.

Among feature values obtainable from a facial image, feature values corresponding to Radial MPLD values may be determined as feature values for all the values of respective angles of the Radial MPLD values, but as for the feature values corresponding to the Radial MPLD values, one value obtained from the values of respective angles of the Radial MPLD values may also be determined as a feature value.

For example, feature values corresponding to Radial MPLD values may be determined and settled on the basis of the correlation of values for respective angles of the Radial MPLD values.

For another example, feature values corresponding to Radial MPLD values may be obtained by inputting values for respective angles of the Radial MPLD values into a value extraction model provided separately. The value extraction model may be a model trained to output a single feature value from a plurality of input values.

Among the feature values obtainable from the facial image, a sum 1130 of a distance value corresponding to 0 degrees and a distance value corresponding to 180 degrees in the Radial MPLD values may be obtained on the basis of the calculated Radial MPLD values.

Among the feature values obtainable from the facial image, a sum 1130 of a distance value corresponding to 90 degrees and a distance value corresponding to 270 degrees in the Radial MPLD values may be obtained on the basis of the calculated Radial MPLD values.

Among the feature values obtainable from the facial image, an eye horizontal length 1140 connecting the leftmost and the rightmost points of an eyeball area may be obtained on the basis of the eyeball area detected through the image segmentation model.

Among the feature values obtainable from the facial image, a distance 1150 between a straight line representing the eye horizontal length 1140 and a center position of pupil and iris 1110 may be obtained on the basis of the obtained eye horizontal length 1140 and center position of pupil and iris 1110.

Among the feature values obtainable from the facial image, an eye vertical length 1160 connecting the uppermost and the lowermost points of the eyeball area may be obtained on the basis of the eyeball area detected through the image segmentation model.

Among the feature values obtainable from the facial image, a distance between a straight line representing the eye vertical length 1160 and the center position of pupil and iris 1110 may be obtained on the basis of the eye vertical length 1160 obtained and the center position of pupil and iris 1110.

An exophthalmos degree may be determined on the basis of an output value obtained by inputting the feature values obtained from the facial image into the trained exophthalmos degree prediction model.

Figure 12:
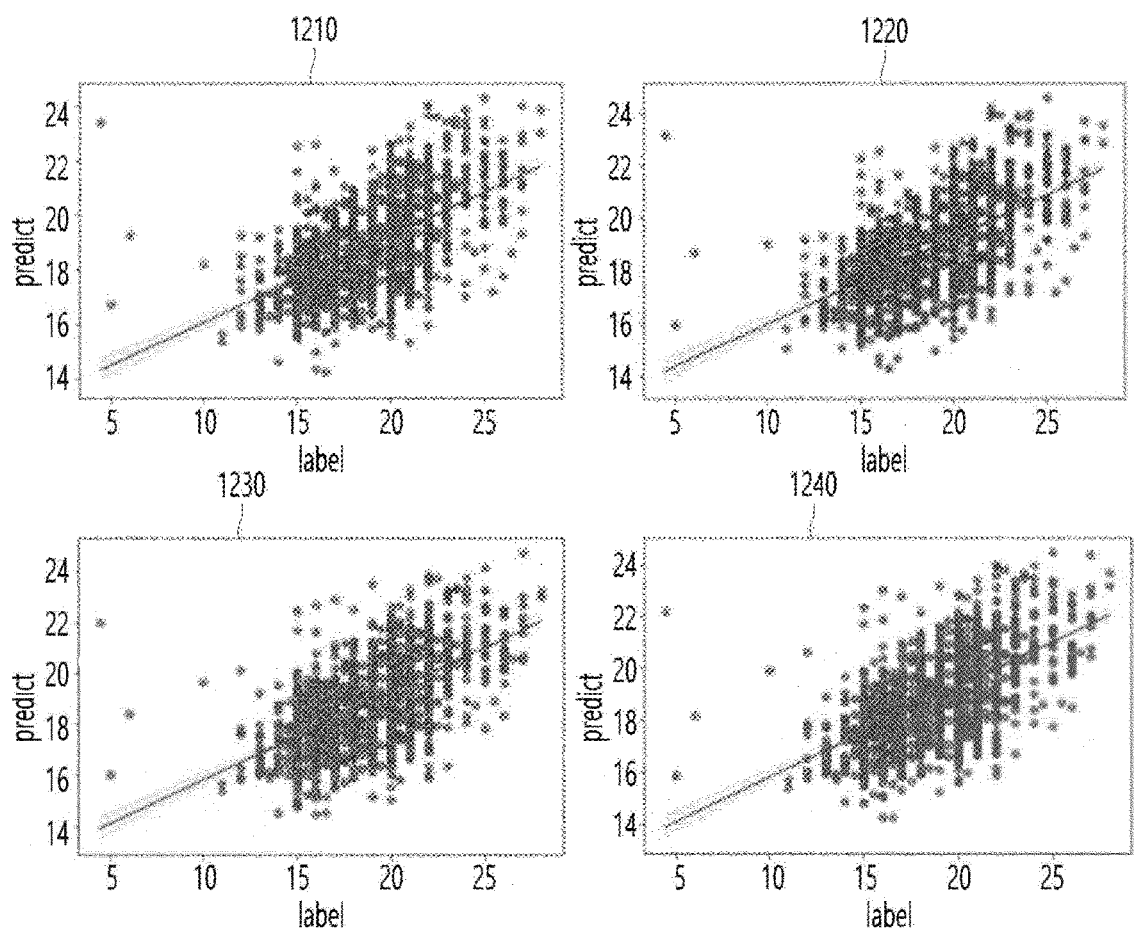
FIG. 12 is a view illustrating experimental results for an exophthalmos degree prediction model that is trained.

FIG. 12 is a view illustrating experimental results for an exophthalmos degree prediction model that is trained.

The experimental results in FIG. 12 are obtained from the exophthalmos degree prediction model trained by using 655 facial images of 348 patients.

Specifically, the exophthalmos degree prediction model is trained by using a training data set that includes, as input data, feature values obtained from each of 655 facial images and includes, as label values, actual exophthalmos numerical values corresponding to respective facial images.

The experimental results in FIG. 12 are the experimental results with different feature values obtained from the facial images. That is, the input data input for the exophthalmos degree prediction model and considered in each experimental result are different for each experimental result.

Referring to FIG. 12, a first experimental result 1210 is an experimental result for the exophthalmos degree prediction model trained by using training data including as input data: z-axis length values of a facial image; and Radial MPLD values of the facial image. In the first experimental result 1210, it is confirmed that MAE is 1.91135 and $r^2$ is 0.32806.

Referring to FIG. 12, a second experimental result 1220 is an experimental result for the exophthalmos degree prediction model trained by using training data including as input data: the z-axis length values of the facial image; the Radial MPLD values of the facial image; and 0-to-180 distance values of the facial image. In the second experimental result 1220, it is confirmed that MAE is 1.90232 and $r^2$ is 0.33316.

Referring to FIG. 12, a third experimental result 1230 is an experimental result for the exophthalmos degree prediction model trained by using training data including as input data: the z-axis length values of the facial image; the Radial MPLD values of the facial image; the 0-to-180 distance values of the facial image; and an eye horizontal length of the facial image. In the third experimental result 1230, it is confirmed that MAE is 1.87273 and $r^2$ is 0.35574.

Referring to FIG. 12, a fourth experimental result 1240 is an experimental result for the exophthalmos degree prediction model trained by using training data including as input data: the z-axis length values of the facial image; the Radial MPLD values of the facial image; the 0-to-180 distance values of the facial image; the eye horizontal length of the facial image; and a distance between the eye horizontal length and an eye center position of the facial image. In the fourth experimental result 1240, it is confirmed that MAE is 1.86234 and $r^2$ is 0.35671.

According to the experimental results, it may be confirmed that the accuracy of exophthalmos degree prediction increases as various feature values are set as the input data. Meanwhile, in a case of comparing the third experimental results 1230 and the fourth experimental results 1240, it may be confirmed that the accuracy increases relatively significantly when the eye horizontal length is included in the input data. That is, it may be confirmed that the eye horizontal length is an important feature value in predicting an exophthalmos degree.

Meanwhile, the exophthalmos degree prediction model may be trained by using training data including, as input data, z-axis length values of a facial image, Radial MPLD values of the facial image, and 90-to-270 distance values of the facial image.

Alternatively, the exophthalmos degree prediction model may be trained by using training data including, as input data, z-axis length values of a facial image, Radial MPLD values of the facial image, 90-to-270 distance values of the facial image, and an eye vertical length of the facial image.

Alternatively, the exophthalmos degree prediction model may be trained by using training data including, as input data, z-axis length values of a facial image, Radial MPLD values of the facial image, 90-to-270 distance values of the facial image, an eye vertical length of the facial image, and a distance between the eye vertical length and the eye center position of the facial image.

Alternatively, the exophthalmos degree prediction model may also be trained by using training data including all the above-described feature values as input data, and the types of feature values included in the input data are not limited to the above-described examples.

Meanwhile, the exophthalmos degree prediction model may receive input of an facial image along with feature values obtainable from the facial image. In this case, the facial image may be a front facial image. Alternatively, the facial image may be an image including an eyeball area and a pupil and iris area, which are obtained by performing image segmentation.

(3) Facial Image-Based Exophthalmos Degree Determination Method—3

An exophthalmos degree may be predicted by inputting a difference value between feature values obtainable from respective facial images at two time points into a trained exophthalmos degree prediction model.

The exophthalmos degree prediction model may be a model trained by using training data that includes, as input data, a difference value between feature values obtainable from respective facial images at two time points and an exophthalmos numerical value corresponding to the facial image at one of the two time points, and that also includes, as a label value, an exophthalmos numerical value corresponding to the facial image at the other of the two time points.

The exophthalmos degree prediction model may be a regression model, a neural network model, a machine learning model, a deep learning model, or a combination thereof, and since the specific details have been described in (2) Facial image-based exophthalmos degree determination method—2, a duplicate description is omitted.

The types of feature values obtainable from a facial image and the method for obtaining the feature values are described above in (2) Facial image-based exophthalmos degree determination method—2, so a duplicate description is omitted.

The exophthalmos degree prediction model may receive input of not only a difference value between a first feature value obtained from a facial image at a first time point and a second feature value obtained from a facial image at a second time point but also an exophthalmos numerical value at the first time point, so as to output an exophthalmos numerical value at the second time point. In this case, the first feature value and second feature value, which are considered to obtain the difference value, are values for the same feature.

Figure 13:
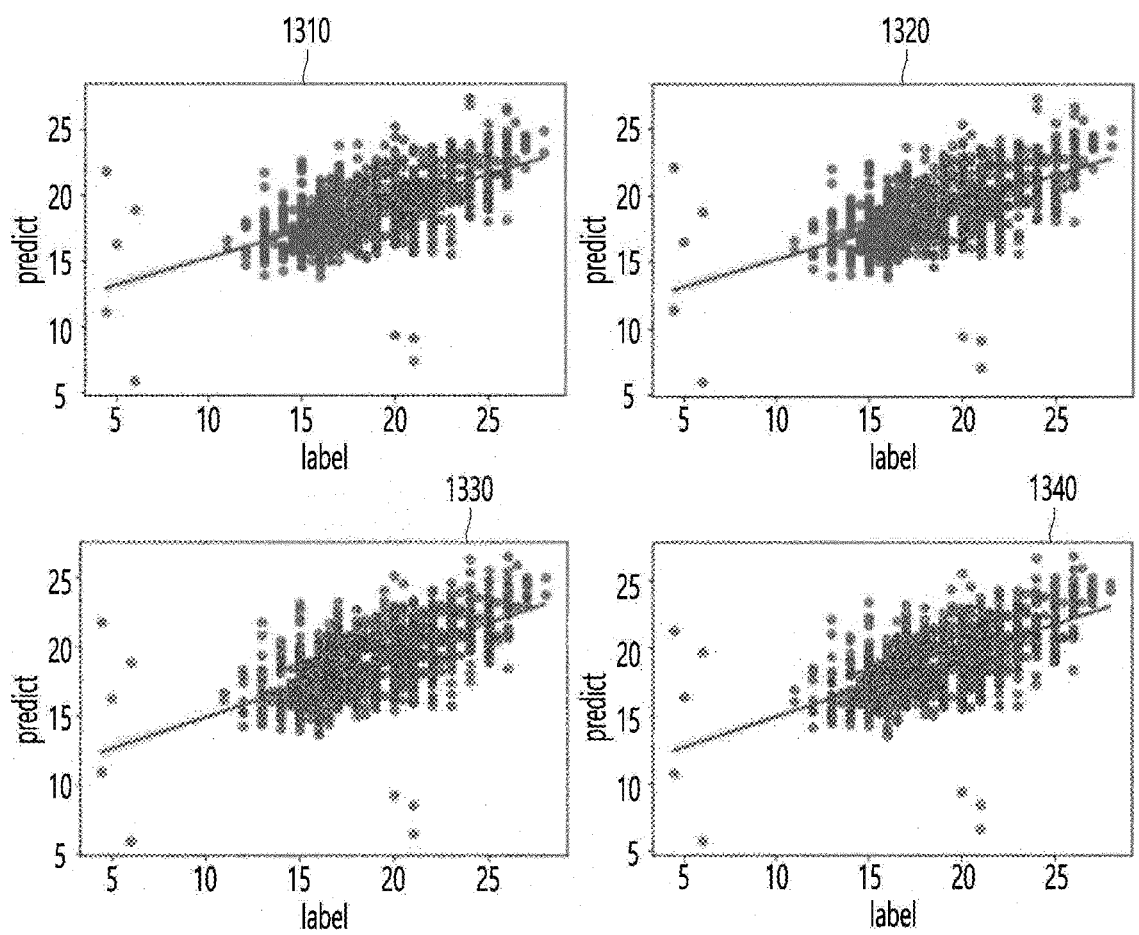
FIG. 13 is a view illustrating experimental results for the exophthalmos degree prediction model that is trained.

FIG. 13 is a view illustrating experimental results for an exophthalmos degree prediction model that is trained.

The experimental results in FIG. 13 are obtained from the exophthalmos degree prediction model trained by using 844 facial image sets of 196 patients. In this case, one facial image set includes two facial images, i.e., a facial image at a first time point and a facial image at a second time point.

Specifically, the exophthalmos degree prediction model is trained by using a training data set that includes, as input data, not only a difference value between a feature value obtained from a facial image at one time point and a feature value obtained from a facial image at the other time point, the facial images being included in each of the 844 facial image sets, but also an exophthalmos numerical value corresponding to the facial image at one time point, and that includes, as a label value, an exophthalmos numerical value corresponding to the facial image at the other time point.

The experimental results in FIG. 13 are the results of experiments performed by applying different feature values obtained from the facial images. That is, the input data input for the exophthalmos degree prediction model and considered in each experimental result is different for each experimental result.

Referring to FIG. 13, a fifth experimental result 1310 is an experimental result for an exophthalmos degree prediction model trained by using training data including as input data: a difference value between an exophthalmos numerical value corresponding to a facial image at one time point and z-axis length values obtained from respective facial images at two time points; and a difference value between Radial MPLD values obtained from the respective facial images at the two time points. In the fifth experimental result 1310, it is confirmed that MAE is 1.85316 and $r^2$ is 0.36599.

Referring to FIG. 13, a sixth experimental result 1320 is an experimental result for the exophthalmos degree prediction model trained by using training data including as input data: the difference value between the exophthalmos numerical value corresponding to the facial image at one time point and the z-axis length values obtained from the respective facial images at the two time points; the difference value between the Radial MPLD values obtained from the respective facial images at the two time points; and a difference value between 0-to-180 distance values obtained from the respective facial images at the two time points. In the sixth experimental result 1320, it is confirmed that MAE is 1.85043 and $r^2$ is 0.36660.

Referring to FIG. 13, a seventh experimental result 1330 is an experimental result for the exophthalmos degree prediction model trained by using training data including as input data: the difference value between the exophthalmos numerical value corresponding to the facial image at one time point and the z-axis length values obtained from the respective facial images at the two time points; the difference value between the Radial MPLD values obtained from the respective facial images at the two time points; the difference value between the 0-to-180 distance values obtained from the respective facial images at the two time points; and a difference value between eye horizontal lengths obtained from the respective facial images at the two time points. In the seventh experimental result 1330, it is confirmed that MAE is 1.78171 and $r^2$ is 0.39728.

Referring to FIG. 13, an eighth experimental result 1340 is an experimental result for the exophthalmos degree prediction model trained by using training data including as input data: the difference value between the exophthalmos numerical value corresponding to the facial image at one time point and the z-axis length values obtained from the respective facial images at the two time points; the difference value between the Radial MPLD values obtained from the respective facial images at the two time points; the difference value between the 0-to-180 distance values obtained from the respective facial images at the two time points; the difference value between the eye horizontal lengths obtained from the respective facial images at the two time points; and difference values between the eye horizontal lengths and distances between center positions, which are obtained from the respective facial images at the two time points. In the eighth experimental result 1340, it is confirmed that MAE is 1.78160 and $r^2$ is 0.39584.

According to the experimental results, it may be confirmed that the more feature values are set, the higher accuracy of exophthalmos degree prediction are obtained. Meanwhile, in a case of comparing the seventh experimental result 1330 and the eighth experimental result 1340, it may be confirmed that the accuracy increases relatively significantly when the eye horizontal lengths are included in the input data. That is, it may be confirmed that the eye horizontal lengths are important feature values in predicting an exophthalmos degree.

Comparing the experimental results in FIG. 13 with the experimental results in FIG. 12, it may be confirmed that using the difference between the feature values obtained from the facial images at two time points provides higher accuracy than that of using only the feature value obtained from the facial image at one time point.

Meanwhile, the exophthalmos degree prediction model may be trained by using training data including as input data: a difference value between an exophthalmos numerical value corresponding to a facial image at one time point and z-axis length values obtained from respective facial images at two time points; a difference value between Radial MPLD values obtained from the respective facial images at the two time points; and a difference value between 90-to-270 distance values obtained from the respective facial images at the two time points.

Meanwhile, the exophthalmos degree prediction model may be trained by using training data including as input data: the difference value between the exophthalmos numerical value corresponding to the facial image at one time point and the z-axis length values obtained from the respective facial images at the two time points; the difference value between the Radial MPLD values obtained from the respective facial images at the two time points; the difference value between the 90-to-270 distance values obtained from the respective facial images at the two time points; and a difference value between eye vertical lengths obtained from the respective facial images at the two time points.

Meanwhile, the exophthalmos degree prediction model may be trained by using training data including as input data: the difference value between the exophthalmos numerical value corresponding to the facial image at one time point and the z-axis length values obtained from the respective facial images at the two time points; the difference value between the Radial MPLD values obtained from the respective facial images at the two time points; the difference value between the 90-to-270 distance values obtained from the respective facial images at the two time points, the difference value between the eye vertical lengths obtained from the respective facial images at the two time points; and difference values between the eye vertical lengths and distances between center positions obtained from the respective facial images at the two time points.

Alternatively, the exophthalmos degree prediction model may also be trained by using training data including as input data: exophthalmos numerical values corresponding to a facial image at one time point; and difference values of various types of feature values obtained from respective facial images at two time points. The types of feature values included in the input data are not limited to the examples described above. Meanwhile, the exophthalmos degree prediction model may also receive input of the facial images at two time points together along with the difference values of the feature values obtainable from the respective facial images at the two time points In this case, the facial image may be a front facial image. Alternatively, the facial image may be an image including an eyeball area and a pupil and iris area, which are obtained by performing image segmentation.

(4) Facial Image-Based Exophthalmos Degree Determination Method—4

Meanwhile, since an exophthalmos degree is a vertical distance between a corneal apex and a lateral orbital rim, the exophthalmos degree may also be estimated on the basis of a side facial image.

In order to estimate an exophthalmos degree from the side facial image, a front facial image corresponding to the side facial image may be obtained along with the side facial image.

Figure 14:
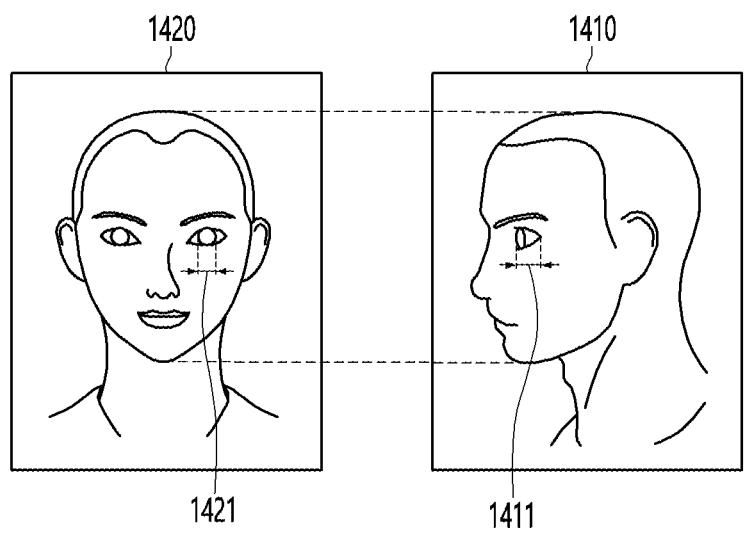
FIG. 14 is a view illustrating a method for estimating an exophthalmos degree by using a side facial image.

FIG. 14 is a view illustrating a method for estimating an exophthalmos degree by using a side facial image.

Referring to FIG. 14, a distance 1411 between a corneal endpoint and an eye endpoint may be calculated from the side facial image 1410. In this case, the distance 1411 between the corneal endpoint and the eye endpoint may be a pixel distance. An image segmentation model may be used to calculate the distance 1411 between the corneal endpoint and the eye endpoint from the side facial image 1410, but it is not limited thereto.

Meanwhile, a distance 1421 corresponding to a radius of a pupil may be calculated from a front facial image 1420 corresponding to the side facial image 1410. In this case, the distance 1421 corresponding to the radius of the pupil may be a pixel distance. The image segmentation model may be used to calculate the distance 1421 corresponding to the radius of the pupil from the front facial image 1420, but it is not limited thereto.

The fact that the side facial image 1410 and the front facial image 1420 correspond to each other may mean that the resolution of each of the images is the same or that a difference in each resolution is within a threshold. Specifically, it may mean that a ratio of a pixel distance and an actual distance on the side facial image 1410 is the same as a ratio of a pixel distance and an actual distance on the front facial image 1420, or that a difference between the ratios is within a threshold.

In order to obtain a front facial image 1420 corresponding to a side facial image 1410, the side facial image 1410 and the front facial image 1420 may be captured in a condition where a distance between a face and a photographing device when capturing the side facial image 1410 and a distance between the face and the photographing device when capturing the front facial image 1420 are the same. In this case, the photographing device may be a patient's user device, but it is not limited thereto, and may also be medical staff device at a hospital.

Meanwhile, as described above, the actual length of the radius of the pupil and iris is generally similar for each person, and specifically, the actual length of the radius of the pupil and iris may be 5.735 mm for men and 5.585 mm for women.

That is, the resolution of the front facial image 1420 may be determined by using a pupil radius length 1421 calculated from the front facial image 1420 and the actual length of the radius of the pupil.

Since the resolution of each of the side facial image 1410 and the front facial image 1420 is the same, an actual distance corresponding to a distance 1411 between the corneal endpoint and the eye endpoint on the side facial image 1410 may be calculated on the basis of the resolution determined from the front facial image 1420.

Specifically, the actual distance between the corneal endpoint and the eye endpoint may be calculated by multiplying a ratio value of the pupil radius length 1421 calculated from the front facial image 1420 and the actual length of the radius of the pupil and iris by a distance 1411 between the corneal endpoint and eye endpoint calculated from the side facial image 1410.

The calculated actual distance between the corneal endpoint and the eye endpoint may be an estimation value of an exophthalmos degree.

Meanwhile, in FIG. 14, the front facial image 1420 and the side facial image 1410 are depicted as separate images, but a facial image used for estimating an exophthalmos degree may be a facial image captured panoramically from the front to the side of a face.

Specifically, a distance corresponding to a radius of a pupil and a distance between a corneal endpoint and an eye endpoint may be calculated from a facial image captured panoramically from the front to the side of a face. In this case, each of a distance corresponding to the radius of the pupil and the distance between the corneal endpoint and the eye endpoint may be calculated as a pixel distance.

The actual distance between the corneal endpoint and the eye endpoint may be calculated by multiplying a ratio value of the distance corresponding to the calculated radius of the pupil and the actual distance of the radius of the pupil by a distance between the corneal endpoint and the eye endpoint.

That is, an exophthalmos degree may be estimated as the distance between the calculated corneal endpoint and the eye endpoint.

6. Facial Image-Based Exophthalmos Degree Trend Determination Method

Even without determining a numerical value itself of an exophthalmos degree from a facial image, a trend in the exophthalmos degrees may be determined on the basis of a comparison of facial images at two time points. That is, in a case where it is difficult to calculate the numerical value itself of the exophthalmos degree from the facial image, it is possible to monitor whether a medicine is effective or not following the administration of a medicine for the purpose of thyroid ophthalmopathy treatment by comparing facial images at two time points and determining a trend in the exophthalmos degrees. In this case, the trend in exophthalmos degrees may mean the trend of changes in the exophthalmos degrees.

Meanwhile, facial images may be obtained from a patient. Specifically, the facial image may be obtained from the patient's user device, and the facial image may be an image captured by the patient's user device, but it is not limited thereto, and a facial image may also be obtained from a hospital. Specifically, the facial image may be obtained by allowing medical staff assigned at the hospital to capture the patient's face when the patient visits the hospital.

A facial image may be an image of an area between a lower end of a nose and an upper end of an eyebrow, but it is not limited thereto, and the facial image may mean an image that illustrates an eye region.

Figure 15:
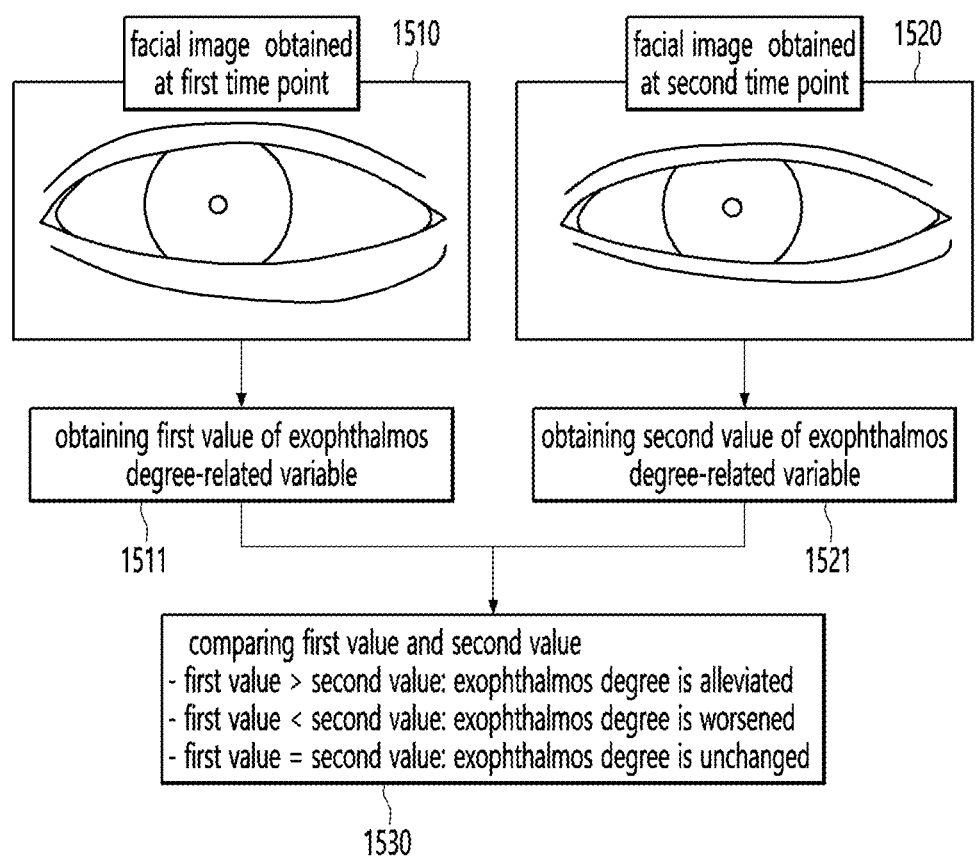
FIG. 15 is a view illustrating a method for determining a trend in the exophthalmos degrees on the basis of facial images.

FIG. 15 is a view illustrating a method for determining a trend in exophthalmos degrees on the basis of facial images.

Referring to FIG. 15, obtaining 1511 a first value of an exophthalmos degree-related variable from a facial image 1510 obtained at a first time point may be performed, and obtaining 1521 a second value of an exophthalmos degree-related variable from a facial image 1520 obtained at a second time point may be performed. In this case, the second time point may be a time point later than the first time point.

In this case, the same photographing guide may be provided to capture facial images at the first and second time points. That is, the patient's face shown in both of the facial image 1510 obtained at the first time point and the facial image 1520 obtained at the second time point may have the same composition. Accordingly, the facial image 1510 obtained at the first time point and the facial image 1520 obtained at the second time point may be compared with each other. Specifically, the first value of the variable related to an exophthalmos degree obtained from the facial image 1510 obtained at the first time point and the second value of the variable related to an exophthalmos degree obtained from the facial image 1520 obtained at the second time point may be compared with each other. The specific details related to the photographing guide are described later in 8. Capturing and transmitting facial image.

The variable related to an exophthalmos degree is a variable obtainable by analyzing a facial image, and may mean a variable whose value increases as the exophthalmos degree increases. Specifically, the variable related to the exophthalmos degree may increase in direct proportion or in square proportion as the exophthalmos degree increases, and an increase or decrease in the variable related to the exophthalmos degree according to the increase or decrease of the exophthalmos degree is not limited thereto.

Accordingly, a trend in the exophthalmos degrees between the first time point and the second time point may be determined by performing a comparison 1530 of the first value of the exophthalmos degree-related variable obtained from the facial image 1510 obtained at the first time point and the second value of the exophthalmos degree-related variable obtained from the facial image 1520 obtained at the second time point.

Whether the exophthalmos degree has alleviated, worsened, or unchanged between the first to second time points may be determined on the basis of the trend of the determined exophthalmos degrees.

Specifically, in a case where the second value is smaller than the first value, it may be determined that the trend in the exophthalmos degrees is decreasing between the first time point and the second time point, and since the trend in the exophthalmos degrees is decreasing, it may be determined that the exophthalmos degrees have alleviated between the first time point and the second time point Accordingly, it may be determined that the effectiveness of medicine appears between the first and second time points.

Alternatively, in a case where the second value is greater than the first value, the trend in the exophthalmos degrees between the first and second time points may be determined as an increasing trend, and since the trend in the exophthalmos degrees is the increasing trend, it may be determined that the exophthalmos degrees have worsened between the first and second time points. Accordingly, it may be determined that the effectiveness of medicine does not appear between the first and second time points.

Alternatively, in a case where the second value and the first value are the same, the trend in the exophthalmos degrees between the first time point and the second time point may be determined as an unchanged trend, and since the trend in the exophthalmos degrees is the unchanged trend, it may be determined that the exophthalmos degrees have unchanged between the first and the second time points. Accordingly, it may be determined that the effectiveness of medicine does not appear between the first and second time points.

Meanwhile, the exophthalmos degree-related variables may be variable for values including: a numerical value of an exophthalmos degree, a Multiple Radial Mid-Pupil Lid Distance (Radial MPLD) value, an eye horizontal length, a 3D facial landmark coordinate value, and/or a value for a distance between a corneal endpoint and an eye endpoint. The exophthalmos degree-related variables are not limited to the examples described above.

Among the exophthalmos degree-related variables, the numerical value of the exophthalmos degree may be obtained by the facial image-based exophthalmos degree determination method described above.

Specifically, a first exophthalmos numerical value may be obtained as a first value of an exophthalmos degree-related variable from a first time-point facial image 1510, and a second exophthalmos numerical value may be obtained as a second value of the exophthalmos degree-related variable from a second time-point facial image 1520. The specific details related to obtaining exophthalmos numerical values from facial images have been described above in the facial image-based exophthalmos degree determination method, so a duplicate description is omitted.

Exophthalmos numerical values obtained from a facial image belong to a variable whose value increases as an exophthalmos degree increases and whose value decreases as an exophthalmos degree decreases. Therefore, a trend in the exophthalmos degrees between the first time point and the second time point may be determined by comparing a first exophthalmos numerical value and a second exophthalmos numerical value.

Among the exophthalmos degree-related variables, Radial MPLD values may be obtained by the method described above in 5. Facial image-based exophthalmos degree determination method.

Specifically, a first eyeball area and a first pupil and iris area that are shown in a first time-point facial image 1510 may be detected by applying the first time-point facial image 1510 to an image segmentation model. A first boundary between an eyeball and an eyelid in the first time-point facial image 1510 may be identified on the basis of the detected first eyeball area. A first center position of pupil and iris shown in the first time-point facial image 1510 may be identified on the basis of the detected first pupil and iris area.

A first Radial MPLD value may be calculated as an angular-specific distance value from the first position of the pupil center to the first boundary between the eyeball and the eyelid. The specific method for calculating Radial MPLD values has been described above in 5. Facial image-based exophthalmos degree determination method, so a duplicate description is omitted.

A second eyeball area and a second pupil and iris area shown in a second time-point facial image 1520 may be detected by applying the second time-point facial image 1520 to the image segmentation model. A second boundary between an eyeball and an eyelid shown in the second time-point facial image 1520 may be identified on the basis of the detected second eyeball area. A second center position of pupil and iris shown in the second time-point facial image 1520 may be identified on the basis of the detected second pupil and iris area. A second Radial MPLD value may be calculated as an angular-specific distance value from the second position of the pupil center to the second boundary between the eyeball and the eyelid. The specific method for calculating Radial MPLD values has been described above in 5. Facial image-based exophthalmos degree determination method, so a duplicate description is omitted.

Radial MPLD values obtained from the facial image belong to a variable whose value increases as an exophthalmos degree increases and whose value decreases as an exophthalmos degree decreases. Therefore, a trend in the exophthalmos degrees between the first time point and the second time point may be determined by comparing the first Radial MPLD value and the second Radial MPLD value.

In this case, a trend in the exophthalmos degrees may be determined by comparing values between 195 and 345 degrees among the Radial MPLD values. Specifically, the trend in the exophthalmos degrees may be determined by comparing values between 195 degrees and 345 degrees determined from among first Radial MPLD values obtained from the facial image at the first time point with values between 195 degrees and 345 degrees determined from among second Radial MPLD values obtained from the facial image at the second time point. An angle determined from among the first Radial MPLD values and an angle determined from among the second Radial MPLD values may be equal to each other.

The use of values between 195 and 345 degrees from among the Radial MPLD values in order to determine the trend in the exophthalmos degrees is described with reference to FIGS. 16 and 17.

Figure 16:
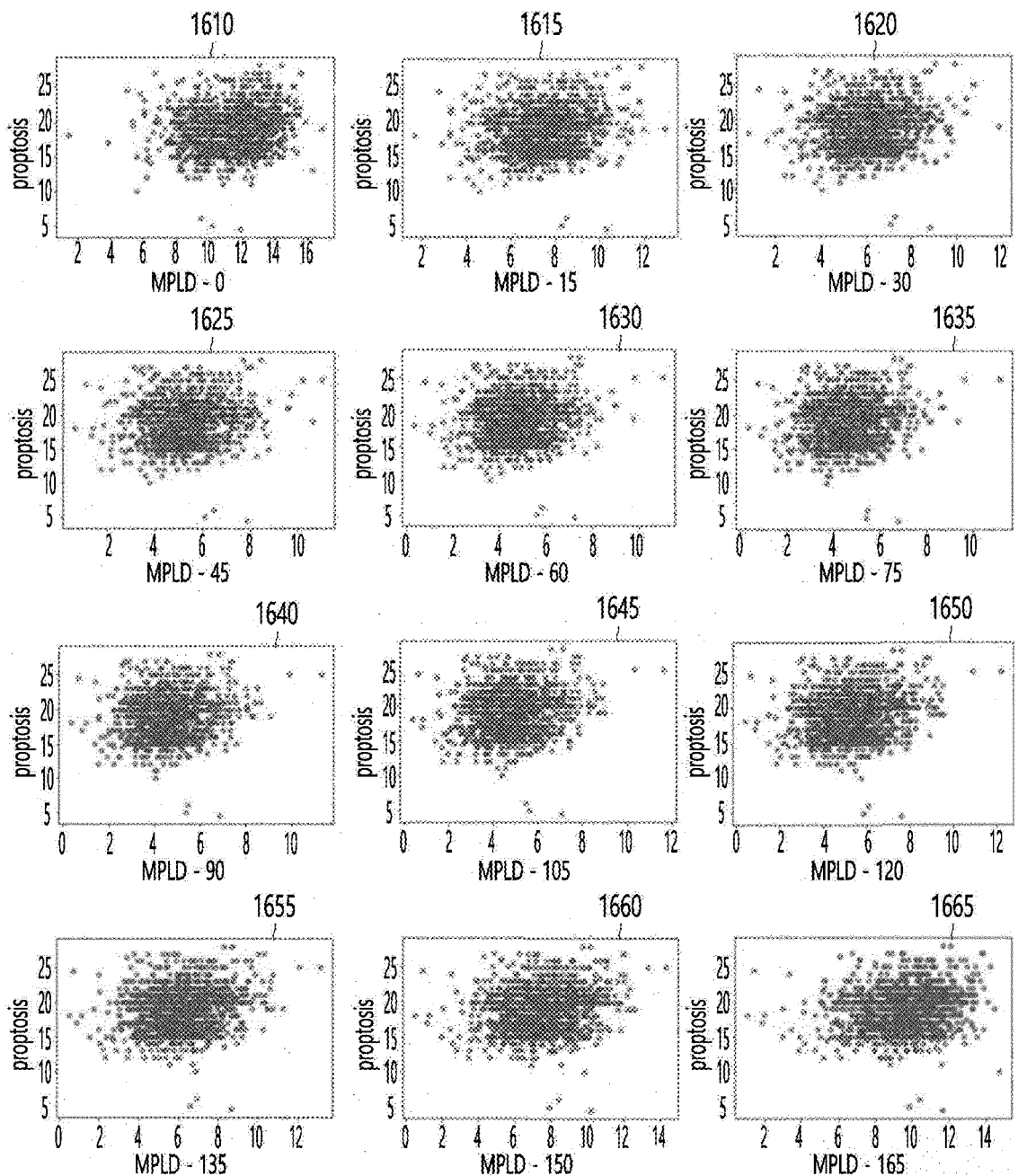
FIGS. 16 and 17 are graphs illustrating relationships between radial Multiple Radial Mid-Pupil Lid Distance (radial MPLD) values and exophthalmos degrees.
Figure 17:
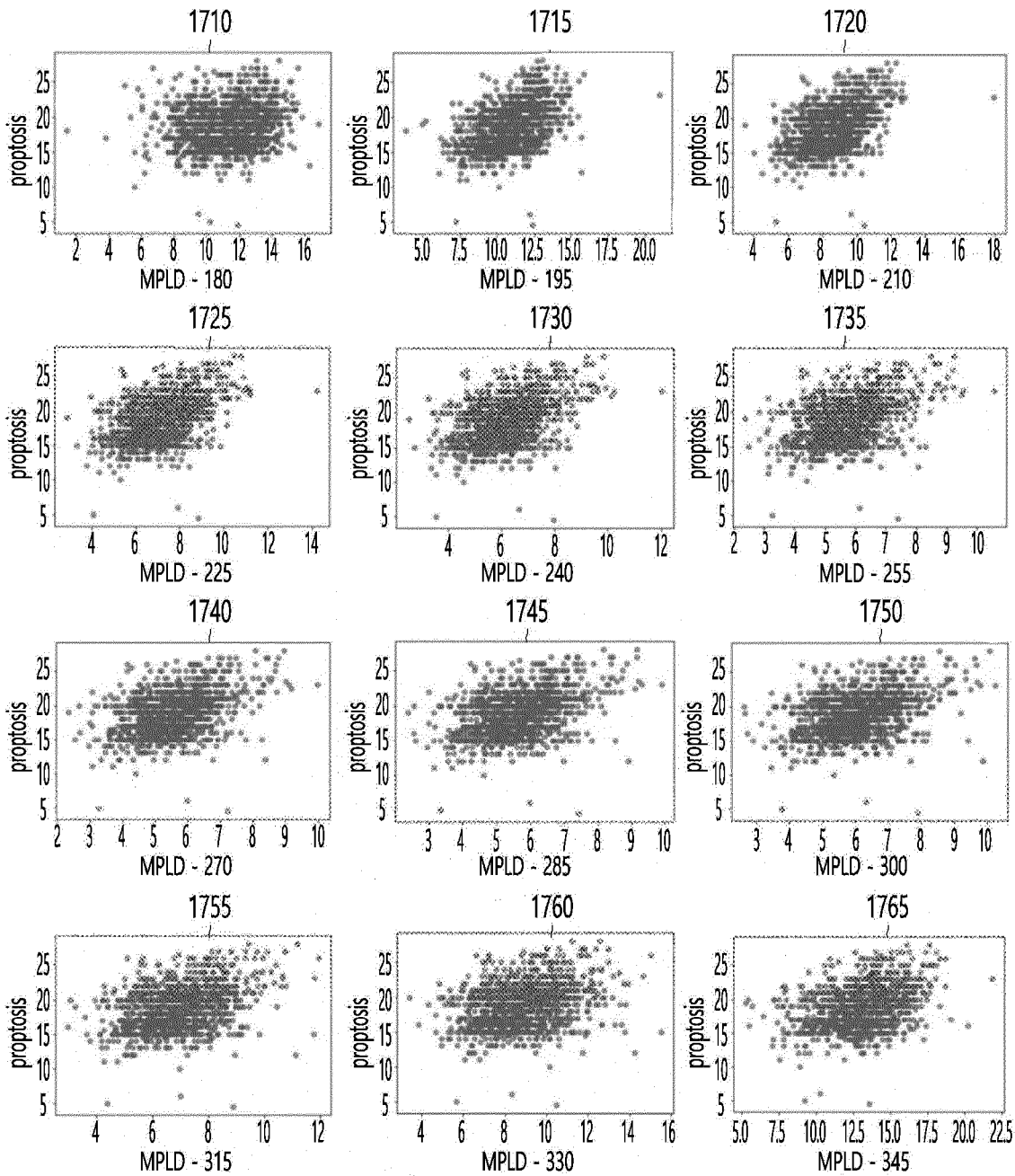

FIGS. 16 and 17 are graphs illustrating relationships between Radial MPLD values and exophthalmos degrees.

FIG. 16 illustrates exophthalmos degree distribution graphs for Radial MPLD values, the graphs including: an exophthalmos degree distribution graph 1610 for values corresponding to 0 degrees; an exophthalmos degree distribution graph 1615 for values corresponding to 15 degrees; an exophthalmos degree distribution graph 1620 for values corresponding to 30 degrees; an exophthalmos degree distribution graph 1625 for values corresponding to 45 degrees; an exophthalmos degree distribution graph 1630 for values corresponding to 60 degrees; an exophthalmos degree distribution graph 1635 for values corresponding to 75 degrees; an exophthalmos degree distribution graph 1640 for values corresponding to 90 degrees; an exophthalmos degree distribution graph 1645 for values corresponding to 105 degrees; an exophthalmos degree distribution graph 1650 for values corresponding to 120 degrees; an exophthalmos degree distribution graph 1655 for values corresponding to 135 degrees; an exophthalmos degree distribution graph

1660 for values corresponding to 150 degrees; and an exophthalmos degree distribution graph 1665 for values corresponding to 165 degrees.

FIG. 17 illustrates exophthalmos degree distribution graphs for Radial MPLD values, the graphs including: an exophthalmos degree distribution graph 1710 for values corresponding to 180 degrees; an exophthalmos degree distribution graph 1715 for values corresponding to 195 degrees; an exophthalmos degree distribution graph 1720 for values corresponding to 210 degrees; an exophthalmos degree distribution graph 1725 for values corresponding to 225 degrees; an exophthalmos degree distribution graph 1730 for values corresponding to 240 degrees; an exophthalmos degree distribution graph 1735 for values corresponding to 255 degrees; an exophthalmos degree distribution graph 1740 for values corresponding to 270 degrees; an exophthalmos degree distribution graph 1745 for values corresponding to 285 degrees; an exophthalmos degree distribution graph 1750 for values corresponding to 300 degrees; an exophthalmos degree distribution graph 1755 for values corresponding to 315 degrees; an exophthalmos degree distribution graph 1760 for values corresponding to 330 degrees; and an exophthalmos degree distribution graph 1765 for values corresponding to 345 degrees.

Referring to FIGS. 16 and 17, for the Radial MPLD values corresponding to 0 to 180 degrees in the graphs 1610, 1615, 1620, 1625, 1630, 1635, 1640, 1645, 1650, 1655, 1660, 1665, and 1710, there is no increase or decrease in the values according to the increase or decrease in the exophthalmos degrees. However, for the Radial MPLD values corresponding to 195 to 345 degrees in the graphs 1715, 1720, 1725, 1730, 1735, 1740, 1745, 1750, 1755, 1760, and 1765, there are shown distributions in the upward-right diagonal direction where the Radial MPLD values increase as the exophthalmos degrees increase, and the Radial MPLD values decrease as the exophthalmos degrees decrease. Accordingly, the trend in the exophthalmos degrees may be determined by comparing the values between 195 and 345 degrees from among the Radial MPLD values.

Meanwhile, each Radial MPLD value obtained from the facial image may be calculated as an actual distance, but it is not limited thereto, and each radial MPLD value obtained from the facial image may also be calculated as a pixel distance.

In this case, in order to compare a first Radial MPLD value and a second Radial MPLD value, a first pupil-radius pixel distance shown in the first time-point facial image 1510 and a second pupil-radius pixel distance shown in the second time-point facial image 1520 may be used. In this case, the first time-point facial image 1510 and the second time-point facial image 1520 may be front facial images.

Specifically, a ratio of a first Radial MPLD value to a first pupil-radius pixel distance may be compared with a ratio of a second Radial MPLD value to a second pupil-radius pixel distance.

That is, a trend in the exophthalmos degrees may be determined by comparing the ratio of the first Radial MPLD value to the first pupil-radius pixel distance and the ratio of the second Radial MPLD value to the second pupil-radius pixel distance.

Among the exophthalmos degree-related variables, an eye horizontal length may mean a horizontal length of an eyeball area shown in a front facial image. Specifically, the eye horizontal length may mean a distance between the leftmost and rightmost points of the eyeball area. Alternatively, the eye horizontal length may mean a length in the x-axis direction of the eyeball area. This is not limited thereto, and the eye horizontal length may also mean a length between a position of an outer corner of an eye and a position of a lacrimal caruncle in the eyeball area.

Meanwhile, an eye horizontal length may be calculated on the basis of a horizontal length of an eyeball area obtained by applying a front facial image to the image segmentation model. Since the details related to obtaining the eyeball area by applying the front facial image to the image segmentation model have been described above, a duplicate description is omitted.

Specifically, a first eyeball area shown in a first time-point facial image 1510 may be detected by applying a first time-point facial image 1510 to the image segmentation model. A horizontal length of a first eye shown in the first time-point facial image 1510 may be calculated on the basis of the horizontal length of the first eyeball area.

A second eyeball area shown in a second time-point facial image 1520 may be detected by applying the second time-point facial image 1520 to the image segmentation model. A horizontal length of a second eye shown in the second time-point facial image 1520 may be calculated on the basis of a horizontal length of the second eyeball area.

The eye horizontal lengths obtained from the facial image belong to a variable whose value increases as an exophthalmos degree increases and whose value decreases as an exophthalmos degree decreases. Therefore, a trend in the exophthalmos degrees between the first time point and the second time point may be determined by comparing the horizontal length of the first eye and the horizontal length of the second eye.

Figure 18:
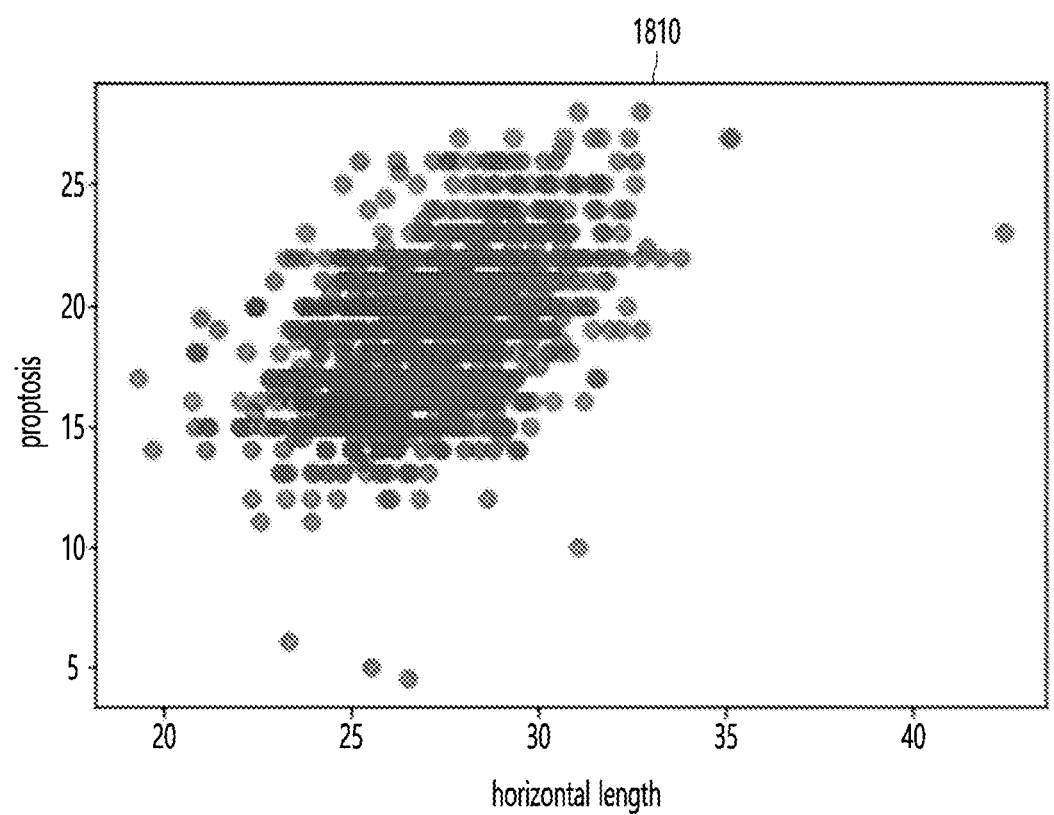
FIG. 18 is a graph illustrating relationships between eye horizontal lengths and exophthalmos degrees.

FIG. 18 is a graph illustrating relationships between eye horizontal lengths and exophthalmos degrees.

In FIG. 18, an eye horizontal length is set as a distance between the leftmost and rightmost points of an eyeball area.

Referring to FIG. 18, a distribution in an upward right diagonal direction is shown where an eye horizontal length increases as an exophthalmos degree increases and an eye horizontal length decreases as an exophthalmos degree decreases. Accordingly, a trend in the exophthalmos degrees may be determined by comparing the eye horizontal lengths.

Meanwhile, an eye horizontal length obtained from a facial image may be calculated as an actual distance, but it is not limited thereto. The eye horizontal length obtained from the facial image may also be calculated as a pixel distance.

In this case, in order to compare a horizontal length of a first eye and a horizontal length of a second eye, a first pupil-radius pixel distance shown in a first time-point facial image 1510 and a second pupil-radius pixel distance shown in a second time-point facial image 1520 may be used. In this case, the first time-point facial image 1510 and the second time-point facial image 1520 may be front facial images.

Specifically, a ratio of the horizontal length of the first eye to the first pupil-radius pixel distance may be compared with a ratio of the horizontal length of the second eye to the second pupil-radius pixel distance.

That is, the trend in the exophthalmos degrees may be determined by comparing the ratio of the horizontal length of the first eye to the first pupil-radius pixel distance and the ratio of the horizontal length of the second eye to the second pupil-radius pixel distance.

Three-dimensional (3D) facial landmark coordinate values may be obtained by applying a facial image to a 3D facial landmark detection model. Among the obtained 3D facial landmark coordinate values, a z-axis distance value between a z-axis coordinate value of a landmark representing an outer edge of a pupil and a z-axis coordinate value of a landmark representing an outer corner of an eye may be considered as a value for an exophthalmos degree-related variable. Since the details related to the 3D facial landmark detection model have been described above in 5. Facial image-based exophthalmos degree determination method, so a duplicate description is omitted.

Specifically, by applying the 3D facial landmark detection model to a first time-point facial image 1510, a first z-axis coordinate value of a landmark representing the outer edge of a pupil and a second z-axis coordinate value of a landmark representing the outer corner of an eye may be obtained. A first z-axis distance value may be obtained on the basis of a distance between the first z-axis coordinate value and the second z-axis coordinate value.

By applying the 3D facial landmark detection model to a second time-point facial image 1520, a third z-axis coordinate value of the landmark representing the outer edge of the pupil and a fourth z-axis coordinate value of the landmark representing the outer corner of the eye may be obtained. A second z-axis distance value may be obtained on the basis of a distance between the third z-axis coordinate value and the fourth z-axis coordinate value.

The z-axis distance values between the z-axis coordinate values of the landmark representing the outer edge of the pupil and the z-axis coordinate values of the landmark representing the outer corner of the eye, which are obtained from the facial image, belong to a variable whose value increases as an exophthalmos degree increases and whose value decreases as an exophthalmos degree decreases. Therefore, a trend in the exophthalmos degrees between the first time point and the second time point may be determined by comparing the first z-axis distance value and the second z-axis distance value.

Meanwhile, each of the z-axis distance values obtained from the facial image may be calculated as an actual distance, but it is not limited thereto. Each of the z-axis distance value obtained from the facial image may also be calculated as a pixel distance.

In this case, in order to compare the first z-axis distance value and the second z-axis distance value, the first pupil-radius pixel distance shown in the first time-point facial image 1510 and the second pupil-radius pixel distance shown in the second time-point facial image 1520 may be used.

Specifically, a ratio of the first z-axis distance value and the first pupil-radius pixel distance may be compared with a ratio of the second z-axis distance value and the second pupil-radius pixel distance.

That is, a trend in the exophthalmos degrees may be determined by comparing the ratio of the first z-axis distance value and the first pupil-radius pixel distance and the ratio of the second z-axis distance value and the second pupil-radius pixel distance.

Among the exophthalmos degree-related variables, a distance between a corneal endpoint and an eye endpoint may be obtained by using the method described above in the method for determining exophthalmos degrees based on a side facial image.

Specifically, a first distance between the corneal endpoint and the eye endpoint may be obtained as a first value of the exophthalmos degree-related variable from the first time-point facial image 1510, and a second distance between a corneal endpoint and the eye endpoint may be obtained as a second value of the exophthalmos degree-related variable from the second time-point facial image 1520. The specific method for obtaining the distance between the corneal endpoint and the eye endpoint from the facial image has been described above in the facial image-based exophthalmos degree determination method, so a duplicate description is omitted.

The distances between the corneal endpoint and the eye endpoint and obtained from the facial images belong to a variable whose value increases as an exophthalmos degree increases and whose value decreases as an exophthalmos degree decreases. Therefore, a trend in the exophthalmos degrees between the first time point and the second time point may be determined by comparing the first distance between the corneal endpoint and the eye endpoint and the second distance between the corneal endpoint and the eye endpoint.

Meanwhile, each of the distances between the corneal endpoints and the eye endpoints obtained from the facial images may be calculated as an actual distance, but it is not limited thereto. Each of the distances between the corneal endpoints and the eye endpoints obtained from the facial images may also be calculated as a pixel distance, but it is not limited thereto.

In this case, the first pupil-radius pixel distance shown in the first time-point facial image 1510 and the second pupil-radius pixel distance shown in the second time-point facial image 1520 may be used to compare the first distance between the corneal endpoint and the eye endpoint and the second distance between the corneal endpoint and the eye endpoint. In this case, the first pupil-radius pixel distance may be obtained from the front facial image included in the first time-point facial image 1510, and the second pupil-radius pixel distance may be obtained from the front facial image included in the second time-point facial image 1520.

Specifically, the ratio of the first distance between the corneal endpoint and the eye endpoint to the first pupil-radius pixel distance may be compared to the ratio of the second distance between the corneal endpoint and the eye endpoint to the second pupil-radius pixel distance.

That is, the trend in the exophthalmos degrees may be determined by comparing the ratio of the first distance between the corneal endpoint and the eye endpoint to the first pupil-radius pixel distance and the ratio of the second distance between the corneal endpoint and the eye endpoint to the second pupil-radius pixel distance.

7. Facial Image-Based Eyelid Retraction Determination Method

Eyelid retraction is an indicator of how much of a sclera is exposed when an upper eyelid is pulled upward or a lower eyelid is drooped. The eyelid retraction may be determined by a distance between a center position of pupil and iris and the upper eyelid and a distance between the center position of pupil and iris and the lower eyelid. That is, in order to determine the eyelid retraction, the center position of pupil and iris on a facial image and a boundary between an eyeball and an eyelid have to be determined.

The eyelid retraction is determined by the distance between the pupil center and the upper eyelid or the distance between the pupil center and the lower eyelid, and an exophthalmos degree is determined by a vertical distance between a corneal apex and a lateral orbital rim, so the eyelid retraction and the exophthalmos degree may be understood as indicators different from each other.

The center position of a pupil may be determined on the basis of a pupil and iris area detected by applying an image segmentation model to a front facial image as described above. The method for determining the center position of pupil and iris from a front facial image has been described above in 5. Facial image-based exophthalmos degree determination method, so a duplicate description is omitted.

A boundary between an eyeball and an eyelid may be determined on the basis of an eyeball area detected by applying the image segmentation model to a front facial image as described above. The method for determining the boundary between the eyeball and the eyelid from the front facial image has been described above in 5. Facial image-based exophthalmos degree determination method, so a duplicate description is omitted.

Meanwhile, a facial image may be obtained from a patient. Specifically, the facial image may be obtained from a user device of the patient, and the facial image may be an image captured by the patient's user device but it is not limited thereto, and a facial image may also be obtained from a hospital. Specifically, the facial image may be obtained by allowing medical staff assigned at the hospital to capture the patient's face when the patient visits the hospital.

The facial image may be an image of an area between a lower end of a nose and an upper end of an eyebrow. This is not limited thereto, and the facial image may mean an image that illustrates an eye region.

Figure 19:
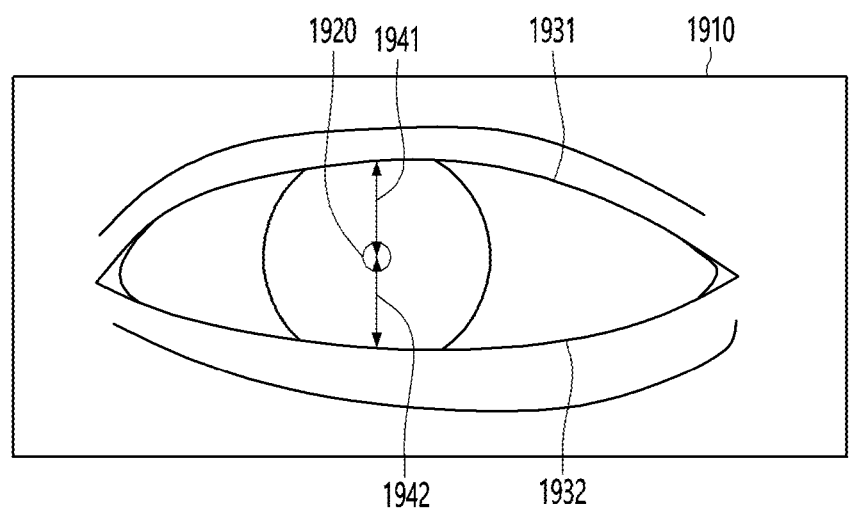
FIG. 19 is a view illustrating a method for determining eyelid retraction from front facial images.
Figure 19:
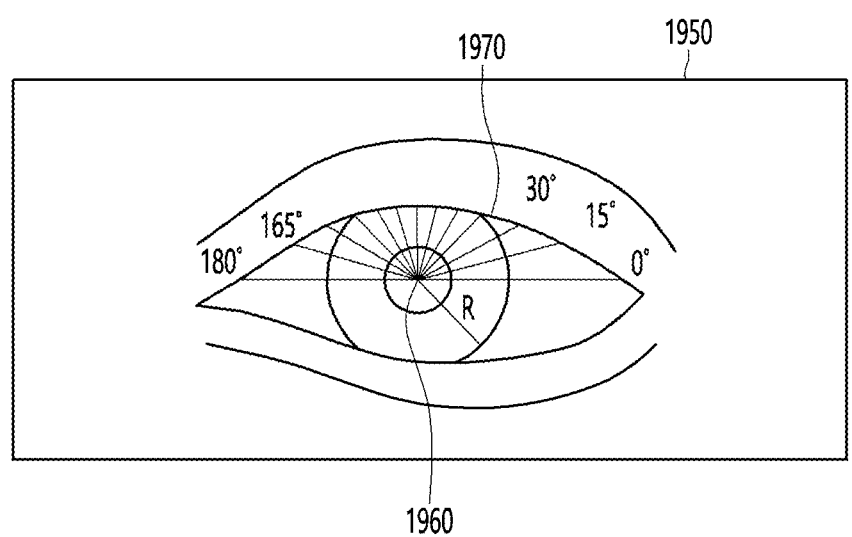

FIG. 19 is a view illustrating a method for determining eyelid retraction from front facial images.

Referring to FIG. 19, a center position of pupil and iris 1920 may be determined on the basis of a pupil and iris area detected by applying the image segmentation model to a front facial image 1910. An upper eyelid boundary 1931 and a lower eyelid boundary 1932 may be determined on the basis of an eyeball area detected by applying the image segmentation model to the front facial image 1910. The method for determining the center position of pupil and iris and the boundary between the eyeball and the eyelid from the front facial image has been described above in 5. Facial image-based exophthalmos degree determination method, so a duplicate description is omitted.

Referring to FIG. 19, a Margin Reflex Distance 1 (MRD1) 1941, which is a value related to eyelid retraction, may be calculated on the basis of the center position of pupil and iris 1920 and the upper eyelid boundary 1931.

Meanwhile, a Margin Reflex Distance 2 (MRD2) 1942, a value related to eyelid retraction, may be calculated on the basis of the center position of pupil and iris 1920 and the lower eyelid boundary 1932.

The MRD1 may mean a distance from a center position of a pupil to a center position of an upper eyelid boundary of a patient when the patient is looking straight ahead, and the MRD2 may mean a distance from the center position of the pupil to a center position of a lower eyelid boundary of the patient when the patient is looking straight ahead.

Meanwhile, each of the MRD1 and MRD2 obtained from a facial image may be calculated as a pixel distance, and an actual distances for each of the MRD1 and MRD2 may be calculated by using a radius of the pupil.

Specifically, a pixel distance corresponding to a radius of a pupil is obtained from a front facial image, and the resolution of the image is determined by considering the pixel distance corresponding to the radius of the pupil and an actual length of the radius of the pupil. Thereafter, actual distances corresponding to pixel distances of the MRD1 and MRD2 may be calculated by considering the resolution of the image.

Referring back to FIG. 19, the center position of pupil and iris 1960 may be determined on the basis of the pupil and iris area detected by applying the image segmentation model to the front facial image 1950. The boundary 1970 between the eyeball and the eyelid may be determined on the basis of the eyeball area detected by applying the image segmentation model to the front facial image 1950.

The method for determining the center position of pupil and iris and the boundary between the eyeball and the eyelid from the front facial image has been described above in 5. Facial image-based exophthalmos degree determination method, so a duplicate description is omitted.

Referring to FIG. 19, Radial MPLD values may be calculated with distances from the center position of pupil and iris 1960 as a center to the boundary 1970 between the eyeball and the eyelid. Angles may be distinguished in 15-degree units while the x-axis direction of the image is set to 0 degrees, and the details related to the calculation of the Radial MPLD values have been described above in 5. Facial image-based exophthalmos degree determination method, so a duplicate explanation is omitted.

Among the Radial MPLD values, values corresponding to 90 degrees and/or 270 degrees may be calculated as values related to eyelid retraction. Specifically, among the Radial MPLD values, a value corresponding to 90 degrees may be a value related to upper eyelid retraction, and among the Radial MPLD values, a value corresponding to 270 degrees may be a value related to lower eyelid retraction.

Meanwhile, each Radial MPLD value obtained from the facial image may be calculated as a pixel distance, and an actual distance for each Radial MPLD value may be calculated by using the radius of the pupil.

Specifically, a pixel distance corresponding to a radius of the pupil is obtained from a front facial image, and the resolution of the image is determined by considering the pixel distance corresponding to the radius of the pupil and an actual length of the radius of the pupil, and then an actual distance corresponding to the pixel distance of an Radial MPLD value may be calculated by considering the resolution of the image.

8. Capturing and Transmitting Facial Image

In a case where a patient's face is rotated left and right and/or up and down when capturing a facial image, distortion may occur in the facial image. In a case when there is distortion in the facial image, the accuracy of facial image analysis may decrease, so the patient may be provided with a photographing guide in order to obtain a preferable facial image.

The photographing guide provided to the patient may be provided from a user device. The photographing guide provided to the patient may be pre-stored on the user device. Without being limited thereto, the photographing guide may be obtained from an analysis server and provided to the patient when the patient is requested to capture an image.

The patient may capture a facial image by following the provided photographing guide, and may store the captured facial image on the user device or transmit the captured facial image to the analysis server.

This is not limited thereto, and in a case where medical staff captures a facial image, the medical staff may capture the facial image by following the provided photographing guide, and may store the captured facial image on medical staff device, a hospital server, and/or a medical server, or transmit the captured facial image to the analysis server.

The following describes a method for capturing and transmitting a facial image.

Figure 20:
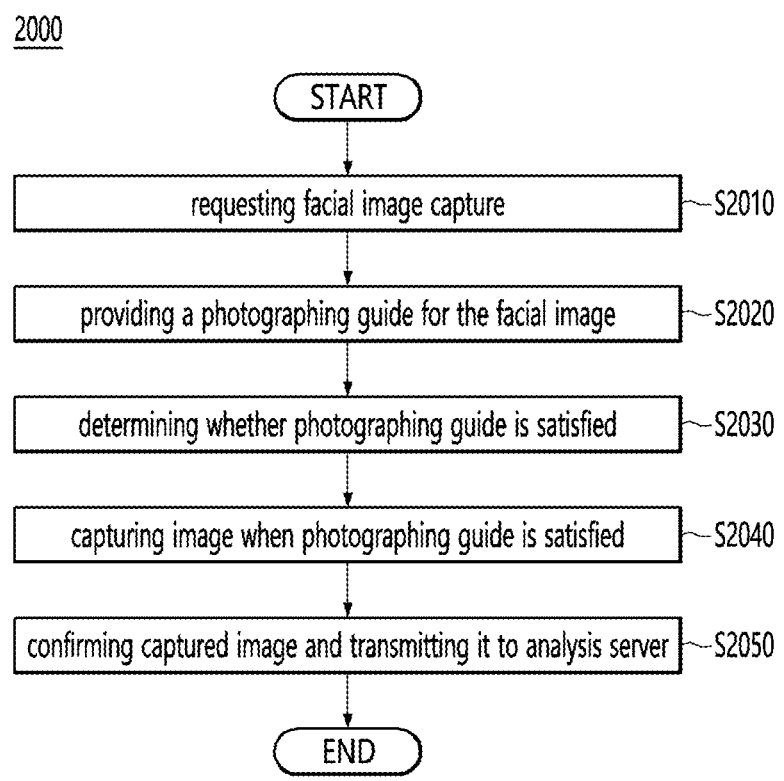
FIG. 20 is a flowchart illustrating a process of capturing and transmitting a facial image according to the exemplary embodiment.

FIG. 20 is a flowchart illustrating a process of capturing and transmitting a facial image according to the exemplary embodiment.

Referring to FIG. 20, a method 2000 for capturing and transmitting a facial image may include: step S2010 of requesting facial image capture, step S2020 of providing a photographing guide for the facial image, step S2030 of determining whether the photographing guide is satisfied or not, step S2040 of capturing the image when the photographing guide is satisfied, and step S2050 of confirming and transmitting the captured image to an analysis server.

Step S2010 of requesting the facial image capture may be a step of requesting the capturing of the facial image, which is an analysis target in order to obtain a patient's personalized estimates and patient data.

For example, the analysis server may transmit a facial image capture request to the patient's user device at a monitoring time point. As another example, when receiving a monitoring request from the patient's user device, the analysis server may transmit a facial image capture request to the patient's user device. This is not limited thereto, and the analysis server may also transmit a facial image capture request to medical staff device of a hospital, or may also transmit a facial image capture request to the medical staff device upon receiving a monitoring request from the medical staff device of the hospital. That is, step S2010 of requesting the facial image capture may be performed at the monitoring time point or may be performed at any time according to the needs of the patient and/or medical staff.

Step S2020 of providing the photographing guide for the facial image may be a step of providing the photographing guide to assist in capturing the facial image in order to obtain a preferable facial image.

For example, in a case where the patient's user device is required to capture a facial image, the patient's user device may display the photographing guide. For a specific example, a display equipped on the patient's user device may display the photographing guide along with a preview image.

The photographing guide may include text, voice, indicators, and/or graphics that guide an angle of the user device, a distance between the user device and a user's face, an angle of the face, a position of the face, a position of an eye, and/or a facial expression. In this case, whether the photographing guide is satisfied or not may be determined on the basis of whether or not the angle of the user device, the distance between the user device and the user's face, up-and-down angles of the face, left-and-right angles of the face, the position of the face in the image, the position of the eye in the image, and/or the facial expression are satisfied with criteria.

The photographing guide may include the text, voice, indicators, and/or graphics that guide whether the up-and-down angles of the face are appropriate or not, whether the face is centered or not, whether the left-and-right angles of the face are appropriate or not, whether the eye position are appropriate or not, and/or whether the facial expression is expressionless or not.

For example, a photographing guide that guides whether the up-and-down angles of the face are appropriate or not may be displayed as a horizontal line on a preview image, and a photographing guide that guides whether the left-and-right angles of the face are appropriate or not may be displayed as a vertical line on a preview image. The horizontal line may be centered on the preview image, and the vertical line may be centered on the preview image. In this case, when the up-and-down angles of the face are at appropriate angles, the color of the horizontal line on the preview image may change, and when the left-and-right angles of the face are at appropriate angles, the color of the vertical line on the preview image may change. Accordingly, the patient may easily visually check whether the photographing guide is satisfied or not.

In addition, a photographing guide that guides whether the eye position is appropriate or not may be displayed as a crosshair at an appropriate eye position on a preview image. In this case, when the eye position is at an appropriate position, the color of the crosshair on the preview image may change. Accordingly, the patient may easily visually check whether the photographing guide is satisfied or not.

In addition, a photographing guide that guides whether the eye position is appropriate or not may be displayed as an indicator and/or shape of a pupil figure near a preview image, and a photographing guide that guides whether the facial expression is expressionless or not may be displayed as an indicator and/or shape of an expressionless face figure near a preview image. In this case, when the pupil position is at an appropriate position, the color of the indicator and/or shape of the pupil figure may change, and when the facial expression is expressionless, the color of the indicator and/or shape of the expressionless face figure may change. Accordingly, the patient may easily visually check whether a photographing guide is satisfied or not.

Meanwhile, since the conditions that should be satisfied by a front facial image and a side facial image may be different from each other, a photographing guide provided for capturing the front facial image and a photographing guide provided for capturing the side facial image may be different from each other.

For example, information related to a pupil obtained from a front facial image is used in various ways in image analysis, so a photographing guide provided for capturing a front facial image may include a photographing guide for aligning the position of the pupil.

Meanwhile, in a case where medical staff device of a hospital is required to capture a facial image, the medical staff device may display a photographing guide. Specifically, a display equipped in the medical staff device may display the photographing guide along with a preview image, and since the specific details related to the photographing guide have been described above, a duplicate description is omitted.

Step S2030 of determining whether the photographing guide is satisfied or not may be a step of determining whether a preview image captured by the patient's user device satisfies the provided photographing guide or not.

For example, in a case where a photographing guide is for aligning left-and-right angles and up-and-down angles of a face, the user device may determine whether or not the angles of the face in a captured preview image is aligned in accordance with the photographing guide. For a more specific example, the user device may determine the roll, pitch, and/or yaw of the face in the captured preview image, and determine whether an angle of the face is an angle facing forward, an angle facing leftward, or an angle facing rightward on the basis of the determined result.

This is not limited thereto, and depending on what a photographing guide is intended to guide, the user device may determine whether the face in the preview image satisfies the photographing guide or not.

Step S2040 of capturing the image when the photographing guide is satisfied may be a step of capturing a facial image when the face in the preview image captured by the user device satisfies the photographing guide.

For example, the user device may determine whether the preview facial image satisfies the photographing guide as described above, and may capture the facial image in a case where the photographing guide is satisfied.

The capturing of the facial image may be performed by the patient operating a photographing interface of the user device. In this case, text, voice, and/or shape indicating that the photographing guide has been satisfied may be displayed on the user device, but it is not limited thereto.

Meanwhile, the capturing of the facial image may also be performed by the user device for automatically capturing the facial image in a case where the photographing guide is satisfied, without the patient having to operate the photographing interface of the user device.

Step S2050 of confirming the captured image and transmitting the captured image to the analysis server may be a step of confirming whether the captured facial image is a preferable facial image to be used as an analysis image, and then transmitting the captured facial image to the analysis server in a case where it is determined to be the preferable facial image.

The patient may determine whether or not the captured facial image is the preferable facial image to be used as the analysis image. For example, the patient may check the facial image captured through the user device to determine whether the angle of the face is off, whether the facial image is blurredly displayed, and/or whether an eye region is not fully displayed in the facial image. The factors considered to determine whether or not the captured facial image is the preferable facial image to be used as the analysis image are not limited to the examples described above. By considering whether the accuracy of analysis results is expected to be low when conducting image analysis by using the captured facial image, the patient may determine whether or not the captured image is the preferable facial image to be used as the analysis image.

In a case where the patient determines that the facial image is not a preferable facial image to be used as an analysis image, the patient may recapture the facial image. In this case, the user device may perform an action for recapturing the facial image. For example, the user device may delete the captured facial image and display a photographing guide for a face again, but it is not limited thereto.

In a case where the patient determines that the captured facial image is a preferable facial image to be used as an analysis image, the captured facial image may be transmitted to the analysis server through the user device.

Meanwhile, the user device may also determine whether or not the captured facial image is the preferable facial image to be used as the analysis image. For example, even though the facial image is captured after the photographing guide is deemed satisfactory, it may take time until an actual facial image is captured, so the user device may recheck whether the captured facial image satisfies the photographing guide or not, but it is not limited thereto.

In this case, in a case where the user device determines that the captured facial image is a preferable facial image to be used as an analysis image, the user device may transmit the captured facial image to the analysis server.

9. Displaying Facial Image Comparative Data

The obtained facial images of the patient may be preprocessed and displayed so as to be easily compared to each other.

Below, a method for displaying a patient's facial images is described.

Figure 21:
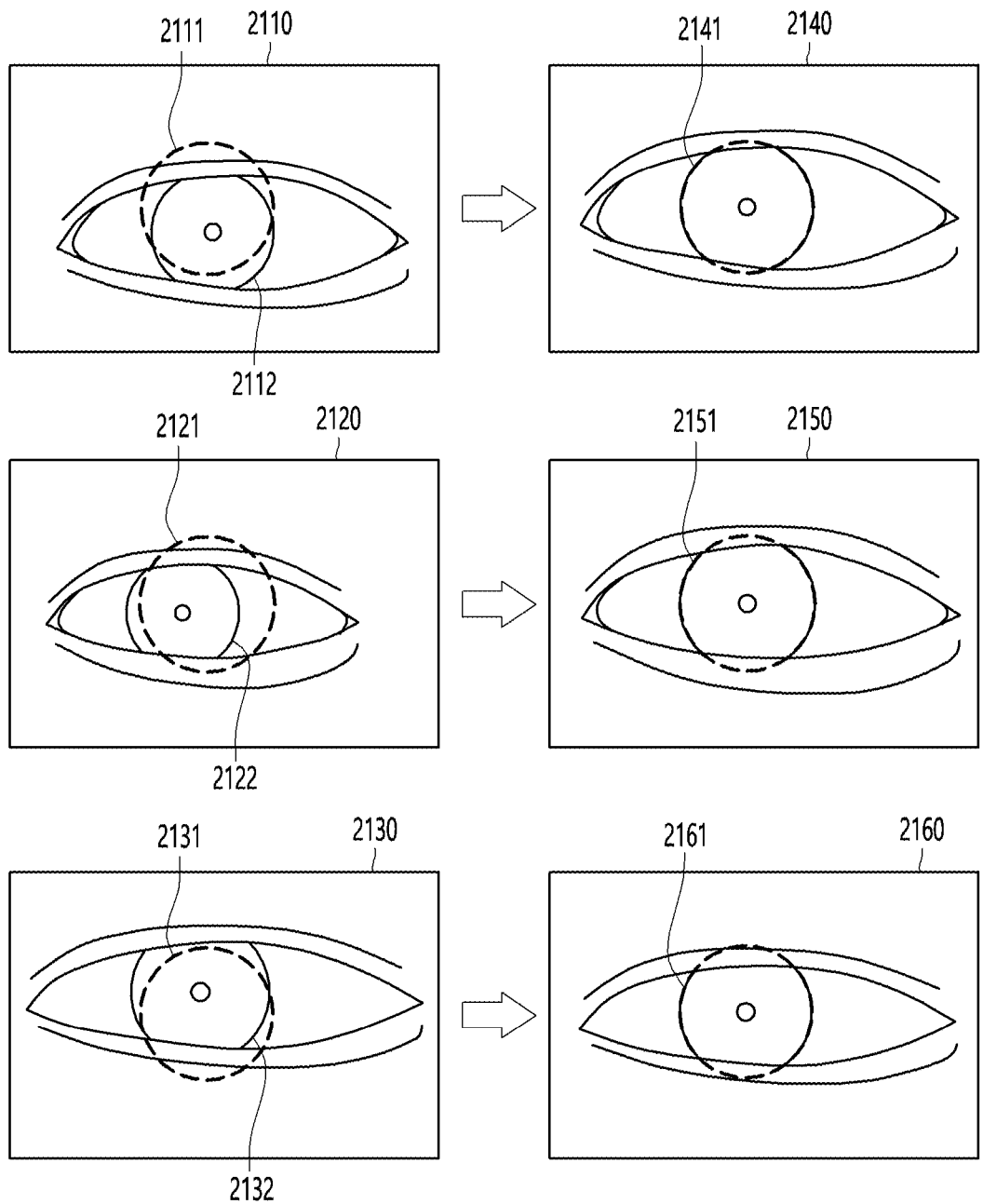
FIG. 21 is a view illustrating adjustment of a patient's facial images according to the exemplary embodiment.

FIG. 21 is a view illustrating adjustment of the patient's facial images according to the exemplary embodiment.

Referring to FIG. 21, facial images 2110, 2120, and 2130 obtained from a patient may each show the patient's eye. Since the facial images 2110, 2120, and 2130 obtained from the patient are facial images captured by the patient using a user device thereof, the eye sizes and pupil positions shown in the respective facial images 2110, 2120, and 2130 may be different from each other.

All the reference pupil positions 2111, 2121, and 2131 are respectively illustrated on the facial images 2110, 2120, and 2130 obtained from the patient together in FIG. 21. However, this is illustrated to show that the eye sizes and pupil positions in the respective facial images 2110, 2120, and 2130 are different from each other, and when the facial images 2110, 2120, and 2130 obtained from the patient are displayed on a user device and/or medical staff device, the reference pupil positions 2111, 2121, and 2131 may not be illustrated together.

Each of the reference pupil positions 2111, 2121, and 2131 may be a position with fixed coordinates relative to a frame therefor in which a facial image is displayed. Specifically, each of the reference pupil positions on the frame in which the facial image is displayed may be the position whose coordinates are fixed regardless of an actual position of a pupil as it appears on the facial image displayed.

Referring to FIG. 21, for each of the facial images 2110, 2120, and 2130 obtained from the patient, the sizes and/or positions of the facial images 2110, 2120, and 2130 may be adjusted such that the pupils 2112, 2122, and 2132 on the facial images 2110, 2120, and 2130 are respectively positioned at the reference pupil positions 2111, 2121, and 2131.

For example, a first facial image 2110 may be adjusted in size and/or position such that a pupil 2112 on the first facial image 2110 obtained from the patient is disposed at a reference pupil position 2111. A first adjusted facial image 2140 may be obtained by adjusting the size and/or position of the first facial image 2110. That is, a position 2141 of the pupil shown on the first adjusted facial image 2140 may correspond to the reference pupil position thereof.

In addition, a second facial image 2120 may be adjusted in size and/or position such that a pupil 2122 on the second facial image 2120 obtained from the patient is disposed at a reference pupil position 2121. A second adjusted facial image 2150 may be obtained by adjusting the size and/or position of the second facial image 2120. That is, a position 2151 of the pupil shown on the second adjusted facial image 2150 may correspond to the reference pupil position thereof.

In addition, a third facial image 2130 may be adjusted in size and/or position such that a pupil 2132 on the third facial image 2130 obtained from the patient is disposed at a reference pupil position 2131. A third adjusted facial image 2160 may be obtained by adjusting the size and/or position of the third facial image 2130. That is, a position 2161 of the pupil shown on the third adjusted facial image 2160 may correspond to the reference pupil position thereof.

To enable the obtained facial images to be easily compared to each other, the adjusted facial images 2140, 2150, and 2160, in which the respective positions of the pupils shown in the obtained facial images 2110, 2120, and 2130 are adjusted to the reference pupil positions, may be displayed.

For example, the adjusted facial images 2140, 2150, and 2160 may be displayed sequentially in order of starting from an adjusted facial image obtained from a facial image corresponding to the earliest time point, and ending with an adjusted facial image obtained from a facial image corresponding to the latest time point. Since the positions of the pupils of the adjusted facial images 2140, 2150, and 2160 are the same, the patient and/or medical staff may more intuitively recognize how the condition of the face changes over time in a case where the adjusted facial images 2140, 2150, and 2160 are displayed sequentially.

As another example, among the adjusted facial images, two adjusted facial images, including an adjusted facial image obtained from a facial image corresponding to the earliest time point and an adjusted facial image obtained from a facial image corresponding to the latest time point, may be displayed sequentially. This is not limited thereto, and two adjusted facial images may be displayed overlapping each other.

For a specific example, two adjusted facial images, including an adjusted facial image obtained from a facial image corresponding to a treatment start time point and an adjusted facial image obtained from a facial image corresponding to a current time point, may be displayed.

Since the two adjusted facial images, including the adjusted facial image obtained from the facial image corresponding to the earliest time point and the adjusted facial image obtained from the facial image corresponding to the latest time point, are displayed in a state of having the same pupil positions, the patient and/or medical staff may more intuitively recognize how the condition of the face has changed between the specific time points.

Figure 22:
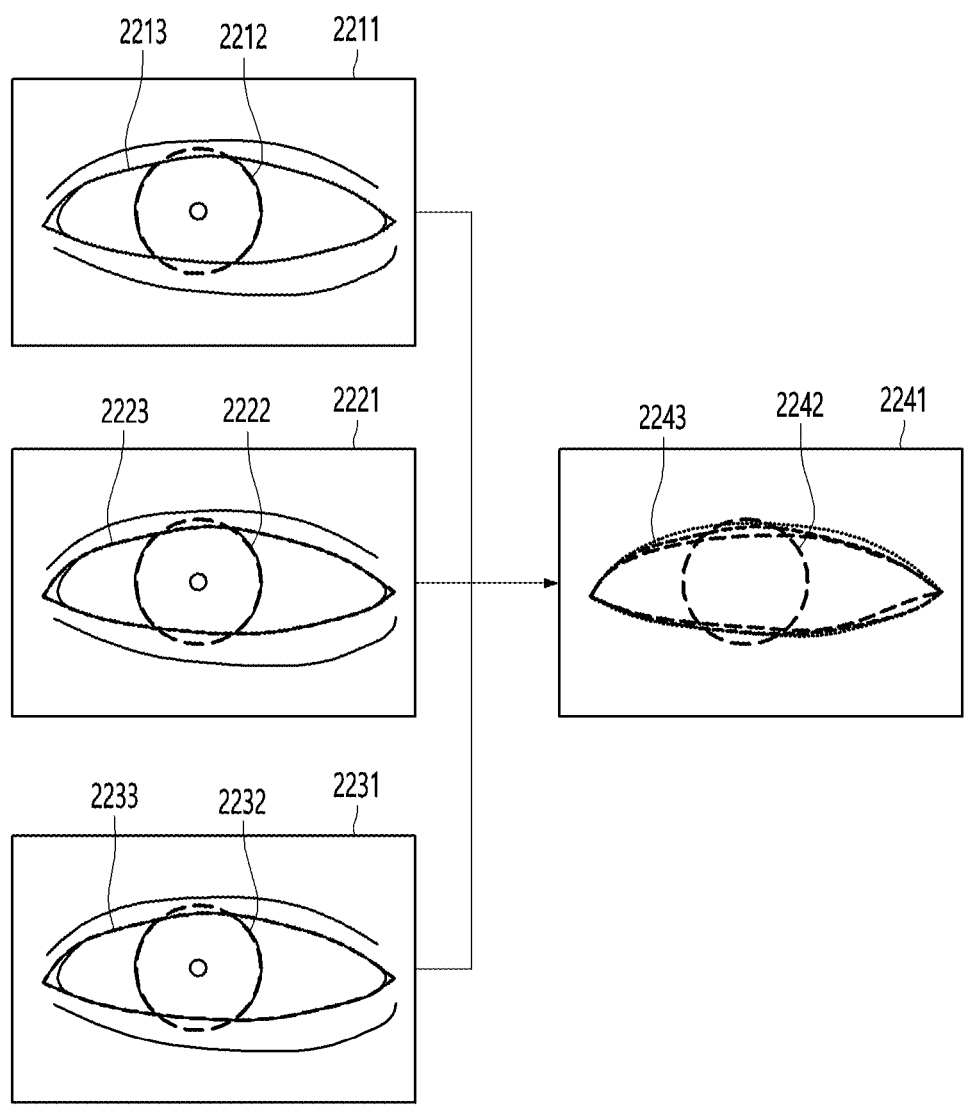
FIG. 22 is a view illustrating a method for displaying the patient's facial image according to the exemplary embodiment.

FIG. 22 is a view illustrating a method for displaying the patient's facial images according to the exemplary embodiment.

Referring to FIG. 22, eyeball outlines 2213, 2223, and 2233 may be obtained from adjusted facial images 2211, 2221, and 2231 in which respective pupil positions are adjusted to reference pupil positions 2212, 2222, and 2232.

In this case, an outline of an eyeball may mean a boundary between the eyeball and an eyelid. The eyeball outline may be obtained on the basis of image segmentation, and the specific details have been described above in the facial image-based exophthalmos degree determination method, so a duplicate description is omitted.

Specifically, referring to FIG. 22, a first eyeball outline 2213 may be obtained from a first adjusted facial image 2211 in which a pupil position is adjusted to a reference pupil position 2212. In addition, a second eyeball outline 2223 may be obtained from a second adjusted facial image 2221 in which a pupil position is adjusted to a reference pupil position 2222. In addition, a third eyeball outline 2233 may be obtained from a third adjusted facial image 2231 in which a pupil position is adjusted to a reference pupil position 2232.

To enable the obtained facial images to be easily compared to each other, the obtained eyeball outlines 2213, 2223, and 2233 may be displayed overlapping each other.

Specifically, as in FIG. 22, the eyeball outlines 2213, 2223, and 2233 obtained from facial images corresponding to a plurality of time points may be displayed in a state 2243 of overlapping each other on one image 2241.

Since the eyeball outlines 2213, 2223, and 2233 are displayed in the state 2243 of overlapping each other on the basis of a reference pupil position 2242, the patient and/or medical staff may more intuitively recognize how a condition of a face has changed.

The obtained eyeball outlines 2213, 2223, and 2233 may be displayed sequentially in order of starting from an eyeball outline obtained from a facial image corresponding to the earliest time point, and ending with an eyeball outline obtained from a facial image corresponding to the latest time point.

Since the eyeball outlines 2213, 2223, and 2233 are arranged on the basis of the reference pupil positions, the patient and/or medical staff may more intuitively recognize how the condition of the face changes over time in a case where the eyeball outlines 2213, 2223, and 2233 are displayed sequentially.

An obtained eyeball outline may be displayed on an adjusted facial image.

For example, a first eyeball outline 2213 may be displayed in a first adjusted facial image 2211, a second eyeball outline 2223 may be displayed in a second adjusted facial image 2221, and a third eyeball outline 2233 may be displayed in the third adjusted facial image 2231.

This is not limited thereto, and eyeball outlines obtained from facial images at a plurality of time points may be displayed on one facial image corresponding to one time point.

For example, the first eyeball outline 2213 and the second eyeball outline 2223 may be displayed in the first adjusted facial image 2211 or the second adjusted facial image 2221, and the first eyeball outline 2213 and the third eyeball outline 2233 may be displayed in the first adjusted facial image 2211 or the third adjusted facial image 2231.

Accordingly, an eyeball outline of a current time point and an eyeball outline of a previous time point may be displayed together on a facial image of the current time point, so that the patient and/or medical staff may more intuitively recognize how the condition of the face has changed between the specific times.

The patient's eyeball outline obtained from the patient's facial image and an averaged eyeball outline of a group to which the patient belongs may be displayed together along with the patient's facial image. In this case, the patient's eyeball outline and the averaged eyeball outline of the group to which the patient belongs may be displayed on the patient's facial image on the basis of the same reference pupil position.

The group to which the patient belongs may be distinguished by gender and/or age. For example, patients of the same gender may be recognized as belonging to the same group. As another example, patients who fall within the same age range among preset age ranges may be recognized as belonging to the same group. For a yet another example, patients of the same race may be recognized as belonging to the same group, and each group to which the patients belongs is not limited to the examples described above.

Since the obtained patient's eyeball outline and the averaged eyeball outline of the group to which the patient belongs may be displayed together on the patient's facial image, the patient and/or the medical staff may intuitively recognize how much the patient's facial condition differs compared to the averaged one.

An area corresponding to deviations between the patient's eyeball outline obtained from the patient's facial image and the eyeball outlines of the group to which the patient belongs may be displayed together on the patient's facial image. In this case, the area corresponding to the deviations between the patient's eyeball outline and the eye outlines of the group to which the patient belongs may be displayed on the patient's facial image on the basis of the same reference pupil position.

Since the area corresponding to the deviations between the patient's obtained eyeball outline and the eye outlines of the group to which the patient belongs may be displayed together on the patient's facial image, the patient and/or medical staff may intuitively recognize a level at which the patient's facial condition is positioned.

10. Clinical Trial Monitoring

In a clinical trial, a medicine may be administered to each of a plurality of patients, and the effectiveness of medicine in the plurality of patients may be monitored during a monitoring period.

In the existing clinical trials, patient data is able to be obtained only when a patient visited a hospital. That is, only limited clinical trial data may be obtained, so the existing clinical trial results may only be used to a limited extent for research and/or development of drugs.

Accordingly, in the clinical trials, a monitoring method for obtaining more data is required.

Figure 23:
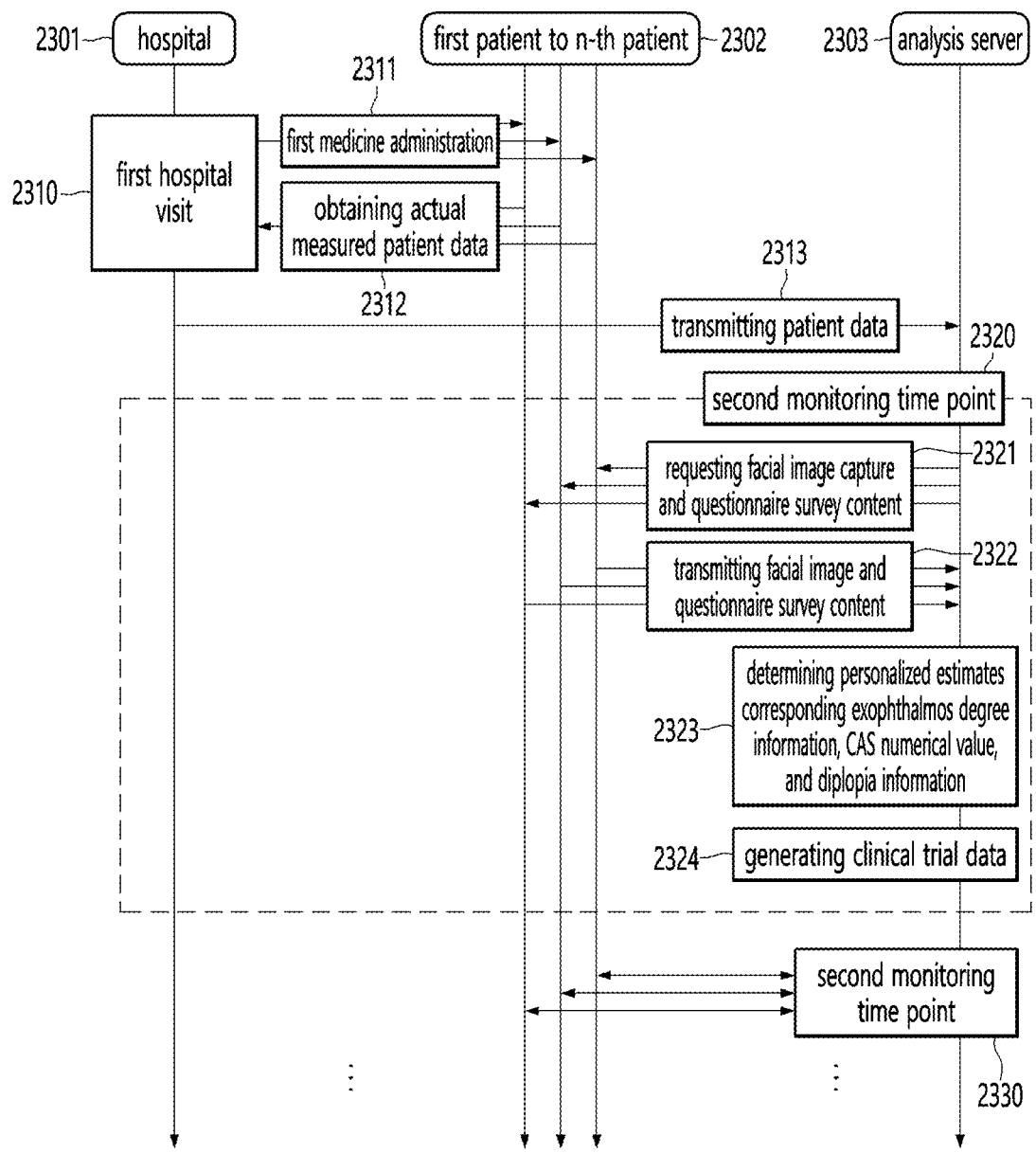
FIG. 23 is a view illustrating a method for monitoring the effectiveness of medicine in a clinical trial according to the exemplary embodiment.

FIG. 23 is a view illustrating a method for monitoring the effectiveness of medicine in a clinical trial according to the exemplary embodiment.

Referring to FIG. 23, each of a plurality of patients 2302 may be administered a medicine when visiting a hospital 2301. Specifically, when each of the plurality of patients 2302 visits the hospital 2301, medical staff assigned at the hospital 2301 may administer a medicine to each of the plurality of patients 2302. Hereinafter, it may be understood that a process of administering a medicine to a patient when visiting a hospital is carried out by medical staff assigned at the hospital.

The medicine may be a medicine for which a clinical trial is intended to be conducted. For example, the medicine may be a medicine for the purpose of treating thyroid ophthalmopathy, and the clinical trial may be a trial to verify whether the medicine is effective or not in treating the thyroid ophthalmopathy. In this case, the treatment effectiveness for thyroid ophthalmopathy may be alleviation of exophthalmos, improvement of CAS numerical values, and/or alleviation of diplopia. Meanwhile, the medicine may be a medicine of which the administration is required a plurality of times during a clinical trial period.

The hospital 2301 may mean a hospital with medical staff assigned thereat. Meanwhile, the actions performed by the hospital 2301 may be understood as to be performed by the medical staff assigned at the hospital, a hospital server, medical staff server, and/or medical staff device, and a duplicate description will be omitted hereinafter.

The plurality of patients 2302 may be clinical trial subjects, i.e., each patient administered a placebo or a medicine for the purpose of treating thyroid ophthalmopathy. Hereinafter, each patient administered the placebo may also undergo the same monitoring as each patient administered the medicine does, and thus the patients each administered the medicine may include the patients each administered the placebo as well as the patients administered the medicine for the purpose of treating thyroid ophthalmopathy. Meanwhile, the actions performed by the patient 2302 below may be understood as being performed by the patient and/or the patient's user device, and a duplicate description is omitted below.

Referring to FIG. 23, each of the plurality of patients 2302 may receive administration 2311 of a first medicine during a first visit 2310 to a hospital 2301, and the hospital 2301 may obtain actual measured patient data 2312 for each of the plurality of patients 2302. Specifically, when each of the plurality of patients 2302 makes the first visit 2310 to the hospital 2301, medical staff assigned at the hospital 2301 may administer the first medicine to each of the plurality of patients 2302, and the medical staff assigned at the hospital 2301 may perform obtaining 2312 actual measured patient data from each of the plurality of patients 2302. Below, the process of obtaining, by the hospital, the patient data when each patient visits the hospital may be understood as being performed by the medical staff assigned at the hospital.

In addition, the hospital 2301 may perform transmitting 2313 the obtained patient data to an analysis server 2303. Specifically, the hospital server, the medical staff server, and/or the medical staff device, which are disposed in the hospital 2301, may perform the transmitting 513 the patient data to the analysis server 2303. Hereinafter, the process of transmitting, by the hospital, data to the analysis server may be understood as being performed by the hospital server, the medical staff server, and/or the medical staff device, which are disposed in the hospital.

The analysis server 2303 may be a device that performs data transmission and reception with the hospital 2301 and the plurality of patients 2302, obtains patient data about the plurality of patients 2302, determines and/or estimates the condition of each of the plurality of patients 2302, and provides the determined and/or estimated patient data to the hospital 2301 and/or the plurality of patients 2302.

The patient data transmitted to the analysis server 2303 by the hospital 2301 may include exophthalmos degree measurement values, a facial image of each patient at the time of measuring an exophthalmos degree, thyroid dysfunction management history, thyroid ophthalmopathy treatment information, patient physical information, patient health information, and the like, which are obtained from each of the plurality of patients 2302.

Each exophthalmos degree measurement value may be an actual measured exophthalmos degree value obtained directly from the patient by the medical staff. This is not limited thereto, and may also be an exophthalmos degree value estimated from the patient's facial image captured when the patient visits the hospital.

The patient's thyroid dysfunction management history may include: a diagnosis name of thyroid dysfunction, a time point of thyroid dysfunction diagnosis, blood test results, information on surgery and/or procedures due to a thyroid dysfunction, the type, dosage, and/or dose period of a medicine administered for treating thyroid dysfunction, but it is not limited thereto.

A thyroid dysfunction may indicate hypothyroidism, but this should not be limited thereto, and the thyroid dysfunction may be understood to include symptoms related to the thyroid dysfunction. Specifically, the symptoms related to the thyroid dysfunction may include hypothyroidism, thyroiditis, and/or thyroid nodules, but this is not limited to the examples described herein.

The blood test results may include hormone levels and antibody levels.

The hormone levels may be numerical values for hormones related to hyperthyroidism. For example, the hormones related to the hyperthyroidism may include Free T4, TSH, Free T3, and/or Total T3, but it is not limited thereto.

The antibody levels may be numerical values for antibodies related to the hyperthyroidism. For example, the antibodies related to the hyperthyroidism may include Anti-TSH receptor Ab, Anti-TPO Ab, and/or Anti-Tg Ab, but it is not limited thereto.

In addition, the blood test results may also include numerical values of thyroglobulin (TG) and thyroxine-binding globulin (TBG).

The thyroid ophthalmopathy treatment information may include: the type, dosage, and dose period of a medicine administered for treating thyroid ophthalmopathy, a steroid prescription date, a steroid prescription dose, a radiation treatment date, a thyroid ophthalmopathy surgery date, and/or a triamcinolone administration date, but it is not limited thereto.

The patient physical information and patient health information may include information based on the patient's physical characteristics, such as the patient's age, gender, race, and weight, but it is not limited thereto.

Meanwhile, in FIG. 23, it is shown that the hospital 2301 performs transmitting 2313 the patient data to the analysis server 2303 after administering 2311 the medicine to each of the plurality of patients 2302, but it is not limited thereto, and the hospital 2301 may also transmit the patient data to the analysis server 2303 before administering the medicine to each patient 2302.

Referring to FIG. 23, patient monitoring may be performed at each second monitoring time point 2320.

A second monitoring time point 2320 according to the exemplary embodiment may be a time point during a period in which each of the plurality of patients 2302 visits the hospital 2301 in order to be administered the medicine. Specifically, the second monitoring time point 2320 may be a time point within a clinical trial period when each of the plurality of patients 2302 visits the hospital 2301 in order to be administered all the medicines of which the administration is required a plurality of times.

In addition, the second monitoring time point 2320 may be a time point within the clinical trial period when each of the plurality of patients 2302 visits the hospital 2301 for condition observation after being administered all the medicines of which the administration is required the plurality of times.

In addition, the second monitoring time point 2320 may be a time point within a period that further includes a certain period of time after each of the plurality of patients 2302 is administered all the medicines of which the administration is required the plurality of times. In this case, the certain period of time may be one year, but it is not limited thereto.

The second monitoring time point 2320 may be a time point within a period that further includes a certain period of time after all the medicines have been administered, so that it may be confirmed whether the treatment effectiveness has disappeared and/or whether side effects have occurred after the medicine administration have ended. In this case, the certain period of time may be determined according to a clinical trial design.

The second monitoring time point 2320 according to the exemplary embodiment may be determined on the basis of a preset clinical trial monitoring cycle.

In this case, the clinical trial monitoring cycle may be set according to the clinical trial design.

For example, the clinical trial monitoring cycle may be set according to how much clinical trial data is required to be obtained. Specifically, the clinical trial monitoring cycle may be set according to how much clinical trial data a pharmaceutical company of the medicine needs to obtain and how much clinical trial data needs to be obtained during a clinical trial period.

As another example, the clinical trial monitoring cycle may be set to perform monitoring a set number of times between medicine administration depending on the clinical trial design. For example, in a case where a medicine is administered at three-week intervals, the clinical trial monitoring cycle may be set so that monitoring is performed at one-week intervals, but it is not limited thereto.

Meanwhile, the clinical trial monitoring cycle may be set so that monitoring is performed at specific intervals. For example, the clinical trial monitoring cycle may be set so that monitoring is performed at two-day intervals, but it is not limited thereto and a specific period may be freely determined.

Meanwhile, a specific action performed at the second monitoring time point 2320 will be described after describing FIG. 19.

Figure 24:
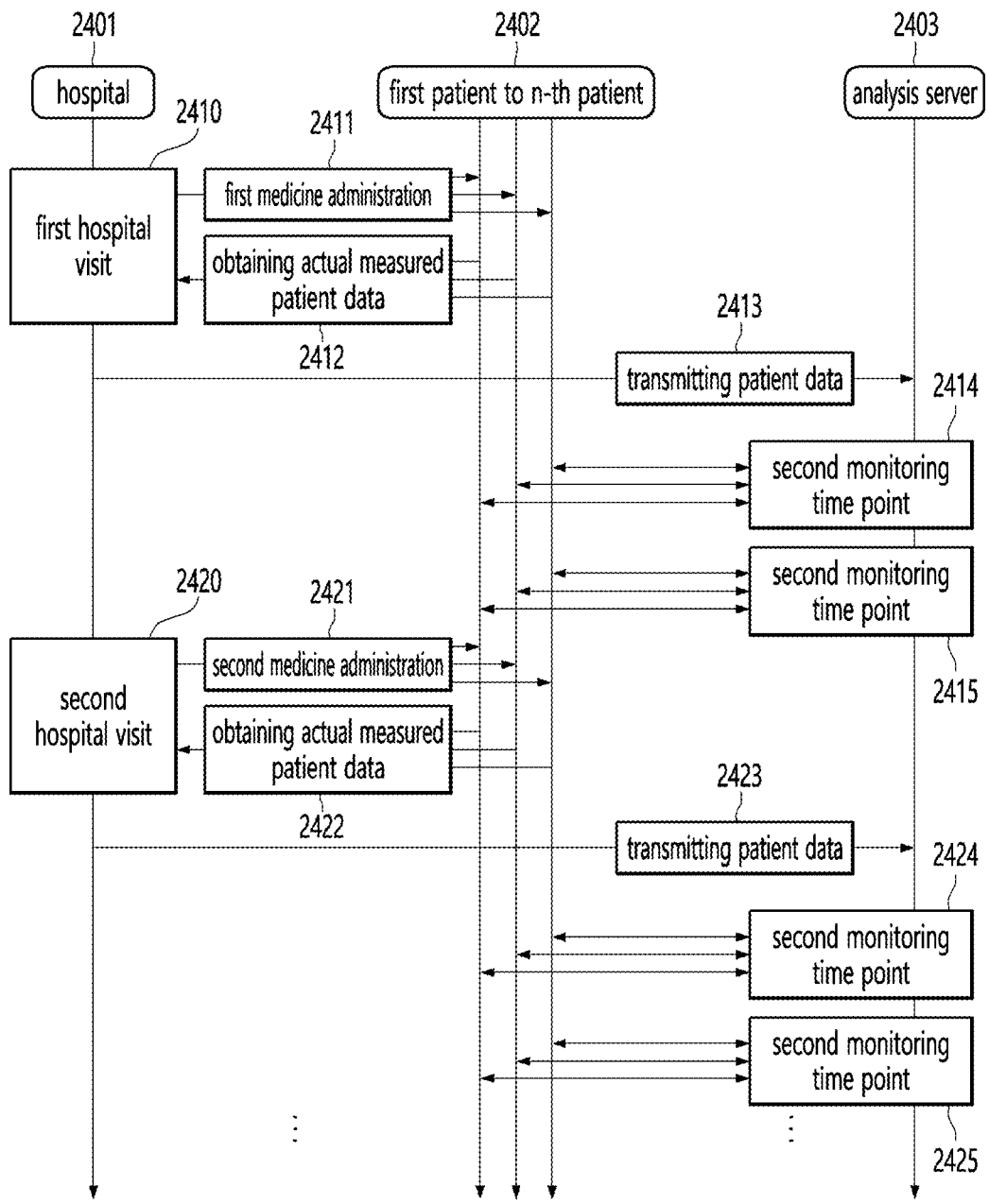
FIG. 24 is a view illustrating an overall method for monitoring the effectiveness of medicine in the clinical trial according to the exemplary embodiment.

FIG. 24 is a view illustrating an overall method for monitoring the effectiveness of medicine in a clinical trial according to the exemplary embodiment.

Referring to FIG. 24, each of a plurality of patients 2402 may be administered a medicine when visiting a hospital 2401. Specifically, when each of the plurality of patients 2402 visits the hospital 2401, medical staff assigned at the hospital 2401 may administer the medicine to each of the plurality of patients 2402. Hereinafter, it may be understood that a process of administering the medicine to each patient when visiting the hospital is carried out by the medical staff assigned at the hospital.

The medicine may be a medicine for which a clinical trial is being conducted. For example, the medicine may be a medicine for the purpose of treating thyroid ophthalmopathy, and the clinical trial may be a trial to verify whether the medicine is effective in treating the thyroid ophthalmopathy. A medication administration regimen may be determined on the basis of a clinical trial design.

Meanwhile, the above-described details of the hospital 2301, plurality of patients 2302, and analysis server 2303 in FIG. 23 may be applied to the hospital 2401, plurality of patients 2402, and analysis server 2403 in FIG. 24, so a duplicate description is omitted.

Referring to FIG. 24, each of the plurality of patients 2402 may receive administration 2411 of a first medicine at a time point 2410 of his or her first visit to the hospital 2401, and the hospital 2401 may perform obtaining 2412 actual measured patient data from each of the plurality of patients 2402. Specifically, when each of the plurality of patients 2402 makes the first visit at the time point 2410 to the hospital 2401, the medical staff assigned at the hospital 2401 may administer the first medicine to each of the plurality of patients 2402, and the medical staff assigned at the hospital 2401 may perform obtaining 2412 the actual measured patient data from each patient 2402. Below, the process of obtaining, by the hospital, the patient data when the patient visits the hospital may be understood as being performed by the medical staff assigned at the hospital.

In addition, the hospital 2401 may perform transmitting 2413 the obtained patient data to the analysis server 2403. Specifically, a hospital server, medical staff server, and/or medical staff device, which are disposed in the hospital 2401 may perform transmitting 2413 the patient data to the analysis server 2403. Hereinafter, the process of transmitting, by the hospital, data to the analysis server may be understood as being performed by the hospital server, the medical staff server, and/or the medical staff device, which are disposed in the hospital.

The details related to the hospital 2401 transmitting the patient data to the analysis server 2403 may be applied to the details described above in the description where the hospital 2401 performs transmitting 2313 the patient data to the analysis server 2403 in FIG. 23, so a duplicate description is omitted.

Referring to FIG. 24, monitoring for each of the plurality of patients may be performed at a second monitoring time point 2414 given for the first time after the time point 2410 of the first hospital visit, and patient monitoring may be performed at a second monitoring time point 2415 given for the second time after the second monitoring time point 2414 given for the first time. With regard to determining the second monitoring time point, the details described above in the description where the second monitoring time point 2320 is determined in FIG. 23 may be applied, so a duplicate description is omitted.

Referring to FIG. 24, after the second monitoring time point 2415 given for the second time, each of the plurality of patients 2402 may make a second visit 2420 to the hospital 2401 and receive administration 2421 of a second medicine, and the hospital 2401 may obtain actual measured patient data 2422 from each of the plurality of patients 2402.

Items of actual measured patient data obtained at the time point 2420 of the second hospital visit and the actual measured patient data obtained at the time point 2410 of the first hospital visit may be the same with each other, but it is not limited thereto. Some of data items may be the same and some may be different, or the data items may also be different from each other. For example, the actual measured patient data obtained at the time point 2410 of the first hospital visit may include an exophthalmos degree measurement value obtained from each of the plurality of patients 2402, a facial image of the patient at a time point of exophthalmos degree measurement, thyroid dysfunction management history, patient physical information, and patient health information. The actual measured patient data obtained at the time point 2420 of the second hospital visit may include only the exophthalmos degree measurement value obtained from each of the plurality of patients 2402 and a facial image of the patient at a time point of exophthalmos degree measurement. That is, the thyroid dysfunction management history, the patient physical information, and the patient health information, which are obtained at the time point 2410 of the first hospital visit may be used as is, as the thyroid dysfunction management history, patient physical information, and patient health information of each of the plurality of patients' 2402 at the time point 2420 of the second hospital visit, and the data items are not limited to the examples described above.

The hospital 2401 may perform transmitting 2423 the obtained patient data to the analysis server 2403.

The items of the patient data transmitted to the analysis server 2403 by the hospital 2401 at the time point 2420 of the second hospital visit and the patient data transmitted to the analysis server 2403 by the hospital 2401 at the time point 2410 of the first hospital visit may be the same with each other, but it is not limited thereto. Some of the data items may be the same and some may be different, or the data items may also be different from each other. For example, the patient data transmitted to the analysis server 2403 by the hospital 2401 at the time point 2410 of the first hospital visit may include an exophthalmos degree measurement value obtained from the each of the plurality of patients 2402, a facial image of the patient at a time point of exophthalmos degree measurement, thyroid dysfunction management history, patient physical information, and patient health information. The patient data transmitted to the analysis server 2403 by the hospital 2401 at the time point 620 of the second hospital visit may include only an exophthalmos degree measurement value obtained from the each of the plurality of patients 2402 and a facial image of the patient at a time point of exophthalmos degree measurement. That is, the analysis server 2403 may use the thyroid dysfunction management history, the patient physical information, and the patient health information, which are obtained at the time point 2410 of the first hospital visit as is, as the thyroid dysfunction management history, the patient physical information, and the patient health information of each of the plurality of patients' 2402 corresponding to the time point 2420 of the second hospital visit, and the data items are not limited to the examples described above.

Meanwhile, in FIG. 24, it is illustrated such that there are two second monitoring time points 2414 and 2415 between the time point 2410 of the first hospital visit and the time point 2420 of the second hospital visit, but the number of second monitoring time points is not limited thereto, and the second monitoring time points may be arranged at various times on the basis of a set monitoring cycle. For example, there may be one second monitoring time point between the time point 2410 of the first hospital visit and the time point 2420 of the second hospital visit, or there may be three or more second monitoring time points.

Referring to FIG. 24, after the time point 2420 of the second hospital visit, patient monitoring may be performed at a second monitoring time point 2424 given for the third time, and patient monitoring may be performed at a second monitoring time point 2425 given for the fourth time.

Thereafter, hospital visits and each second monitoring may be performed repeatedly.

Referring back to FIG. 23, at the second monitoring time point 2320, each of the plurality of patients 2302 may be requested to capture a facial image and fill out questionnaire survey content.

In this case, a subject requested to capture the facial image and fill out the questionnaire survey content may be a user device of each of the plurality of patients 2302. Hereinafter, the process where the patient is requested to capture the facial image and fill out the questionnaire survey content may be understood to be performed on the user device.

Each of the plurality of patients 2302 may capture a facial image and transmit the facial image in response to a facial image capture request. For example, each of the plurality of patients 2302 may capture a facial image in response to the facial image capture request 2321 from the analysis server 2303 and transmit the facial image to the analysis server 2303.

In this case, the facial image may mean a front facial image and/or side facial image of a patient, but it is not limited thereto, and the facial image may include: a panoramic image from the front to the side of the patient; a video obtained by recording the face; and/or a facial image at any angle between the front and the side of the patient. For a more specific example, each of the plurality of patients 2302 may capture the facial image in response to the facial image capture request 2321 from the analysis server 2303 by using a user device, and perform transmitting 2322 the facial image to the analysis server 2303 through the user device. Below, it may be understood that the process of capturing, by the patient, the facial image and transmitting the facial image to the analysis server is performed by using the user device.

Meanwhile, in a case where the patient's face is rotated left and right and/or up and down when a facial image is captured, distortion may occur in the facial image. In a case when there is the distortion in the facial image, the accuracy of facial image analysis may decrease, so each of the plurality of patients 2302 may be provided with a photographing guide in order to obtain a preferable facial image. By capturing the facial image following the photographing guide, the patient 402 may capture the facial image with the same composition each time a facial image is captured. The specific details related to the photographing guide are described in 8. Capturing and transmitting facial image, so a duplicate description is omitted.

Meanwhile, since facial appearance may change depending on the time of day, each of the plurality of patients 2302 may also receive a facial image capture request at a preset image capturing time.

On the other hand, since facial appearance may change depending on the time of day, each of the plurality of patients 2302 may also be requested to capture his or her facial image at a plurality of time points different from each other during the day. In this case, analysis results for each of the obtained facial images may be obtained, and an average value and the like of the obtained analysis results may be determined as a value of correction for that day. Alternatively, an analysis result with the highest accuracy among the analysis results for each of the obtained facial images may also be determined as the value for that day. Alternatively, an analysis result for a facial image, which best satisfies the photographing guide, among the obtained facial images may also be determined as the value for that day.

On the other hand, each of the plurality of patients 502 may also receive a facial image capture request for capturing multiple facial images at a time point of facial image capture. In this case, analysis results for each of the obtained facial images may be obtained, and an average value, a median value, or the like of the obtained analysis results may be determined as the value of correction at that time point. Alternatively, an analysis result with the highest accuracy among the analysis results for each of the obtained facial images may also be determined as the value for that time point. Alternatively, an analysis result for a facial image, which best satisfies the photographing guide, among the obtained facial images may also be determined as the value for that time point.

On the other hand, each of the plurality of patients 2302 may also receive a facial image capture request for capturing a facial video at a time point of facial image capture. In this case, analysis results for each frame included in the obtained facial video may be obtained, and an average value, a median value, or the like of the obtained analysis results may be determined as a value of correction at that time point. Alternatively, an analysis result with the highest accuracy among the analysis results for each of frames included in the obtained facial video may also be determined as the value for that time point. Alternatively, an analysis result for a frame, which best satisfies the photographing guide, among the frames included in the obtained facial video may also be determined as the value at that time point.

As described above, as each of the plurality of patients 2302 receives the facial image capture request, influence of changes in the patient's facial appearance, the influence of changes occurring depending on the degree to which the patient exerts force on his or her face during the facial image capture, the patient's condition, the patient's intention, and the like, may be reduced.

Each of the plurality of patients 2302 may fill out questionnaire survey content and transmit the questionnaire survey content in response to a questionnaire survey content request. For example, each of the plurality of patients 2302 may fill out questionnaire survey content in response to the questionnaire survey content request 2321 from the analysis server 2303 and perform transmitting 2322 the questionnaire survey content to the analysis server 2303. For a more specific example, each of the plurality of the patients 2302 may fill out the questionnaire survey content by using the user device in response to the questionnaire survey content request 2321 from the analysis server 2303, and transmit the written questionnaire survey results to the analysis server 2303 through the user device. Below, it may be understood that the process of filling out, by the patient, the questionnaire survey content and transmitting the questionnaire survey results to the analysis server is performed by using the user device.

In filling out questionnaire survey content, the questionnaire survey content may be filled out in a manner of entering, by a patient, text into a user device for preset questionnaire survey items and/or in a manner of checking separate check boxes. This is not limited thereto, and in addition to the preset questionnaire survey items, the questionnaire survey content may also be filled out in a manner of entering, by the patient into the user device, content that he or she desires to transmit to the analysis server 2303 and/or the hospital 2301.

The questionnaire survey content requested from the patient 2302 may include: questionnaire survey content related to determining thyroid ophthalmopathy activity; and questionnaire survey content related to determining thyroid ophthalmopathy severity.

For example, the questionnaire survey content related to the determining of the thyroid ophthalmopathy activity may include whether there is spontaneous pain in a posterior part of an eye and whether there is pain during eye movement, but it is not limited thereto.

For example, the questionnaire survey content related to the determining of the thyroid ophthalmopathy severity may include whether diplopia is present or not and the content of quality-of-life questionnaire (Go-QoL), but it is not limited thereto.

In addition, the questionnaire survey content for which each of the plurality of patients is requested may include questionnaire survey content about signs and/or symptoms associated with side effects.

To this end, each of the plurality of patients 2302 may be provided with information related to the side effects before being requested to fill out questionnaire survey content related to the side effects.

The information related to the side effects may include information on the possible occurrence of whether muscle cramps are present or not, whether nausea is present or not, whether hair loss is present or not, whether diarrhea is present or not, whether fatigue is present or not, and/or whether hyperglycemia is present or not, but it is not limited thereto.

Based on the facial images and questionnaire survey content obtained from each of the plurality of patients 2302, personalized estimates of each of the plurality of patients 2302 regarding information intended to be proven as the effectiveness of medicine through a clinical trial may be obtained.

Specifically, referring to FIG. 23, the analysis server 2303 may perform determining 2323 personalized estimates of each of the plurality of patients 2302 for information that is intended to be proven as the effectiveness of medicine through the clinical trial by using facial images and questionnaire survey content, which are obtained from each of the plurality of patients 2302. More specifically, the analysis server 2303 may perform the determining 2323 of the personalized estimates of each of the plurality of patient 2302 for the information proven as the effectiveness of medicine through the clinical trial of the medicine for the purpose of treating thyroid ophthalmopathy by using the facial images and questionnaire survey content, which are obtained from the plurality of patients 2302. Below, the facial images and questionnaire survey content obtained from the patients may be understood as the facial images and questionnaire survey content received from each patient's user device.

The information intended to be proven as the effectiveness of medicine through the clinical trial may include alleviation of exophthalmos degrees, improvement in CAS numerical values, and/or improvement in diplopia. Accordingly, the personalized estimates for each of the plurality of patients 2302 may include exophthalmos degree information, CAS information, and/or diplopia information.

This is not limited thereto, and the personalized estimates for each of the plurality of patients 2302 may include information related to eyelid retraction and/or information related to thyroid ophthalmopathy severity.

A numerical value shown in a facial image obtained from each of the plurality of patients 2302 may be obtained as a personalized estimate for the exophthalmos degree information of each of the plurality of patients 2302. For example, the analysis server 2303 may determine an exophthalmos numerical value shown in the facial image obtained from each of the plurality of patients 2302 as the personalized estimate of the exophthalmos degree information for each of the plurality of patients 2302. The specific method for determining the exophthalmos numerical value by using the facial image has been described above in 4. Treatment process monitoring and 5. Facial image-based exophthalmos degree determination method, so a duplicate description is omitted.

Meanwhile, a trend in exophthalmos degrees may be obtained on the basis of facial images obtained from each of the plurality of patients 2302 as a personalized estimate of exophthalmos degree information for each of the plurality of patients 2302. For example, the analysis server 2303 may determine the trend in the exophthalmos degrees based on the facial images obtained from each of the plurality of patients 2302 as the personalized estimate of exophthalmos degree information for each of the plurality of patients 2302. The specific method for determining exophthalmos numerical values by using facial images has been described above in 4. Treatment process monitoring and 6. Facial image-based exophthalmos degree trend determination method, so a duplicate description is omitted.

As a personalized estimate of CAS information for each of the plurality of patients 2302, a CAS numerical value may be obtained on the basis of a facial image and questionnaire survey content obtained from each of the plurality of patients 2302. For example, the analysis server 2303 may determine the CAS numerical value by using the facial image and questionnaire survey content obtained from each of the plurality of patients 2302 as the personalized estimate of the CAS information for each of the plurality of patients 2302. The specific method for determining the CAS numerical value based on the facial image and questionnaire survey content has been described in 2. Thyroid ophthalmopathy activity and 4. Treatment process monitoring, so a duplicate description is omitted.

Meanwhile, as a personalized estimate of the CAS information for each of the plurality of patients 2302, a trend of CAS may be obtained on the basis of the facial images and questionnaire survey content obtained from each of the plurality of patients 2302. For example, the analysis server 2303 may determine the trend in CAS by using the facial images and questionnaire survey content obtained from each of the plurality of patients 2302 as the personalized estimate of the CAS information for each of the plurality of patients 2302. The specific method for determining the trend in CAS based on the facial images and questionnaire survey content has been described above in 2. Thyroid ophthalmopathy activity and 4. Treatment process monitoring, so a duplicate description is omitted.

As a personalized estimate of the diplopia information for each of the plurality of patients 2302, a diplopia presence/absence determination value may be obtained on the basis of questionnaire survey content obtained from each of the plurality of patients 2302. For example, the analysis server 2303 may obtain the diplopia presence/absence determination value by using the questionnaire survey content obtained from each of the plurality of patients 2302 as the personalized estimate of each of the plurality of patients 2302 for the diplopia information.

The diplopia presence/absence determination value may be a value indicating either the presence of diplopia or the absence of diplopia. Meanwhile, in a case of determining whether diplopia is present or not by using the Gorman criteria, the diplopia presence/absence determination value may be a value indicating one of values for no diplopia, intermittent diplopia, diplopia at extreme gaze, and persistent diplopia.

The specific method for obtaining the diplopia presence/absence determination value on the basis of the questionnaire survey content has been described in 4. Treatment process monitoring, so a duplicate description is omitted.

Meanwhile, a trend in diplopia may be obtained on the basis of the questionnaire survey content obtained from each of the plurality of patients 2302 as a personalized estimate of each of the plurality of patients 2302 for the diplopia information. For example, the analysis server 2303 may determine the trend in diplopia on the basis of the questionnaire survey content obtained from each of the plurality of patients 2302 as the personalized estimate of each of the plurality of patients 2302 for the diplopia information. The specific method for determining the trend in diplopia on the basis of the questionnaire survey content has been described in 4. Treatment process monitoring, so a duplicate description is omitted.

A personalized estimate of eyelid retraction information for each of the plurality of patients 2302 may be obtained on the basis of a facial image obtained from each of the plurality of patients 2302. For example, the analysis server 2303 may determine the personalized estimate of the eyelid retraction information for each of the plurality of patients 2302 by using the facial image obtained from each of the plurality of patients 2302.

A numerical value of eyelid retraction shown in a facial image obtained from each of the plurality of patients 2302 may be obtained as a personalized estimate of eyelid retraction information for each of the plurality of patients 2302. For example, the analysis server 2303 may determine the numerical value of eyelid retraction shown in the facial image obtained from each of the plurality of patients 2302 as the personalized estimate of the eyelid retraction information for each of the plurality of patients 2302. The specific method for determining the eyelid retraction numerical value by using the facial image has been described above in 7. Facial image-based eyelid retraction determination method, so a duplicate description is omitted.

Meanwhile, a trend in eyelid retraction may be obtained on the basis of facial images obtained from each of the plurality of patients 2302 as a personalized estimate of eyelid retraction information for each of the plurality of patients 2302. For example, the analysis server 2303 may determine the trend of eyelid retraction on the basis of the facial images obtained from each of the plurality of patients 2302 as the personalized estimate of the eyelid retraction information for each of the plurality of patients 2302. The specific method for determining the trend of eyelid retraction by using the facial images has been described in 4. Treatment process monitoring and 7. Facial image-based eyelid retraction determination method, so a duplicate description is omitted.

A personalized estimate of thyroid ophthalmopathy severity information for each of the plurality of patients 2302 may be obtained on the basis of a facial image and questionnaire survey content obtained from each of the plurality of patients 2302. For example, the analysis server 2303 may determine the personalized estimate of each of the plurality of patients 2302 for the thyroid ophthalmopathy severity information by using the facial image and questionnaire survey content obtained from each of the plurality of patients 2302. In this case, the thyroid ophthalmopathy severity information may include none, mild (moderate), and severe (serious) of the thyroid ophthalmopathy severity, but it is not limited thereto. The specific method for obtaining the personalized estimate of the thyroid ophthalmopathy severity on the basis of the facial image and questionnaire survey content has been described in 3. Thyroid ophthalmopathy severity and 4. Treatment process monitoring, so a duplicate description is omitted.

Meanwhile, a trend in thyroid ophthalmopathy severities may be obtained on the basis of facial images and questionnaire survey content obtained from each of the plurality of patients 2302 as a personalized estimate of the thyroid ophthalmopathy severity for each of the plurality of patients 2302. For example, the analysis server 2303 may determine the trend in the thyroid ophthalmopathy severities on the basis of the facial images and questionnaire survey content obtained from each of the plurality of patients 2302 as the personalized estimate of thyroid ophthalmopathy severity for each of the plurality of patients 2302. The specific method for determining the trend of thyroid ophthalmopathy severities on the basis of the facial images and questionnaire survey content has been described in 3. Thyroid ophthalmopathy severity and 4. Treatment process monitoring, so a duplicate description is omitted.

Side effect occurrence information may be obtained for each of the plurality of patients 2302 on the basis of questionnaire survey content obtained from each of the plurality of patients 2302, For example, the analysis server 2303 may determine whether side effects occurs or not for each of the plurality of patients 2302 by using the questionnaire survey content obtained from each of the plurality of patients 2302.

In this case, in a case where it is determined that side effects have occurred in at least some of the plurality of patients 2302, a pharmaceutical company may be notified of side effect occurrence information. For example, in a case where the analysis server 2303 determines that at least some of the plurality of patients 2302 have experienced side effects on the basis of determination on whether the side effects have occurred for each of the plurality of patients 2302 or not, the analysis server 2303 may transmit the side effect occurrence information to the pharmaceutical company server.

According to the exemplary embodiment, clinical trial data may be generated on the basis of the obtained personalized estimates for each of the plurality of patients. For example, the analysis server 2303 may perform generating 2324 the clinical trial data on the basis of the obtained personalized estimates for each of the plurality of patients.

The clinical trial data may include time series data on mean values for all the plurality of patients 2302 with respect to exophthalmos degrees, CAS numerical values, whether the patient has diplopia, and/or whether side effects or not. In addition, the clinical trial data may include time-series data for each of plurality of patients 2302 with regard to the exophthalmos degrees, CAS numerical values, whether the patient has diplopia, and/or whether side effects or not. The time-series data may mean data arranged in time series. The specific details related to the time-series data have been described in 4. Treatment process monitoring, so duplicate description is omitted.

In addition, the clinical trial data may include information on drug efficacy rate by time point. The information on drug efficacy rate by time point may mean the number of patients in whom drug efficacy is expressed compared to the total number of patients at each time point. Whether the drug efficacy is expressed or not may be determined on the basis of the information intended to be proven as the effectiveness of medicine through a clinical trial. Specifically, in a case where the effectiveness of medicine intended to be proven is expressed through the clinical trial for the patients, it may be determined that the drug efficacy is expressed.

In addition, the clinical trial data may include information on side effect occurrence rate by time point. The information on side effect occurrence rate by time point may mean the number of patients who experienced side effects compared to the total number of patients at each time point. The whether side effects or not may be determined on the basis of the information intended to be proven as the side effects of a medicine through a clinical trial. Specifically, in a case where a patient experiences side effects that are intended to be proven as the side effects of the medicine through the clinical trial, it may be determined that the side effects have occurred.

By monitoring each of the plurality of patients, a pharmaceutical company may obtain much more data in a clinical trial.

The pharmaceutical company may use the clinical trial data obtained for drug research and/or drug development.

The pharmaceutical company may use the obtained clinical trial data to determine a medication administration regimen such as an appropriate dosage and/or an administration cycle for a medicine.

11. Post-Treatment Monitoring

Even when a patient's thyroid ophthalmopathy symptoms are cured at the end time point of a treatment by administering medicines for the purpose of treating thyroid ophthalmopathy to the patient, there is a case where the thyroid ophthalmopathy relapses after the end of the medicine administration. Accordingly, it is required to monitor whether the patient's thyroid ophthalmopathy worsens again after the treatment is finished.

Figure 25:
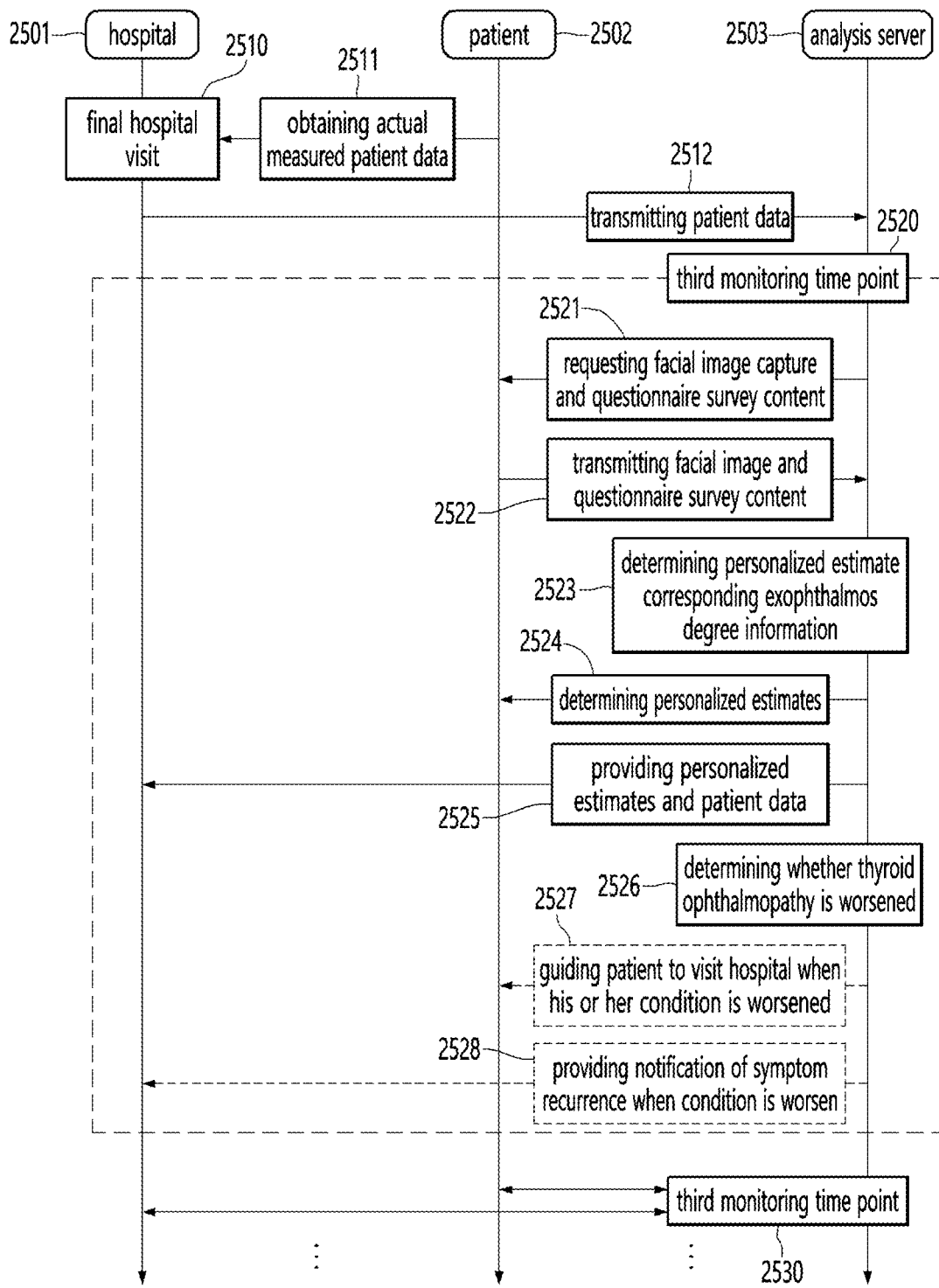
FIG. 25 is a view illustrating a post-treatment monitoring method according to the exemplary embodiment.

FIG. 25 is a view illustrating a post-treatment monitoring method according to the exemplary embodiment.

Referring to FIG. 25, a patient 2502 may be a patient who visited a hospital 2501 and administered all medicines for the purpose of treating thyroid ophthalmopathy and then completed his or her treatment.

The hospital 2501 may mean a hospital with medical staff assigned thereat. Meanwhile, the actions performed by the hospital may be understood as to be performed by the medical staff assigned at the hospital, the hospital server, the medical staff server, and/or the medical staff device, and a duplicate description will be omitted hereinafter.

The patient 2502 may be a patient with thyroid ophthalmopathy, or may be a patient who has finished the administration of the medicines for the purpose of treating the thyroid ophthalmopathy. Meanwhile, the actions performed by the patient 2502 below may be understood as being performed by the patient and/or the patient's user device, and a duplicate description is omitted below.

Referring to FIG. 25, the patient 2502 may make a final visit 2510 to the hospital 2501 after the medicine administration has ended, and the hospital 2501 may perform obtaining 2511 actual measured patient data from the patient 2502. Specifically, the medical staff assigned at the hospital 2501 may perform obtaining 2511 the actual measured patient data from the patient 2502. In this case, an end time point of treatment may be understood as a time point of the final visit to the hospital.

Meanwhile, the patient 2502 may be administered a medicine even at the time point of the final visit to the hospital 2501. Specifically, when the patient 2502 visits the hospital 2501, the medical staff assigned at the hospital 2501 may administer the medicine to the patient 2502. In this case, an end time point of this treatment may be understood as a time point at which the medicine administration has ended.

The hospital 2501 may perform transmitting 2512 obtained patient data to the analysis server 2503. The specific details regarding the patient data transmitted from the hospital 2501 to the analysis server 2503 have been described above in 4. Treatment process monitoring, so a duplicate description is omitted.

The analysis server 2503 may be a device that performs data transmission and reception with the hospital 2501 and the patient 2502, obtains patient data about the patient 2502, determines and/or estimates the patient's condition, and provides the determined and/or estimated patient data to the hospital 2501 and/or the patient 2502. This is not limited thereto, and the analysis server 2503 may be a device that stores patient data and/or information and like related to thyroid ophthalmopathy, which are obtained from the hospital 501 and/or the patient 2502, and provides the stored information to the hospital 2501 and/or the patient 2502. The specific details of the data transmission and reception performed, by the analysis server 2503, with the hospital 2501 and the patient 2502 have been described in 4. Treatment process monitoring, so a duplicate description is omitted.

Referring to FIG. 25, patient monitoring may be performed at every third monitoring time point 2520 and 2530.

According to the exemplary embodiment, the third monitoring time points 2520 and 2530 may be time points after a treatment period has ended as the medicine administration to the patient 2502 has ended.

According to the exemplary embodiment the third monitoring time points 2520 and 2530 may be determined on the basis of a set post-treatment monitoring cycle.

In this case, the post-treatment monitoring cycle may be set on the basis of the characteristics of a medicine and/or a patient's condition.

For example, the treatment monitoring cycle may be set such that monitoring is performed at specific intervals.

For a specific example, a post-treatment monitoring cycle may be set such that monitoring is performed at five-day intervals, but it is not limited thereto, and a specific period may be freely determined. Meanwhile, in this case, the post-treatment monitoring cycle may be longer than the treatment monitoring cycle described in 4. Treatment process monitoring.

For another example, since a time point of symptom recurrence may differ depending on each medicine, a post-treatment monitoring cycle may be set by considering the time point of symptom recurrence after the end of medicine administration. Alternatively, the post-treatment monitoring cycle may be set by considering the time point of symptom recurrence after the end of treatment.

Specifically, the post-treatment monitoring cycle may be set, so as to perform more frequent monitoring at time points where the rate of symptom recurrence is high according to clinical trial results. Alternatively, the post-treatment monitoring cycle may be set, so as to perform more frequent monitoring in intervals where the rate of symptom recurrence increases steeply according to the clinical trial results. For example, in a case where a medicine is effective after the end of treatment, but the effectiveness of medicine disappears after one year from the end of treatment and the rate of symptom recurrence is high, the post-treatment monitoring cycle may be set, so as to monitor more frequently from one year from the end of treatment, but it is not limited thereto.

Meanwhile, a treatment monitoring cycle may also be distinguished into a monitoring cycle set by a hospital and a monitoring cycle desired by a patient.

Specifically, the monitoring cycle set by the hospital may be set according to the characteristics of the medicine, and/or the patient's condition, as described above. The monitoring cycle desired by the patient is not limited to the monitoring cycle that is set by the hospital and may be freely set according to the patient's needs.

For example, the monitoring cycle that is set by the hospital may be set to once every three weeks after the end of treatment, and the monitoring cycle desired by the patient may be set to once a week, but it is not limited thereto.

Alternatively, the monitoring cycle set by the hospital may be set according to the characteristics of the medicine and/or the patient's condition as described above, but the monitoring cycle desired by the patient may not be set separately, and monitoring may be performed arbitrarily at any time point desired by the patient.

For example, in a case where the monitoring cycle that is set by the hospital is set to once every three weeks after the end of treatment, monitoring is performed according to the monitoring cycle set by the hospital, but additional monitoring may be performed at any time point desired by the patient, but it is not limited thereto.

Meanwhile, according to the exemplary embodiment, a third monitoring time point 2520 may also be determined at any time point at which the patient 2502 desires monitoring, without setting a separate post-treatment monitoring cycle.

In this case, the patient 2502 may transmit a monitoring request to the analysis server 2503 at any time point, and the analysis server 2503 may determine a time point of receiving the monitoring request from the patient 2502 as the third monitoring time point 2520, but it is not limited thereto.

Referring to FIG. 25, at the third monitoring time point 2520, the patient 2502 may be requested to capture a facial image and fill out questionnaire survey content.

In this case, a target that is requested to capture the facial image and fill out the questionnaire survey content may be a user device of the patient 2502. Hereinafter, the process where the patient is requested to capture the facial image and fill out the questionnaire survey content may be understood to be performed on the user device.

The patient 2502 may perform capturing the facial image and filling out the questionnaire survey content and transmit them in response to a request for capturing the facial image and filling out the questionnaire survey content. For example, the patient 2502 may capture the facial image and fill out the questionnaire survey content in response to the request 2521 for capturing the facial image and filling out the questionnaire survey content, which are requested from the analysis server 2503, and perform transmitting 2522 the facial image and questionnaire survey content to the analysis server 2503. Since the details, which include: the content related to the request for capturing the facial image and filling out the questionnaire survey content; the content related to capturing the facial image and filling out the questionnaire survey content; and the content related to transmitting the facial image and questionnaire survey content, have been described in 4. Treatment process monitoring, a duplicate description is omitted.

The patient's personalized estimate corresponding to exophthalmos degree information may be obtained on the basis of the facial image obtained from the patient 2502. For example, the analysis server 2503 may perform determining 2523 the patient's personalized estimate corresponding to the exophthalmos degree information by using the facial image obtained from the patient 2502. The specific method for determining the patient's personalized estimate corresponding to the exophthalmos degree information has been described in 4. Treatment process monitoring, 5. Facial image-based exophthalmos degree determination method, and 6. Facial image-based exophthalmos degree trend determination method, so a duplicate description is omitted.

The patient's personalized estimate corresponding to CAS information may be obtained on the basis of the facial image and questionnaire survey content obtained from the patient 2502. For example, the analysis server 2503 may determine the patient's personalized estimate corresponding to the CAS information by using the facial image and questionnaire survey content obtained from the patient 2502. The specific method for determining the patient's personalized estimate corresponding to the CAS information has been described in 4. Treatment process monitoring, so a duplicate description is omitted.

The obtained patient's personalized estimate may be displayed to the patient 2502 or provided to the hospital 2501.

Specifically, referring to FIG. 25, the analysis server 2503 may perform displaying 2524 the personalized estimate corresponding to the determined exophthalmos degree information to the patient 2502, and perform providing 2525 the personalized estimate corresponding to the determined exophthalmos degree information and the obtained patient data to the hospital 2501.

More specifically, the patient's personalized estimate may be provided to and displayed on the user device of the patient 2502, and the patient's personalized estimates and/or patient data may be provided to and displayed on the medical staff device and/or hospital server of the hospital 2501.

Meanwhile, in FIG. 25, it is illustrated that the patient's personalized estimates are displayed to the patient 2502 at the third monitoring time point 2520, but the time point at which the patient's personalized estimates are displayed to the patient 2502 is not limited to the third monitoring time point 2520. For example, the patient 2502 may check the patient's personalized estimates without having to capture a facial image or fill out questionnaire survey content. Specifically, the user device of the patient 2502 may display the patient's personalized estimates obtained from the analysis server 2503 at any time point desired by the patient 2502.

Meanwhile, in FIG. 25, it is illustrated that the hospital 2501 receives the patient's personalized estimates and patient data at the third monitoring time point 2520, but the time point at which the hospital 2501 receives the patient's personalized estimates and/or patient data is not limited to the third monitoring time point 2520. For example, the hospital 2501 may be provided with the patient's personalized estimates and/or patient data without the patient 2502 having to capture a facial image and fill out questionnaire survey. Specifically, the medical staff device and/or hospital server of the hospital 2501 may receive provision of the patient's personalized estimates and/or patient data from the analysis server 2503 at any time point desired by the medical staff.

The specific method for displaying and providing the patient's personalized estimates and patient data has been described above in 4. Treatment process monitoring, so a duplicate description is omitted.

Meanwhile, the patient's personalized estimate corresponding to the obtained exophthalmos degree information may be displayed together with values corresponding to the exophthalmos degree information given at an end time point of the thyroid ophthalmopathy treatment.

The value corresponding to the exophthalmos degree information at the end time point of the thyroid ophthalmopathy treatment may mean an exophthalmos numerical value corresponding to a time point at which the exophthalmos degree is alleviated as a result of the thyroid ophthalmopathy treatment.

For example, the values corresponding to the exophthalmos degree information at the end time point of the thyroid ophthalmopathy treatment may mean values including: values corresponding to the exophthalmos degree information at the end time point of administering a medicine; a value corresponding to the exophthalmos degree information at the last time point of administering the medicine; a value corresponding to the exophthalmos degree information at the time point of the final visit to the hospital; and/or a value corresponding to the exophthalmos degree information included in the patient data obtained from the hospital at the time point of the final visit to the hospital, but it is not limited thereto.

The patient's personalized estimate corresponding to the obtained exophthalmos degree information may be displayed, so as to compare and check the patient's personalized estimate with the value corresponding to the exophthalmos degree information at the end time point of thyroid ophthalmopathy treatment. Specifically, the patient's personalized estimate corresponding to the obtained exophthalmos degree information may be displayed so as to be compared with the value corresponding to the exophthalmos degree information at the end time point of thyroid ophthalmopathy treatment, rather than being displayed so as to be compared with an exophthalmos degree before the occurrence of the patient's exophthalmos. That is, even though there is a difference between the exophthalmos numerical value before the patient develops exophthalmos and the exophthalmos numerical value at the end time point of thyroid ophthalmopathy treatment, the patient's personalized estimate may be displayed so as to be compared with the exophthalmos numerical value at the end time point of treatment.

FIG. 26 is a view illustrating a UI for displaying the patient's personalized estimates according to the exemplary embodiment.

Referring to FIG. 26, displaying 2610 obtained patient's personalized estimates 2630 may be performed so that the obtained patient's personalized estimates may be verified by comparisons with values including: a value corresponding to the exophthalmos degree information at the end time point of thyroid ophthalmopathy treatment, a value corresponding to the CAS information, and/or a value 2620 corresponding to the diplopia information. In this case, the obtained patient's personalized estimates 2630 may be an obtained personalized estimates at a current time point, or may be the patient's personalized estimates obtained most recently.

Referring to FIG. 26, difference values 2640 may also be displayed to facilitate comparing the patient's obtained personalized estimates 2630 with the values including the value corresponding to the exophthalmos degree information at the end time point of the thyroid ophthalmopathy treatment, the value corresponding to the CAS information, and/or the value 2620 corresponding to the diplopia information.

The patient's obtained personalized estimates are displayed together with the values including the value corresponding to the patient's exophthalmos degree information at the end time point of the thyroid ophthalmopathy treatment, the value corresponding to the CAS information, and/or the value corresponding to the diplopia information, so that the patient and/or the hospital may easily determine whether the thyroid ophthalmopathy has worsened or not.

The patient's personalized estimates corresponding to the exophthalmos degree information obtained after the end time point of the thyroid ophthalmopathy treatment may be displayed as time-series data. The time-series data may mean data arranged in time series. The specific details related to the time-series data have been described in 4. Treatment process monitoring, so a duplicate description is omitted.

The patient's personalized estimates corresponding to the exophthalmos degree information obtained after the end time point of the thyroid ophthalmopathy treatment may be displayed as the time-series data together with the value corresponding to the exophthalmos degree information at the end time point of the thyroid ophthalmopathy treatment. The time-series data may mean data arranged in time series. The specific details related to the time-series data have been described in 4. Treatment process monitoring, so a duplicate description is omitted.

The patient's personalized estimates corresponding to the obtained exophthalmos degree information are displayed together with the value corresponding the exophthalmos degree information at the end time point of the thyroid ophthalmopathy treatment, so that the patient and/or the hospital may determine whether the thyroid ophthalmopathy has worsened or not.

The patient's personalized estimates corresponding to the exophthalmos degree information obtained after the end time point of the thyroid ophthalmopathy treatment are displayed as the time-series data, so that the patient and/or the hospital may determine whether the thyroid ophthalmopathy has worsened or not.

The patient's personalized estimates corresponding to the obtained CAS information may be displayed together with the values corresponding the CAS information at the end time point of the thyroid ophthalmopathy treatment.

The values corresponding to the CAS information at the end time point of the thyroid ophthalmopathy treatment may mean the CAS information corresponding to a time point at which CAS numerical values are alleviated as a result of the thyroid ophthalmopathy treatment.

For example, the values corresponding to the CAS information at the end time point of the thyroid ophthalmopathy treatment may mean values including: a value corresponding to the CAS information at the end time point of medicine administration; a value corresponding to the CAS information at the last time point of medicine administration; a value corresponding to the CAS information at the time point of the final visit to the hospital; and/or a value corresponding to the CAS information included in the patient data obtained from the hospital at the time point of the final visit to the hospital, but it is not limited thereto.

The patient's personalized estimates corresponding to the obtained CAS information may be displayed so as to be checked by the comparison with the value corresponding to the CAS information at the end time point of thyroid ophthalmopathy treatment.

The patient's personalized estimates corresponding to the CAS information obtained after the end time point of the thyroid ophthalmopathy treatment may be displayed as time-series data. The time-series data may mean data arranged in time series. The specific details related to the time-series data have been described in 4. Treatment process monitoring, so a duplicate description is omitted.

The patient's personalized estimates corresponding to the CAS information obtained after the end time point of the thyroid ophthalmopathy treatment may be displayed as the time-series data together with the value corresponding to the CAS information at the end time point of the thyroid ophthalmopathy treatment. The time-series data may mean data arranged in time series. The specific details related to the time-series data have been described in 4. Treatment process monitoring, so a duplicate description is omitted.

The patient's personalized estimates corresponding to the obtained CAS information are displayed together with the value corresponding the CAS information at the end time point of the thyroid ophthalmopathy treatment, so that the patient and/or the hospital may determine whether the thyroid ophthalmopathy has worsened or not.

The patient's personalized estimates corresponding to the CAS information obtained after the end time point of the thyroid ophthalmopathy treatment are displayed as the time-series data, so that the patient and/or the hospital may determine whether the thyroid ophthalmopathy has worsened or not.

Meanwhile, the content described above in 4. Treatment process monitoring may be applied to the specific method for displaying the patient's obtained personalized estimates, so a duplicate description is omitted.

Whether thyroid ophthalmopathy has worsened or not may be determined on the basis of a comparison of the patient's personalized estimate corresponding to the obtained exophthalmos degree information and the value corresponding to the exophthalmos degree information at the end time point of the thyroid ophthalmopathy treatment. Specifically, whether the thyroid ophthalmopathy has worsened or not may be determined not by way of comparing the patient's personalized estimate corresponding to the obtained exophthalmos degree information with an exophthalmos degree before the patient develops exophthalmos, but by way of comparing the patient's personalized estimate corresponding to the obtained exophthalmos degree information with the value corresponding to the exophthalmos degree information at the end time point of the thyroid ophthalmopathy treatment. That is, even when there is a difference between an exophthalmos numerical value before the patient develops exophthalmos and an exophthalmos numerical value at the end time point of the thyroid ophthalmopathy treatment, whether the thyroid ophthalmopathy has worsened or not may be determined on the basis of the exophthalmos degree at the end time point of the thyroid ophthalmopathy treatment.

Referring back to FIG. 25, the analysis server 2503 may perform determining 2526 whether the thyroid ophthalmopathy has worsened or not on the basis of the comparison of the patient's personalized estimate corresponding to the determined exophthalmos degree information and the value corresponding to the exophthalmos degree information at the end time point of the thyroid ophthalmopathy treatment.

Specifically, the thyroid ophthalmopathy may be determined to have worsened in a case where the patient's personalized estimate corresponding to the obtained exophthalmos degree information increases by the threshold or more compared to the value corresponding to the exophthalmos degree information at the end time point of the thyroid ophthalmopathy treatment.

For example, the thyroid ophthalmopathy may be determined to have worsened in a case where the patient's personalized estimate corresponding to the obtained exophthalmos degree information increases by the threshold greater than or equal to 1 mm, 2 mm, 3 mm, 4 mm, 5 mm, 6 mm, 7 mm, 8 mm, 9 mm, 10 mm, or 11 mm compared to the value corresponding to the exophthalmos degree information at the end time point of the thyroid ophthalmopathy treatment. Preferably, the thyroid ophthalmopathy may be determined to have worsened in a case where the patient's personalized estimate corresponding to the obtained exophthalmos degree information increases by 2 mm or more compared to the value corresponding to the exophthalmos degree information at the end time point of the thyroid ophthalmopathy treatment, and the threshold for the increase in the exophthalmos numerical value is not limited to the examples described above.

Alternatively, the thyroid ophthalmopathy may be determined to have worsened in a case where a trend in the exophthalmos degrees included in the patient's personalized estimates corresponding to the obtained exophthalmos degree information shows an increase by a threshold or more compared to the value at the end time point of the thyroid ophthalmopathy treatment. In this case, two time points used to determine the trend in the exophthalmos degrees may be the current time point and the end time point of the thyroid ophthalmopathy treatment.

Whether thyroid ophthalmopathy has worsened or not may be determined on the basis of a comparison of the patient's personalized estimate corresponding to the obtained CAS information and the value corresponding to the CAS information at the end time point of the thyroid ophthalmopathy treatment. For example, the analysis server 2503 may determine whether the thyroid ophthalmopathy has worsened or not on the basis of the comparison of the patient's personalized estimate corresponding to the determined CAS information and the value corresponding to the CAS information at the end time point of the thyroid ophthalmopathy treatment.

Specifically, the thyroid ophthalmopathy may be determined to have worsened in a case where the patient's personalized estimate corresponding to the obtained CAS information increases by the threshold or more compared to the value corresponding to the CAS information at the end time point of the thyroid ophthalmopathy treatment.

For example, the thyroid ophthalmopathy may be determined to have worsened in a case where the patient's personalized estimate corresponding to the obtained CAS information increases by two points or more compared to the value corresponding to the CAS information at the end time point of the thyroid ophthalmopathy treatment. In a case of a CAS numerical value, depending on the patient's condition, the patient may temporarily experience redness of eyelid, redness of conjunctiva, swelling of eyelid, swelling of conjunctiva, swelling of lacrimal caruncle, spontaneous retrobulbar pain, or pain on attempted upward or downward gaze. Therefore, it may be preferable to determine that the thyroid ophthalmopathy has worsened in a case where the CAS numerical value increases by two points or more, rather than by one point or more, and the threshold for the increase of the CAS numerical value is not limited to the examples described above.

Alternatively, the thyroid ophthalmopathy may be determined to have worsened in a case where the patient's personalized estimate corresponding to the obtained CAS information is greater than or equal to a threshold.

For example, the thyroid ophthalmopathy may be determined to have worsened in a case where the patient's personalized estimate corresponding to the obtained CAS information is three points or more, and a threshold for a CAS numerical value is not limited to the examples described above.

Whether thyroid ophthalmopathy has worsened or not may be determined on the basis of a single point in time. Specifically, whether thyroid ophthalmopathy has worsened or not may be finally determined on the basis of determining whether the thyroid ophthalmopathy has worsened or not at one time point.

For example, in a case where thyroid ophthalmopathy is determined to have worsened on the basis of the personalized estimate obtained at a third monitoring time point given for the n-th time, the thyroid ophthalmopathy may be finally determined to have worsened at the third monitoring time point given for the n-th time.

Alternatively, whether thyroid ophthalmopathy has worsened or not may also be finally determined on the basis of a plurality of time points. Specifically, whether the thyroid ophthalmopathy has worsened or not may be finally determined on the basis of determining whether the thyroid ophthalmopathy has worsened or not at the plurality of time points.

More specifically, in a case where thyroid ophthalmopathy is determined to have worsened consecutively over a plurality of time points, the thyroid ophthalmopathy may be finally determined to have worsened.

For example, in a case where thyroid ophthalmopathy is determined to have worsened on the basis of the respective personalized estimates obtained at time points including: a third monitoring time point given for the n-th time, a third monitoring time point given for the (n+1)-th time, and a third monitoring time point given for the (n+2)-th time, the thyroid ophthalmopathy may be finally determined to have worsened at one of the monitoring time points from the third monitoring time point given for the n-th time to the third monitoring time point given for the (n+2)-th time. This is not limited thereto, and the number of determination time points may be set variously depending on the characteristics of a medicine, a patient's condition, and/or a monitoring design.

Meanwhile, more specifically, in a case where it is determined that thyroid ophthalmopathy has worsened more than a critical number of times within a certain period of time, it may be finally determined that the thyroid ophthalmopathy has worsened.

For example, in a case where there are n-th to (n+2)-th third monitoring time points within a two-week period, it may be finally determined that thyroid ophthalmopathy has worsened when the thyroid ophthalmopathy is determined to have worsened more than twice. For a specific example, when there are given cases for determination using: a case where the thyroid ophthalmopathy is determined to have worsened on the basis of the personalized estimate obtained at the third monitoring time point given for the n-th time; a case where the thyroid ophthalmopathy is determined to have not worsened on the basis of the personalized estimate obtained at the third monitoring time point given for the (n+1)-th time; and a case where the thyroid ophthalmopathy is determined to have worsened on the basis of the personalized estimate obtained at the third monitoring time point given for the (n+2)-th time, the thyroid ophthalmopathy may be finally determined to have worsened at one of the monitoring time points from the n-th third monitoring time point to the (n+2)-th third monitoring time point. This is not limited thereto, and a predetermined period of time and the critical number of times may be set variously depending on the characteristics of the medicine, the patient's condition, and/or the monitoring design.

Depending on a determination result of whether the thyroid ophthalmopathy of the patient 2502 has worsened or not, the patient 2502 may be guided to visit the hospital.

For example, referring to FIG. 20, in a case of determining that thyroid ophthalmopathy has worsened on the basis of the obtained personalized estimates of the patient 2502, the analysis server 2503 may perform guiding 2527 the patient 2502 to visit the hospital. For a more specific example, the analysis server 2503 may display a message regarding suggestion of a hospital visit through a user device of the patient 2502, but it is not limited thereto.

Depending on the determination result of whether the thyroid ophthalmopathy of the patient 2502 has worsened or not, the hospital 2501 may receive a notification of a thyroid ophthalmopathy recurrence of the patient 2502.

For example, referring to FIG. 20, in a case of determining that the thyroid ophthalmopathy has worsened on the basis of the obtained personalized estimates of the patient 2502, the analysis server 2503 may transmit, to the hospital 2501, a notification 2528 of the thyroid ophthalmopathy recurrence of the patient 2502. For a more specific example, the analysis server 2503 may display a message regarding the thyroid ophthalmopathy recurrence of the patient 2502 through medical staff device of the hospital 2501, but it is not limited thereto.

Depending on the determination result of whether the thyroid ophthalmopathy of the patient 2502 has worsened or not, a pharmaceutical company may be provided with information related to a symptom recurrence of a medicine.

The information related to the symptom recurrence may include information related to the patient's condition, patient data, a symptom recurrence time point, and/or the degree of symptom recurrence, but it is not limited thereto.

Side effects may occur even after the medicine administration has ended. Since the side effects may require a rapid action, whether the patient experiences any side effects or not may also be monitored during post-treatment monitoring. Specifically, information regarding the side effects may also be obtained from the patient during the post-treatment monitoring.

The side effect-related information to be obtained from the patient may be determined on the basis of the clinical trial results of a medicine. For example, information related to side effects may include: whether muscle cramps are present or not, whether nausea is present or not, whether hair loss is present or not, whether diarrhea is present or not, whether fatigue is present or not, and/or whether hyperglycemia is present or not, and the information related to the side effects may vary from medicine to medicine.

Meanwhile, the information related to the side effects may be obtained on the basis of questionnaire survey content requested from the patient. Specifically, the questionnaire survey content that the patient is requested to fill out may include questionnaire survey content about signs and/or symptoms associated with the side effects. Since each medicine may have different side effects, the questionnaire survey content requested to the patient may be determined on the basis of which medicine the patient is administered.

Meanwhile, the patient may be provided first with the information related to the side effects before being requested to fill out the questionnaire survey content related to the side effects.

The patient and/or the hospital may be provided with a message and/or additional data on the basis of the information regarding the side effects obtained from the patient, The message and/or additional data provided to the patient and/or hospital may be determined on the basis of details of the action taken in response to side effects described in a medication manual for the medicine.

For example, in a case where the patient is determined to have experienced side effects on the basis of the information related to the side effects obtained from the patient, the patient may be provided with a message for suggesting a phone call to an administrative agency and/or regulatory agency responsible for managing the safety of medical supplies. In this case, the message may include phone numbers of the administrative agency and/or regulatory agency that are responsible for managing the safety of medical supplies.

Alternatively, the patient may be provided with a message for suggesting access to Internet sites of the administrative agency and/or regulatory agency that are managing the safety of medical supplies. In this case, the message may include the Internet addresses of websites of the administrative agency and/or regulatory agency that are responsible for managing the safety of medical supplies.

Alternatively, the patient may be provided with a message for suggesting a phone call to the hospital. In this case, the hospital may be a hospital where the patient has visited, and the message may include the hospital's phone number.

Alternatively, the patient may be provided with a message for suggesting access to the hospital's Internet site. In this case, the hospital may be a hospital where the patient has visited, and the message may include the Internet address of a website of the hospital.

Meanwhile, the hospital may be provided with a message for warning the patient that side effects have occurred, and may be provided with information, which is related to the side effects, as additional data.

Patient monitoring is performed even after thyroid ophthalmopathy treatment has ended, so the patient may be guided to visit a hospital early in a case where the thyroid ophthalmopathy relapses. Accordingly, this may prevent the patient from not recognizing the recurrence of thyroid ophthalmopathy but rather visiting the hospital after the thyroid ophthalmopathy has significantly worsened in a case where the patient's thyroid ophthalmopathy relapses.

In addition, patient monitoring is performed even after thyroid ophthalmopathy treatment has ended, so the hospital may diagnose the patient on the basis of the obtained patient data and the patient's personalized estimates. Accordingly, the hospital may provide a more accurate diagnose to the patient.

In addition, patient monitoring is performed even after the thyroid ophthalmopathy treatment has ended, so the pharmaceutical company may obtain data related to symptoms that appear in the patient after the medicine administration has ended. Accordingly, in researching and/or developing medicines, the pharmaceutical company may use the data related to the symptoms, which appear in the patient after the medicine administration has ended.

Figure 27:
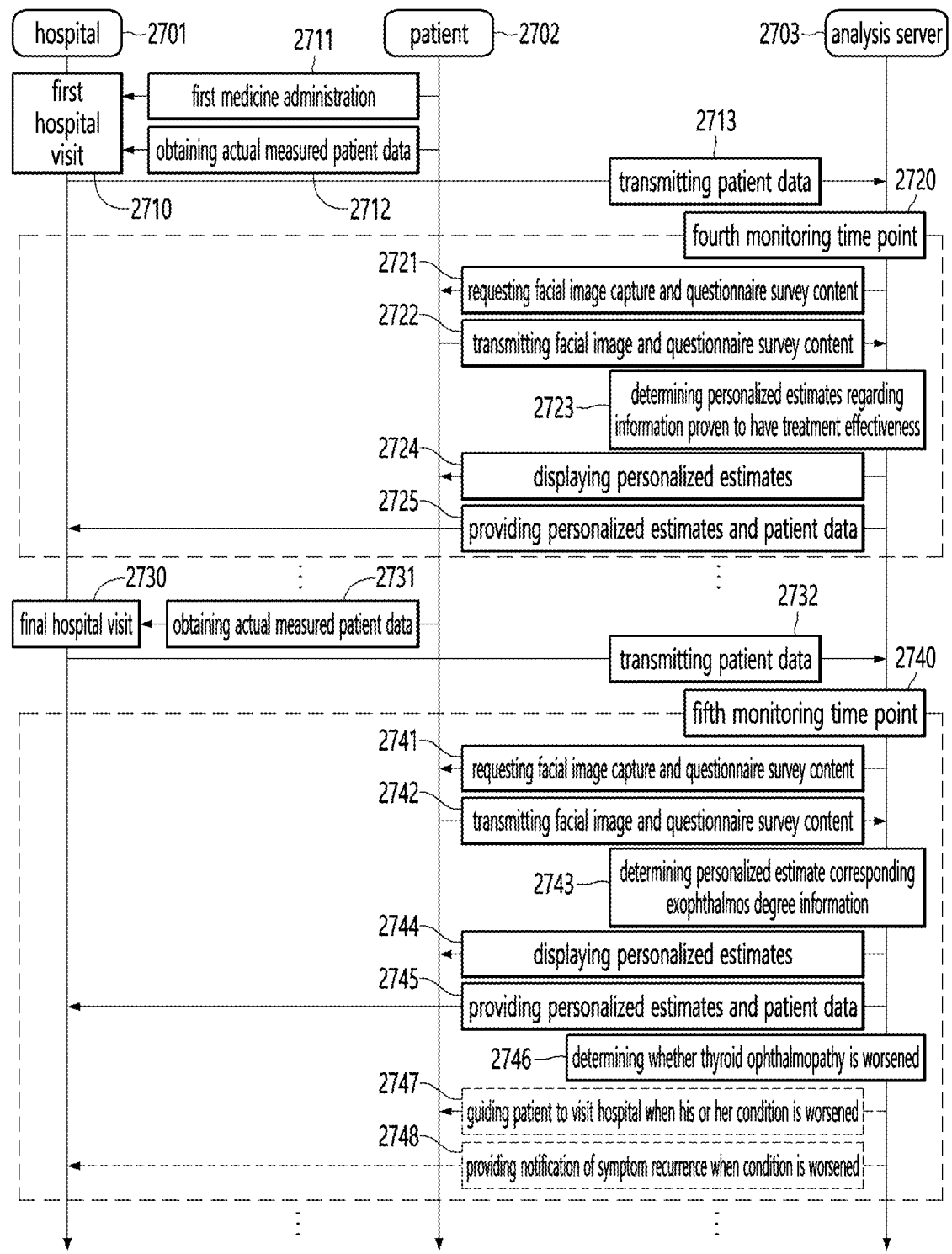
FIG. 27 is a view illustrating a method for monitoring the overall treatment according to the exemplary embodiment.

FIG. 27 is a view illustrating a method for monitoring the overall treatment according to the exemplary embodiment.

Referring to FIG. 27, a patient 2702 may visit a hospital 2701 and be administered a medicine. Specifically, when the patient 2702 visits the hospital 2701, medical staff assigned at the hospital 2701 may administer the medicine to the patient 2702. Hereinafter, it may be understood that a process of administering the medicine to the patient when visiting the hospital is carried out by the medical staff assigned at the hospital.

The medicine may be a medicine for the purpose of treating thyroid ophthalmopathy, and may be a medicine of which the administration is required a plurality of times during a treatment period.

The hospital 2701 may mean a hospital assigned with the medical staff. Meanwhile, the actions performed by the hospital 2701 may be understood as actions performed by the medical staff assigned at the hospital, a hospital server, medical staff server, and/or medical staff device, and a duplicate description is omitted below.

The patient 2702 may be a patient with thyroid ophthalmopathy, and may be a patient prescribed and administered a medicine for the purpose of treating thyroid ophthalmopathy. Meanwhile, the actions performed by the patient 2702 below may be understood as being performed by the patient and/or the patient's user device, and a duplicate description is omitted below.

Referring to FIG. 27, the patient 2702 may receive administration 2711 of a medicine during a first visit 2710 to the hospital 2701, and the hospital 2701 may perform obtaining 2712 actual measured patient data from the patient 2702. Specifically, when the patient 2702 makes the first visit 2710 to the hospital 2701, the medical staff assigned at the hospital 2701 may administer the first medicine to the patient 2702, and the medical staff assigned at the hospital 2701 may perform obtaining 2712 of the actual measured patient data from the patient 2702. Below, the process of obtaining, by the hospital, the patient data when the patient visits the hospital may be understood as being performed by the medical staff assigned at the hospital.

In addition, the hospital 2701 may perform transmitting 2713 the obtained patient data to an analysis server 2703. Specifically, the hospital server, the medical staff server, and/or the medical staff device, which are disposed in the hospital 2701 may perform transmitting 2713 the patient data to the analysis server 2703. Hereinafter, the process of transmitting, by the hospital, data to the analysis server may be understood as being performed by the hospital server, the medical staff server, and/or the medical staff device, which are disposed in the hospital.

The specific details related to medicine administration, patient data acquisition, and patient data transmission have been described in 4. Treatment process monitoring, so a duplicate description is omitted.

The analysis server 2703 may be a device that performs data transmission and reception with the hospital 2701 and the patient 2702, obtains patient data about the patient 2702, determines and/or estimates the patient's condition, and provides the determined and/or estimated patient data to the hospital 2701 and/or the patient 2702. Specifically, the analysis server 2703 performs the data transmission and reception with the hospital server, medical staff server, and/or medical staff device, which are disposed in the hospital 2701, and may perform the data transmission and reception with the user device of the patient 2702. In addition, the analysis server 2703 transmits the determined and/or estimated patient data to the hospital server, the medical staff server and/or the medical staff device, which are disposed in the hospital 2701, and may transmit the determined and/or estimated patient data to the user device of the patient 2702.

In addition, the analysis server 2703 may be a device that stores the patient data and/or information related to thyroid ophthalmopathy, which are obtained from the hospital 2701 and/or the patient 2702, and provides the stored information to the hospital 2701 and/or the patient 2702. Specifically, the analysis server 2703 transmits the stored information to the hospital server, the medical staff server, and/or the medical staff device, which are disposed in the hospital 2701, and may transmit the stored information to the user device of the patient 2702.

Referring to FIG. 27, patient monitoring may be performed at each fourth monitoring time point 2720.

At a fourth monitoring time point 2720, the analysis server 2703 may perform requesting 2721 the patient 2702 to capture a facial image and fill out questionnaire survey content, the patient 2702 may perform transmitting 2722 the facial image and questionnaire survey content to the analysis server 2703, the analysis server 2703 may perform determining 2723 a personalized estimate for information proven as a treatment effect by using the obtained facial image and the questionnaire survey content, the analysis server 2703 may perform displaying 2724 the patient's determined personalized estimate to the patient 2702, and the analysis server 2703 may perform providing 2732 the patient's personalized estimate and patient data to the hospital 2701.

More specifically, for actions performed at a fourth monitoring time point 2720, the content of the actions performed at the first monitoring time point described in 4. Treatment process monitoring may be applied thereto, so a duplicate description is omitted.

Referring to FIG. 27, the patient 2702 may visit the hospital 2701 and be administered the medicine, and then make a final visit 2730 to the hospital 2701, and the hospital 2701 may obtain actual measured patient data 2731 from the patient 2702. In addition, the hospital 2701 may perform transmitting 2732 the obtained patient data to the analysis server 2703. The specific details regarding the patient data transmitted from the hospital 2701 to the analysis server 2703 have been described above in 4. Treatment process monitoring, so a duplicate description is omitted.

Referring to FIG. 27, patient monitoring may be performed at each fifth monitoring time point 2740.

At a fifth monitoring time point, the analysis server 2703 may perform requesting 2741 the patient 2702 to capture a facial image capture and fill out questionnaire survey content, the patient 2702 may perform transmitting 2742 the facial image and questionnaire survey content to the analysis server 2703, and the analysis server 2703 may perform determining 2743 a personalized estimate corresponding to the exophthalmos degree information by using the obtained facial image and questionnaire survey content. The analysis server 2703 may perform displaying 2744 the patient's determined personalized estimate to the patient 2702 and perform providing 2745 the patient's personalized estimate and patient data to the hospital 2701. The analysis server 2703 may perform determining 2746 whether the thyroid ophthalmopathy of the patient 2702 has worsened or not on the basis of the patient's determined personalized estimate. According to the determination result of whether the thyroid ophthalmopathy has worsened or not, the analysis server 2703 may perform guiding 2747 the patient 2702 to visit the hospital due to worsening condition thereof and may transmit a notification 2748 of the patient's thyroid ophthalmopathy recurrence to the hospital 2701.

More specifically, with regard to actions performed at the fifth monitoring time point 2740, the content of the actions performed at the third monitoring time point described in 11. Post-treatment monitoring may be applied thereto, so a duplicate description is omitted.

12. Monitoring System

Figure 28:
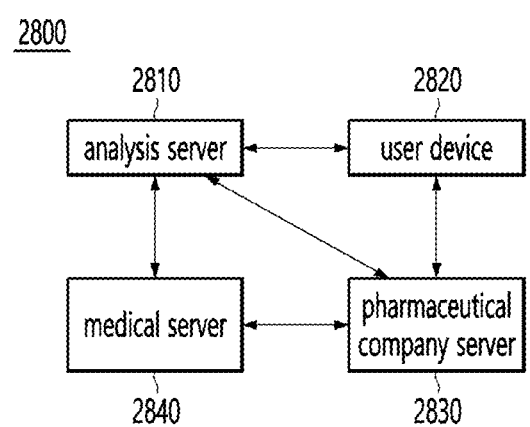
FIG. 28 is a view illustrating a system for monitoring the effectiveness of medicine according to the exemplary embodiment.

FIG. 28 is a view illustrating a system for monitoring the effectiveness of medicine according to an exemplary embodiment.

A medicine effectiveness monitoring system 2800 may monitor the condition of a patient who is administered a medicine, monitor the condition of the patient whose treatment has ended, or monitor the subject's conditions in clinical trials.

The patient may be a patient being treated for or having been treated for thyroid ophthalmopathy, but it is not limited thereto.

The medicine may be a medicine for the purpose of treating thyroid ophthalmopathy.

The patient's condition may mean changes in the patient's condition depending on the effectiveness of medicine and/or changes in the patient's condition after the medicine administration has ended.

The effectiveness of medicine may include intended effects of a medicine and/or side effects of the medicine.

The medicine effectiveness monitoring system 2800 may monitor the patient's condition on the basis of the patient's facial image and/or the patient's questionnaire survey content. The specific details regarding the facial image and/or questionnaire survey content have been described above, so a duplicate description is omitted.

Referring to FIG. 28, the medicine effectiveness monitoring system 2800 may include an analysis server 2810, a user device 2820, a medical server 2830, and a pharmaceutical company server 2240.

(1) Analysis Server

The analysis server 2810 is a device that estimates and/or determines a patient's condition by using data related to the patient and generates estimated data about the patient. Specifically, the analysis server 2810 may perform the actions performed by the analysis server described above in 4. Treatment process monitoring, 10. Clinical trial monitoring, and 11. Post-treatment monitoring.

The analysis server 2810 may include a communication device, memory, and a processor.

The communication device of the analysis server 2810 may transmit and/or receive data and/or information to and/or from the outside through wired and/or wireless communication. The communication device may perform bidirectional or unidirectional communication.

The communication device of the analysis server 2810 may include a wireless communication module and/or a wired communication module. The wireless communication module may include a Wi-Fi communication module, a cellular communication module, etc.

The memory of the analysis server 2810 may store various processing programs, parameters for processing the programs, data as results obtained through such processing and the like. For example, the memory of the analysis server 2810 may store instructions, algorithms, and/or executable codes for the actions of the processor of the analysis server 2810 described below.

The memory of the analysis server 2810 may store a patient's facial image and questionnaire survey content obtained from the user device 2820. The specific details related to the facial image and questionnaire survey content have been described in 4. Treatment process monitoring, 8. Capturing and transmitting facial image, 10. Clinical trial monitoring, and 11. Post-treatment monitoring, so a duplicate description is omitted.

The memory of the analysis server 2810 may store patient data obtained from the user device 2820 and the medical server 2830. The specific details regarding the types of patient data have been described in 4. Treatment process monitoring, 10. Clinical trial monitoring, and 11. Post-treatment monitoring, so a duplicate description is omitted.

The memory of the analysis server 2810 may store a patient's personalized estimates. The patient's personalized estimates may include exophthalmos degree information, CAS information, and diplopia information, and the specific details related to the personalized estimates have been described in 4. Treatment process monitoring, 10. Clinical trial monitoring, and 11. Post-treatment monitoring, so a duplicate description is omitted.

The memory of the analysis server 2810 may store information on a treatment monitoring cycle, a post-treatment monitoring cycle, and/or a clinical trial monitoring cycle, which are for a patient. The memory of the analysis server 2810 may store information on monitoring time points. The specific details on the monitoring cycles and monitoring time points are described in 4. Treatment process monitoring, 10. Clinical trial monitoring, and 11. Post-treatment monitoring, so a duplicate description is omitted.

The memory may be implemented as a nonvolatile semiconductor memory, a hard disk drive (HDD), a solid state disk (SSD), a silicon disk drive (SDD), flash memory, a random access memory (RAM), a read only memory (ROM), an electrically erasable programmable read-only memory (EEPROM), other types of (tangible) nonvolatile recording media, or the like.

The processor of the analysis server 2810 may control the overall action of the analysis server 2810 and may perform actions according to instructions, algorithms, and/or executable codes, which are stored in the memory of the analysis server 2810.

The processor of the analysis server 2810 may receive patient data from the user device 2820 and/or the medical server 2830 through the communication device of the analysis server 2810. The processor of the analysis server 2810 may request capturing a facial image and filling out questionnaire survey content from the user device 2820 through the communication device of the analysis server 2810. The processor of the analysis server 2810 may receive the facial image and questionnaire survey content from the user device 2820 through the communication device of the analysis server 2810. Specific details on receiving the patient data, requesting the facial image and questionnaire survey content, and receiving the facial image and questionnaire survey content have been described in 4. Treatment process monitoring, 10. Clinical trial monitoring, and 11. Post-treatment monitoring, so a duplicate description is omitted.

The processor of the analysis server 2810 may determine the personalized estimates of the patient by using the facial images and/or the questionnaire survey content. The patient's personalized estimates may include the exophthalmos degree information, CAS information, and diplopia information, and the specific details for determining the patient's personalized estimates have been described in 2. Thyroid ophthalmopathy activity, 3. Thyroid ophthalmopathy severity, 4. Treatment process monitoring, 5. Facial image-based exophthalmos degree determination method, 6. Facial image-based exophthalmos degree trend determination method, 7. Facial image-based eyelid retraction determination method, 10. Clinical trial monitoring, and 11. Post-treatment monitoring, so a duplicate description is omitted.

The processor of the analysis server 2810 may transmit the patient's personalized estimates and/or patient data to the user device 2820, the medical server 2830, and/or the pharmaceutical company server 2240 through the communication device of the analysis server 2810.

The processor of the analysis server 2810 may determine whether the patient's thyroid ophthalmopathy is worsened or not on the basis of the patient's personalized estimates. The specific method for determining whether thyroid ophthalmopathy is worsened or not has been described in 11. Post-treatment monitoring, so a duplicate description is omitted.

The processor of the analysis server 2810 may transmit a message for suggesting a hospital visit to the user device 2820 according to the determination result of whether the patient's thyroid ophthalmopathy has worsened or not. The processor of the analysis server 2810 may transmit a notification of the patient's thyroid ophthalmopathy recurrence to the medical server 2830 according to the determination result of whether the patient's thyroid ophthalmopathy has worsened or not. The specific details of actions according to whether thyroid ophthalmopathy has worsened or not are described in 11. Post-treatment monitoring, so a duplicate description is omitted.

The processor of the analysis server 2810 may generate clinical trial data on the basis of the patient's personalized estimates. The processor of the analysis server 2810 may transmit the clinical trial data to the pharmaceutical company server 2240 through the communication device of the analysis server 2810. The specific details regarding the clinical trial data have been described in 10. Clinical trial monitoring, so a duplicate description are omitted.

The processor of the analysis server 2810 may obtain the patient's side effect occurrence information on the basis of the questionnaire survey content obtained from the patient. The processor of the analysis server 2810 may transmit the side effect occurrence information to the pharmaceutical company server 2240 through the communication device of the analysis server 2810. The specific details related to the side effect occurrence information have been described in 10. Clinical trial monitoring, so a duplicate description is omitted.

Meanwhile, the processor may be implemented with components such as a central processing unit (CPU), a graphics processing unit (GPU), a digital signal processor (DSP), a state machine, an application-specific integrated circuit (ASIC), a radio frequency integrated circuit (RFIC), and a combination thereof.

(2) User Device

A user device 2820 is a device that interacts directly and/or indirectly with a patient. Specifically, the user device 2820 may perform the actions performed by the patient described above in 4. Treatment process monitoring, 10. Clinical trial monitoring, and 11. Post-treatment monitoring.

The user device 2820 may include a camera module, a user interface, a communication device, memory, and a processor.

The camera module of the user device 2820 is a digital camera module and may include an image sensor and an image processing unit. The image sensor is a device for converting an optical image into electrical signals, and may be composed of a chip having a plurality of photo diodes integrated therein. For example, the image sensor may include a Charge Coupled Device (CCD), a Complementary Metal Oxide Semiconductor (CMOS), etc. The image processing unit may generate image information by performing image processing on the photographed results.

The user interface of the user device 2820 may output various information according to control commands of the processor of the user device 2820. The user interface of the user device 2820 may include a display for visually outputting information to a patient. The user interface of the user device 2820 may include a speaker for audibly outputting information to the patient.

The user interface of the user device 2820 may receive input of various kinds of information from the patient. The patient may enter various kinds of information through the user interface of the user device 2820. The user interface of the user device 2820 may include input devices such as a keyboard, a mouse, and/or a touch screen.

The communication device of the user device 2820 may transmit and/or receive data and/or information to and/or from the outside through wired and/or wireless communication. The communication device may perform bidirectional or unidirectional communication.

The communication device of the user device 2820 may include a wireless communication module and/or a wired communication module. The wireless communication module may include a Wi-Fi communication module, a cellular communication module, etc.

The memory of the user device 2820 may store various processing programs, parameters for processing programs, data as results obtained through such processing and the like. For example, the memory of the user device 2820 may store instructions, algorithms, and/or executable codes for the actions of the processor of the user device 2820 described below.

The memory of the user device 2820 may store a facial image captured through the camera module. The specific details related to the facial image have been described in 4. Treatment process monitoring, 8. Capturing and transmitting facial image, 10. Clinical trial monitoring, and 11. Post-treatment monitoring, so a duplicate description is omitted.

The memory of the user device 2820 may store questionnaire survey content to be displayed on a user interface. The memory of the user device 2820 may store a questionnaire survey result entered by the patient through the user interface. The specific details related to the questionnaire survey content have been described in 4. Treatment process monitoring, 10. Clinical trial monitoring, and 11. Post-treatment monitoring, so a duplicate description is omitted.

The memory of the user device 2820 may store the patient's personalized estimates obtained from the analysis server 2810. The patient's personalized estimates may include exophthalmos degree information, CAS information, and diplopia information, and the specific details related to the personalized estimates have been described in 4. Treatment process monitoring, 10. Clinical trial monitoring, and 11. Post-treatment monitoring, so a duplicate description is omitted.

The memory of the user device 2820 may store patient data obtained from the analysis server 2810 and/or the medical server 2830. The specific details regarding the types of patient data have been described in 4. Treatment process monitoring, 10. Clinical trial monitoring, and 11. Post-treatment monitoring, so a duplicate description is omitted.

The memory may be implemented with a nonvolatile semiconductor memory, HDD, SSD, SDD, flash memory, RAM, ROM, EEPROM, or other types of nonvolatile recording media.

The processor of the user device 2820 may control the overall action of the user device 2820 and may perform the actions according to instructions, algorithms, and/or executable codes stored in the memory of the user device 2820.

The processor of the user device 2820 may receive a request for capturing a facial image and filling out questionnaire survey content from the analysis server 2810 through the communication device of the user device 2820.

The processor of the user device 2820 may capture the patient's facial image by using the camera module of the user device 2820. The specific details on facial image capture have been described above in 8. Capturing and transmitting facial image, so a duplicate description IS omitted.

The processor of the user device 2820 may display the questionnaire survey content through the user interface of the user device 2820. The processor of the user device 2820 may receive input regarding the questionnaire survey content from the patient through the user interface of the user device 2820. The specific details related to the questionnaire survey content have been described in 4. Treatment process monitoring, 10. Clinical trial monitoring, and 11. Post-treatment monitoring, so a duplicate description is omitted.

The processor of the user device 2820 may generate questionnaire survey results on the basis of the patient's input regarding the questionnaire survey content.

The processor of the user device 2820 may transmit the facial image and the questionnaire survey results to the analysis server 2810 through the communication device of the user device 2820. Alternatively, the processor of the user device 2820 may transmit the facial image and questionnaire survey results to the analysis server 2810 via another external device. The specific details related to transmitting the facial image and questionnaire survey results have been described in 4. Treatment process monitoring, 10. Clinical trial monitoring, and 11. Post-treatment monitoring, so a duplicate description is omitted.

The processor of the user device 2820 may receive the patient's personalized estimates from the analysis server 2810 through the communication device of the user device 2820. The patient's personalized estimates may include information on the exophthalmos degree information, CAS information, diplopia information, and the like, and the specific details related to the personalized estimates have been described in 4. Treatment process monitoring, 10. Clinical trial monitoring, and 11. Post-treatment monitoring, so a duplicate description is omitted.

The processor of the user device 2820 may display the patient's personalized estimates through the user interface of the user device 2820. The specific details related to displaying the personalized estimates have been described in 4. Treatment process monitoring, so a duplicate description is omitted.

The processor of the user device 2820 may receive patient data from the analysis server 2810 and/or the medical server 2830 through the communication device of the user device 2820. The processor of the user device 2820 may display the patient data through the user interface of the user device 2820. The specific details related to the patient data have been described in 4. Treatment process monitoring, 10. Clinical trial monitoring, and 11. Post-treatment monitoring, so a duplicate description is omitted.

The processor of the user device 2820 may display the patient's facial image through the user interface of the user device 2820. The specific details related to displaying the facial image have been described above in 9. Displaying facial image comparative data, so a duplicate description is omitted.

The processor of the user device 2820 may receive a message for suggesting the hospital visit from the analysis server 2810 through the communication device of the user device 2820. The processor of the user device 2820 may display the message for suggesting the hospital visit through the user interface of the user device 2820. The specific details related to the message for suggesting the hospital visit have been described in 4. Treatment process monitoring and 11. Post-treatment monitoring, so a duplicate description is omitted.

The processor of the user device 2820 may display information, messages, and/or additional data related to side effects through the user interface of the user device 2820. The specific details related to the information, messages, and/or additional data related to the side effects have been described in 4. Treatment process monitoring and 11. Post-treatment monitoring, so a duplicate description is omitted.

The processor may be implemented with components such as a central processing unit, a graphics processing unit, a digital signal processing unit, a state machine, an application-specific integrated circuit, a radio frequency integrated circuit, and a combination thereof.

The user device 2820 may include a user input device and/or a photographing device such as a smartphone, a tablet, a desktop, a laptop, and a digital camera.

Meanwhile, although the user device 2820 and the analysis server 2810 are described as being distinguished from each other, the user device 2820 and the analysis server 2810 may also be implemented as a single device.

(3) Medical Server

The medical server 2830 may be a server device provided in a hospital where a patient visits. Alternatively, the medical server 2830 may be a server device managed by the hospital where the patient visits. Alternatively, the medical server 2830 may be a user device used by medical staff assigned at the hospital. The medical server 2830 may perform the actions performed by the hospital described above in 4. Treatment process monitoring, 10. Clinical trial monitoring, and 11. Post-treatment monitoring.

The medical server 2830 may include a user interface, a communication device, memory, and a processor.

The user interface of the medical server 2830 may output various kinds of information according to control commands of the medical server 2830. The user interface of the medical server 2830 may include a display for visually outputting information to the medical staff. The user interface of the medical server 2830 may include a speaker for audibly outputting information to the medical staff.

The user interface of the medical server 2830 may receive various kinds of information from the medical staff. The medical staff may enter various kinds of information through the user interface of the medical server 2830. The user interface of the medical server 2830 may include input devices such as a keyboard, a mouse, and/or a touch screen.

The communication device of the medical server 2830 may transmit and/or receive data and/or information to and/or from the outside through wired and/or wireless communication. The communication device may perform bidirectional or unidirectional communication.

The communication device of the medical server 2830 may include a wireless communication module and/or a wired communication module. The wireless communication module may include a Wi-Fi communication module, a cellular communication module, etc.

The memory of the medical server 2830 may store various processing programs, parameters for processing the programs, data as results obtained through such processing and the like. For example, the memory of the medical server 2830 may store instructions, algorithms, and/or executable codes for the actions of the processor of the medical server 2830 described below.

The memory of the medical server 2830 may store patient data. The patient data may include data obtained from the patient by the medical staff. In addition, the patient data may include patient data obtained from the analysis server 2810. The specific details related to the patient data have been described in 4. Treatment process monitoring, 10. Clinical trial monitoring, and 11. Post-treatment monitoring, so a duplicate description is omitted.

The memory of the medical server 2830 may store the patient's personalized estimates obtained from the analysis server 2810. The patient's personalized estimates may include exophthalmos degree information, CAS information, and diplopia information, and the specific details related to the personalized estimates have been described in 4. Treatment process monitoring, 10. Clinical trial monitoring, and 11. Post-treatment monitoring, so a duplicate description is omitted.

The memory may be implemented with a nonvolatile semiconductor memory, HDD, SSD, SDD, flash memory, RAM, ROM, EEPROM, or other types of nonvolatile recording media.

The processor of the medical server 2830 may control the overall action of the medical server 2830 and may perform the actions according to the instructions, algorithms, and/or executable codes stored in the memory of the medical server 2830.

The processor of the medical server 2830 may transmit patient data to the analysis server 2810 through the communication device of the medical server 2830. Alternatively, the processor of the medical server 2830 may transmit the patient data to the analysis server 2810 via another external device. The specific details related to transmitting the patient data have been described in 4. Treatment process monitoring, 10. Clinical trial monitoring, and 11. Post-treatment monitoring, so a duplicate description is omitted.

The processor of the medical server 2830 may receive the patient's personalized estimates from the analysis server 2810 through the communication device of the medical server 2830. The patient's personalized estimates may include information on the exophthalmos degree information, CAS information, diplopia information, and the like, and the specific details related to the personalized estimates have been described in 4. Treatment process monitoring, 10. Clinical trial monitoring, and 11. Post-treatment monitoring, so a duplicate description is omitted.

The processor of the medical server 2830 may display the patient's personalized estimates through the user interface of the medical server 2830. The specific details related to displaying the personalized estimates have been described in 4. Treatment process monitoring, so a duplicate description is omitted.

The processor of the medical server 2830 may receive patient data from the analysis server 2810 and/or the user device 2820 through the communication device of the medical server 2830. The processor of the medical server 2830 may display the patient data through the user interface of the medical server 2830. The specific details related to the patient data have been described in 4. Treatment process monitoring, 10. Clinical trial monitoring, and 11. Post-treatment monitoring, so a duplicate description is omitted.

The processor of the medical server 2830 may display a facial image of the patient through the user interface of the medical server 2830. The specific details related to displaying the facial image have been described above in 9. Displaying facial image comparative data, so a duplicate description is omitted.

The processor of the medical server 2830 may receive a notification of the patient's thyroid ophthalmopathy recurrence from the analysis server 2810 through the communication device of the medical server 2830. The processor of the medical server 2830 may display the notification of the patient's thyroid ophthalmopathy recurrence through the user interface of the medical server 2830. The specific details related to the notification of the patient's thyroid ophthalmopathy recurrence have been described in 4. Treatment process monitoring and 11. Post-treatment monitoring, so a duplicate description is omitted.

The processor of the medical server 2830 may display information, messages, and/or additional data related to the side effects through the user interface of the medical server 2830. The specific details related to the information, messages, and/or additional data related to the side effects have been described in 4. Treatment process monitoring and 11. Post-treatment monitoring, so a duplicate description is omitted.

The processor may be implemented with components such as a central processing unit, a graphics processing unit, a digital signal processing unit, a state machine, an application-specific integrated circuit, a radio frequency integrated circuit, and a combination thereof.

Meanwhile, although the medical server 2830 and the analysis server 2810 are described as being distinguished from each other, the medical server 2830 and the analysis server 2810 may be implemented as a single device.

Meanwhile, the medical server 2830 may not be included in the medicine effectiveness monitoring system 2800.

(4) Pharmaceutical Company Server

The pharmaceutical company server 2240 may be a server device provided at a pharmaceutical company of a medicine. Alternatively, the pharmaceutical company server 2240 may be a server device managed by the pharmaceutical company of the medicine.

The pharmaceutical company server 2240 may include a communication device, memory, and a processor.

The communication device of the pharmaceutical company server 2240 may transmit and/or receive data and/or information to and/or from the outside through wired and/or wireless communication. The communication device may perform bidirectional or unidirectional communication.

The communication device of the pharmaceutical company server 2240 may include a wireless communication module and/or a wired communication module. The wireless communication module may include a Wi-Fi communication module, a cellular communication module, etc.

The memory of the pharmaceutical company server 2240 may store various processing programs, parameters for processing the programs, data as results obtained through such processing and the like. For example, the memory of the pharmaceutical company server 2240 may store instructions, algorithms, and/or executable codes for the actions of the processor of the pharmaceutical company server 2240 described below.

The memory of the pharmaceutical company server 2240 may store the patient data obtained from the analysis server 2810 and/or the medical server 2830. The specific details regarding the types of patient data have been described in 4. Treatment process monitoring, 10. Clinical trial monitoring, and 11. Post-treatment monitoring, so a duplicate description is omitted.

The memory of the pharmaceutical company server 2240 may store the patient's personalized estimates obtained from the analysis server 2810. The patient's personalized estimates may include exophthalmos degree information, CAS information, and diplopia information, and the specific details related to the personalized estimates have been described in 4. Treatment process monitoring, 10. Clinical trial monitoring, and 11. Post-treatment monitoring, so a duplicate description is omitted.

The memory of the pharmaceutical company server 2240 may store clinical trial data obtained from the analysis server 2810. The specific details regarding the clinical trial data have been described in 10. Clinical trial monitoring, so a duplicate description are omitted.

The memory may be implemented with a nonvolatile semiconductor memory, HDD, SSD, SDD, flash memory, RAM, ROM, EEPROM, or other types of nonvolatile recording media.

The processor of the pharmaceutical company server 2240 may control the overall action of the pharmaceutical company server 2240 and may perform the actions according to instructions, algorithms, and/or executable codes stored in the memory of the pharmaceutical company server 2240.

The processor of the pharmaceutical company server 2240 may receive patient data from the analysis server 2810 and/or the medical server 2830 through the communication device of the pharmaceutical company server 2240. The specific details related to the patient data have been described in 4. Treatment process monitoring, 10. Clinical trial monitoring, and 11. Post-treatment monitoring, so a duplicate description is omitted.

The processor of the pharmaceutical company server 2240 may receive the patient's personalized estimates from the analysis server 2810 through the communication device of the pharmaceutical company server 2240. The patient's personalized estimates may include information on the exophthalmos degree information, CAS information, diplopia information, and the like, and the specific details related to the personalized estimates have been described in 4. Treatment process monitoring, 10. Clinical trial monitoring, and 11. Post-treatment monitoring, so a duplicate description is omitted.

The processor of the pharmaceutical company server 2240 may receive clinical trial data from the analysis server 2810 through the communication device of the pharmaceutical company server 2240.

The specific details regarding the clinical trial data have been described in 10. Clinical trial monitoring, so a duplicate description are omitted.

The processor of the pharmaceutical company server 2240 may receive side effect occurrence information from the analysis server 2810 through the communication device of the pharmaceutical company server 2240. The specific details related to the side effect occurrence information have been described in 10. Clinical trial monitoring, so a duplicate description is omitted.

The processor may be implemented with components such as a central processing unit, a graphics processing unit, a digital signal processing unit, a state machine, an application-specific integrated circuit, a radio frequency integrated circuit, and a combination thereof.

Meanwhile, the pharmaceutical company server 2240 may not be included in the medicine effectiveness monitoring system 2800.

13. Additional Exemplary Embodiment (1) Other Patients to Whom the Treatment Process Monitoring Method is Applicable According to the present disclosure, the patient's personalized estimates may be determined on the basis of the facial image and questionnaire survey content obtained from the patient. In this case, the patient's personalized estimates may be information related to the patient's condition for thyroid ophthalmopathy.

That is, by using the method for monitoring the patient described above in 4. Treatment process monitoring and 11. Post-treatment monitoring, the patient's thyroid ophthalmopathy condition may be monitored, and the patient who is a target for monitoring is not necessarily limited to a patient who has been administered a thyroid ophthalmopathy medicine. For example, the monitoring methods described above in 4. Treatment process monitoring and 11. Post-treatment monitoring may be applied to various types of thyroid ophthalmopathy-related patients including: patients with thyroid ophthalmopathy, patients undergoing treatment for thyroid ophthalmopathy, patients who have been treated for thyroid ophthalmopathy, patients administered a medicine other than a medicine for the purpose of treating thyroid ophthalmopathy, and/or patients who have undergone surgery for thyroid ophthalmopathy.

(2) Diseases in which Exophthalmos Monitoring Method is Applicable

According to the present disclosure, an exophthalmos degree may be determined on the basis of a facial image.

That is, according to the present disclosure, an exophthalmos degree may be determined on the basis of a facial image obtained from a patient, so patients with other diseases related to exophthalmos may also be monitored by using the methods according to the present disclosure.

For example, the patients that may be monitored by using the methods according to the present disclosure may include patients with orbital inflammation and/or patients with orbital tumors, but it is not limited thereto.

(3) Diseases in which Eyelid Monitoring Method is Applicable

According to the present disclosure, the degree of eyelid retraction may be determined on the basis of a facial image.

That is, according to the present disclosure, the degree of eyelid retraction may be determined on the basis of a facial image obtained from a patient, and thus, patients with other diseases related to eyelid retraction symptoms may also be monitored by using the method according to the present disclosure.

For example, patients that may be monitored by using the method according to the present disclosure may include patients with ptosis, but it is not limited thereto.

14. System for Estimating Eye-Related Variables (1) A Method for Estimating MRD1, MRD2 and/or Radial MPLD Values Based on the Facial Image Hereinafter, the method for estimating the MRD1, MRD2 and/or Radial MPLD values from the facial image will be described.

A facial image may be obtained from a patient. Specifically, the facial image may be obtained from the patient's user device, and the facial image may be an image captured by the patient's user device. It is not limited to thereto, and a facial image may also be obtained from a hospital. Specifically, the facial image may be obtained by allowing medical staff assigned at the hospital to capture the patient's facial when the patient visits the hospital.

The facial image may be an image of an area between the lower end of a nose and the upper end of an eyebrow. Specifically, the facial image may be captured from a frontal view of the patient's facial, showing the area between the lower end of the nose and the upper end of the eyebrow. This is not limited thereto, and the facial image may mean an image that shows an eye region.

The eyeball area and pupil and iris area may be detected by applying pre-trained image segmentation model to the facial image.

Figure 29:
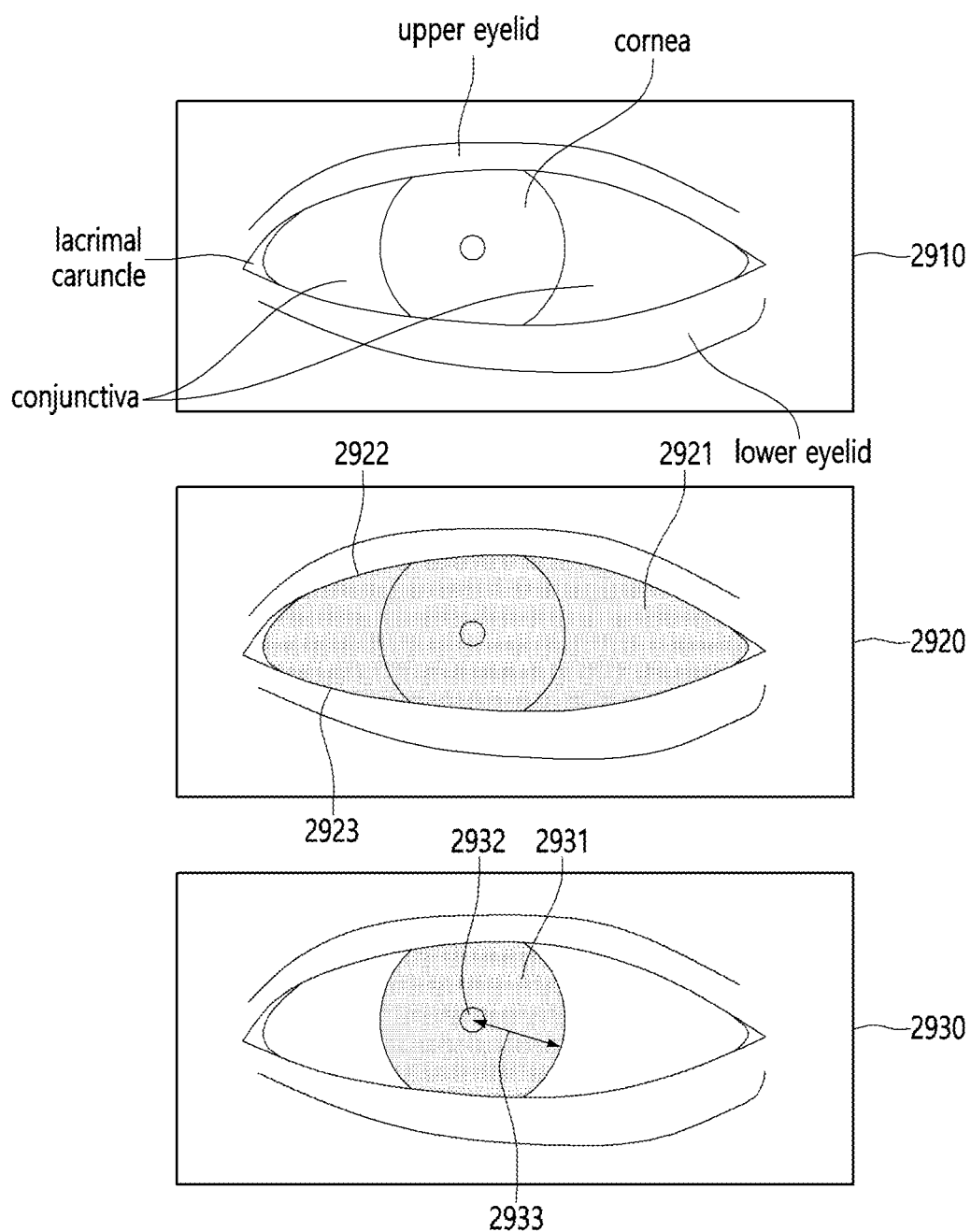
FIG. 29 is a view illustrating the structure of the eye, an eyeball area, and a pupil and iris area.

FIG. 29 is a view illustrating the structure of the eye, an eyeball area, and a pupil and iris area.

Referring to FIG. 29, the eye shown in facial image 2910 may include an upper eyelid, a lower eyelid, a lacrimal caruncle, a conjunctiva, and a cornea.

In this case, the eye shown in the facial image may have some parts of the conjunctiva and cornea covered by the upper eyelid, lower eyelid, and lacrimal caruncle, and the other parts of the conjunctiva and cornea may be exposed.

As illustrated in FIG. 29, a facial image 2920 in which an eyeball area 2921 is detected may be obtained by applying an image segmentation model to a facial image 2910. For a specific example, a face may be identified from a captured facial image by using a library such as MediaPipe. Then, the identified face may be applied to the image segmentation model so that a facial image 2920 in which the eyeball area 2921 is detected may be obtained.

The eyeball area 2921 may be identified as the part of the eye that is exposed externally and is not covered by the upper and lower eyelids in the facial image which is captured while the person has their eyes open. Specifically, the image segmentation model may identify the area of the eye that is exposed externally and not covered by the upper and lower eyelids as the eyeball area 2921 in the facial image. Although the eyeball area 2921 illustrated in FIG. 29 is depicted as not including a lacrimal caruncle, the eyeball area 2921 may include a lacrimal caruncle. In other words, the eyeball area 2921 may refer to any area of the eye located between the upper and lower eyelids, including the lacrimal caruncle.

When training the image segmentation model, all pixels corresponding to the exposed area of the eye, including the lacrimal caruncle, which is not covered by the upper and lower eyelids in the facial image, may be selected, and the area containing these pixels may be labeled as the eyeball area 2921.

Eyeball and eyelid boundaries 2922 and 2923 may be identified on the basis of the detected eyeball area 2921. Specifically, the boundary 2922 between the eyeball and the upper eyelid may mean an upper boundary of the eyeball area 2921, and the boundary 2923 between the eyeball and the lower eyelid may mean a lower boundary of the eyeball area 2921.

As shown in FIG. 29, a facial image 2930 in which the pupil and iris area 2931 is detected may be obtained by applying an image segmentation model to the facial image 2910. For a specific example, a face may be identified from a captured facial image by using a library such as MediaPipe. Then, the identified face may be applied to the image segmentation model so that a facial image 2930 in which the pupil and iris area 2931 is detected may be obtained.

The pupil and iris area 2931 may be a part of the cornea that is exposed to the outside and not covered by the upper and lower eyelids in a facial image captured when a person's eyes are open.

The pupil and iris area 2931 may be specified as the smallest circle that includes all pixels that appear as pupil and iris. Specifically, the image segmentation model may identify the smallest circle that includes all pixels that appear as pupil and iris in a facial image as the pupil and iris area 2931.

For example, if the pupil and iris area 2931 is to be identified in a facial image of a person whose color of eyes are black, the image segmentation model may select all black pixels in the facial image, then find the smallest circle that may include all black pixels, and then identify the pupil and iris area 2931 based on the found smallest circle.

For another example, if the pupil and iris area 2931 is to be identified in a facial image of a person whose color of eyes are blue, the image segmentation model may select all blue pixels in the facial image, then find the smallest circle that may include all blue pixels, and then identify the pupil and iris area 2931 based on the found smallest circle.

The image segmentation model may be trained by selecting all pixels that appear as pupil and iris in a facial image, finding the smallest circle that may include all of these pixels, and then specifying and labeling the pupil and iris area 2931 based on the smallest circle found.

In the case of identifying both the eyeball area 2921 and the pupil and iris area 2931 through one image segmentation model, the training data of the image segmentation model may consist of the facial image 2910 and the corresponding eyeball area 2921 and pupil and iris area 2931.

The center position of pupil and iris 2932 may be identified based on the pupil and iris area 2931 detected through the image segmentation model. Specifically, the center point of a circle (i.e., the smallest circle including all pixels that appear as pupil and iris) specified as the pupil and iris area 2931 in the facial image may be identified as the center position of pupil and iris 2932. For example, the center position of pupil and iris 2932 may be identified as a single pixel, but is not limited thereto.

The pixel distance 2933 corresponding to the radius of pupil and iris may be calculated based on the pupil and iris area 2931 detected through the image segmentation model. Specifically, the radius of a circle (i.e., the smallest circle including all pixels that appear as pupil and iris) specified as the pupil and iris area 2931 in the facial image may be identified as the pixel distance 2933 corresponding to the radius of pupil and iris.

Meanwhile, the image segmentation model used to detect the eyeball area and the image segmentation model used to detect the pupil and iris area may be models different from each other. Specifically, the image segmentation model used to detect the eyeball area and the image segmentation model used to detect the pupil and iris area may be separate image segmentation models that are trained by using training data sets different from each other. In this case, before the image segmentation model used to detect the eyeball area and the image segmentation model used to detect the pupil and iris area are trained, the structures of these image segmentation models may be identical to each other. Alternatively, before the image segmentation model used to detect the eyeball area and the image segmentation model used to detect the pupil and iris area are trained, the structures of these image segmentation models may also be different from each other.

Meanwhile, the image segmentation model may be a single image segmentation model trained to detect both of the eyeball area and the pupil and iris area.

A value of pixel distance of MRD1, a value of pixel distance of MRD2 and/or a value of pixel distance of Radial MPLD may be calculated by calculating a distance from the identified center position of pupil and iris to the eyeball and eyelid boundaries.

Figure 30:
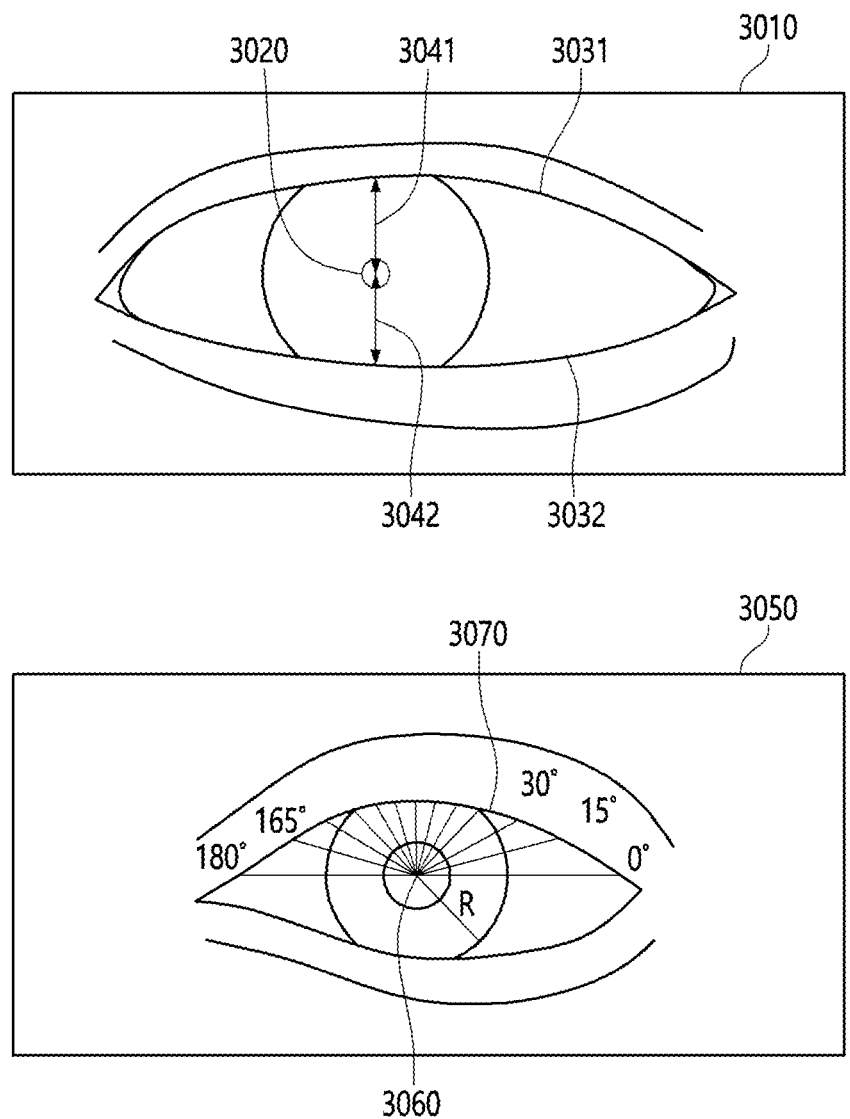
FIG. 30 is a view illustrating MRD1, MRD2 and/or Radial MPLD calculated based on the facial image.

FIG. 30 is a view illustrating MRD1, MRD2 and/or Radial MPLD calculated based on the facial image.

MRD1 (Margin Reflex Distance 1) refers to a value measured from the distance from the light reflection point of the pupil and iris to the point where a line drawn in a vertical direction intersects the upper eyelid.

It is realistically difficult to obtain the light reflection point of the pupil and iris in the measurement of MRD1, MRD2 and/or Radial MPLD using a mobile terminal according to one embodiment of the present application.

In other words, there must be an action such as shining a 'flash' on the eye, but the design of the mobile terminal rarely allows a way to shine a flash in selfie mode, and even if it is shined, it is difficult to establish a shooting environment in which a light reflection point is formed on the eye.

Accordingly, the applicant of the present application decided to calculate MRD1 based on the center of the pupil and iris (i.e., pupil and iris area) rather than the light reflection point of the pupil and iris, and evaluated whether the MRD1 calculated based on this method is similar to the actual MRD1 (i.e., whether it is valid as a prediction method), and an experimental example related thereto is described below.

The value of pixel distance 3041 of MRD1 may be calculated based on the center position of pupil and iris 3020 and the boundary 3031 between the eyeball and the upper eyelid. Specifically, when a line is drawn vertically from the center position of pupil and iris 3020, the value of pixel distance from the point where the line intersects the boundary 3031 between the eyeball and the upper eyelid to the center position of pupil and iris 3020 may be measured as the value of pixel distance 3041 of MRD1. In this case, the value of pixel distance 3041 of MRD1 may be calculated based on the center position pupil and iris 3020 identified by the trained image segmentation model, not the light reflection point.

Since the pixel distance must be obtained first by drawing a line in the vertical direction in the calculation of MRD1, it is very important that the horizontal level of the eyes is set consistently.

Therefore, to align the horizontal level of the eyes, preprocessing may be performed to identify the center positions of the pupil and iris of both eyes included in the facial image, and rotate the facial image such that the y-coordinates of the identified center positions of the pupil and iris are the same.

In the case of the above-described horizontal adjustment action, both eyes should be included in the facial image rather than when only one eye is included since the center positions of the pupils of both eyes are used.

If only one eye is included in the facial image, the above-described horizontal adjustment action may be omitted, in which case some accuracy may be lost.

MRD2 (Margin Reflex Distance 2) refers to a value measured from the distance from the light reflection point of the pupil and iris to the point where a line drawn in a vertical direction intersects the lower eyelid.

Likewise, the applicant of the present application decided to calculate MRD2 based on the center of the pupil and iris (i.e., pupil and iris area) rather than the light reflection point of the pupil and iris, and evaluated whether the MRD2 calculated based on this method is similar to the actual MRD2 (whether it is valid as a prediction method), and an experimental example related thereto is described below.

The value of pixel distance 3042 of MRD2 may be calculated based on the center position of pupil and iris 3020 and the boundary 3032 between the eyeball and the lower eyelid. Specifically, when a line is drawn vertically from the center position of pupil and iris 3020, the value of pixel distance from the point where the line intersects the boundary 3032 between the eyeball and the lower eyelid to the center position of pupil and iris 3020 may be measured as the value of pixel distance 3042 of MRD2. In this case, the value of pixel distance 3042 of MRD2 may be calculated based on the center position pupil and iris 3020 identified by the trained image segmentation model, not the light reflection point.

Since the pixel distance must be obtained first by drawing a line in the vertical direction in the calculation of MRD2, it is very important that the horizontal level of the eyes is set consistently.

Therefore, the above-described horizontal adjustment action may be performed to align the horizontal level of the eyes before obtaining the value of pixel distance of MRD2.

Radial MPLD refers to the distance from the center of the eye to the eyeball and eyelid boundaries by angle.

According to one embodiment, the value of pixel distance of the Radial MPLD displayed on the facial image 3050 may be calculated as a value measuring the pixel distance from the center position of pupil and iris 3060 to the eyeball and eyelid boundaries 3070 by angle. The angle may be distinguished in 15-degree units with the x-axis direction as 0 degrees, and the value of pixel distance of the Radial MPLD may be calculated for each distinguished angle.

Meanwhile, the value of pixel distance of the Radial MPLD is based on the x-axis direction of the facial image as 0 degrees, so the facial image needs to be horizontally leveled before the Radial MPLD value is calculated.

In order to align the horizontal level of the eyes, preprocessing may be performed to identify the center positions of the pupil and iris of both eyes included in the facial image, and rotate the facial image such that the y-coordinates of the identified center positions of the pupil and iris are the same.

In the case of the above-described horizontal adjustment action, both eyes should be included in the facial image rather than when only one eye is included since the center positions of the pupils of both eyes are used.

If only one eye is included in the facial image, the above-described horizontal adjustment action may be omitted. In that case, if the patient's facial was photographed in a tilted state in the facial image, some of the estimation accuracy of the MRD1, MRD2, and/or Radial MPLD values may be lost.

In some cases, if the group using the method for measuring MRD1, MRD2, and Radial MPLD according to the present application is a group with many 'strabismus patients', MRD1, MRD2, and Radial MPLD may be calculated with the horizontal adjustment operation omitted. This is because strabismus patients generally have their center positions of pupil and iris not aligned horizontally, and thus, if horizontal alignment is performed such that the center positions of the pupil and iris are aligned, the accuracy of MRD1, MRD2, and Radial MPLD may decrease.

The value of pixel distance of MRD1, the value of pixel distance of MRD2, and/or the value of pixel distance of Radial MPLD calculated based on the facial image may differ from the patient's actual MRD1 value, MRD2 value, and/or Radial MPLD value depending on the distance between the patient and the user device that photographs the patient.

Therefore, the pixel distance calculated based on the facial image needs to be converted into an actual distance.

Hereinafter, a method for calculating an actual distance corresponding to each of the pixel distance of MRD1, the pixel distance of MRD2, and/or the pixel distance of Radial MPLD is described.

According to one embodiment, the pixel distance of MRD1 calculated based on the facial image may be calculated as an actual distance using the actual length of the radius of pupil and iris. Specifically, the MRD1 calculated as a pixel distance may be calculated as an actual distance based on the pixel distance corresponding to the radius of pupil and iris, and the actual length of the radius of pupil and iris.

The actual length of a radius of a pupil and iris is generally similar among people of the same type. Specifically, the actual length of the radius of the pupil and iris may be 5.735 mm for men and 5.585 mm for women. Meanwhile, the actual length of the radius of the pupil and iris may vary depending on people's race and/or age.

Since the actual length of the radius of the pupil and iris is similar among people of the same type, it is possible to predetermine the actual length of a radius of a pupil and iris, which is differentiated by gender, race, and/or age.

Accordingly, the actual length of the radius of the pupil and iris corresponding to the facial image may be obtained from the actual length of the radius of the pupil and iris predetermined on the basis of the patient's gender, race, and/or age included in patient data.

An actual distance of MRD1 may be calculated by using a pixel distance corresponding to a radius of a pupil and iris, an actual distance of the radius of the pupil and iris, and a pixel distance of MRD1. In this case, the pixel distance corresponding to the radius of a pupil and iris may be calculated based on the detected pupil and iris area.

Specifically, the actual distance of MRD1 may be calculated by multiplying a ratio value of the pixel distance corresponding to the radius of a pupil and iris calculated from the facial image and the actual distance of the radius of the pupil and iris by the pixel distance of MRD1.

This method, which utilizes the fact that the size of the radius of pupil and iris is similar among people of the same type, has the advantage of being able to obtain the actual distances of MRD1, MRD2 and/or Radial MPLD with ease and high accuracy.

Specifically, it is difficult to obtain highly accurate MRD1, MRD2, and/or Radial MPLD values by applying an artificial intelligence model to a facial image of a patient's facial. In addition, there are inconveniences such as having to obtain the facial image by attaching a separate marker, such as a sticker whose actual size is known in advance, to the patient's face since the ratio of the pixel distance obtained from the facial image and the actual distance varies depending on the distance between the subject being captured and the camera.

However, as described above, the present disclosure discloses that the actual distances of MRD1, MRD2 and/or Radial MPLD may be easily and accurately obtained by capturing only the patient's face without the patient using a separate marker such as a sticker by utilizing the actual length of the radius of the pupil and iris predetermined on the basis of the patient's gender, race, and/or age.

(2) The System for Estimating Eye-Related Variables

The system for estimating eye-related variables may estimate the actual distance of MRD1, the actual distance of MRD2, and/or the actual distance of Radial MPLD corresponding to the facial image.

Specifically, the system for estimating eye-related variables may estimate the actual distance of MRD1, the actual distance of MRD2, and/or the actual distance of Radial MPLD corresponding to the facial image by using the estimation method of estimating the values of MRD1, MRD2, and/or Radial MPLD based on the facial image described above.

Hereinafter, the system for estimating eye-related variables are described.

Figure 31:
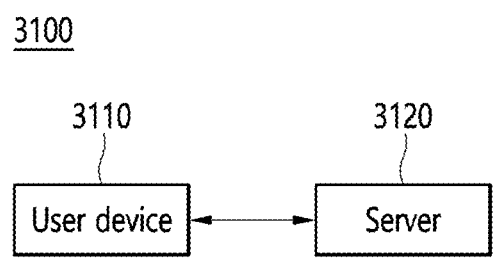
FIG. 31 is a view illustrating the system for estimating eye-related variables.

FIG. 31 is a view illustrating the system for estimating eye-related variables.

Referring to FIG. 31, the system 3100 for estimating eye-related variables may comprise a user device 3110 and server 3120.

(1) User Device 3110

A user device 3110 is a device that interacts directly and/or indirectly with a patient.

The user device 3110 may include a camera module, a user interface, a communication device, memory, and a processor.

The camera module of the user device 3110 is a digital camera module and may include an image sensor and an image processing unit. The image sensor is a device for converting an optical image into electrical signals, and may be composed of a chip having a plurality of photo diodes integrated therein. For example, the image sensor may include a Charge Coupled Device CCD, a Complementary Metal Oxide Semiconductor CMOS, etc. The image processing unit may generate image information by performing image processing on the photographed results.

The user interface of the user device 3110 may output various information according to control commands of the processor of the user device 3110. The user interface of the user device 3110 may include a display for visually outputting information to a patient. The user interface of the user device 3110 may include a speaker for audibly outputting information to the patient.

The user interface of the user device 3110 may receive input of various kinds of information from the patient. The patient may enter various kinds of information through the user interface of the user device 3110. The user interface of the user device 3110 may include input devices such as a keyboard, a mouse, and/or a touch screen.

The communication device of the user device 3110 may transmit and/or receive data and/or information to and/or from the outside through wired and/or wireless communication. The communication device may perform bidirectional or unidirectional communication.

The communication device of the user device 3110 may include a wireless communication module and/or a wired communication module. The wireless communication module may include a Wi-Fi communication module, a cellular communication module, etc.

The memory of the user device 3110 may store various processing programs, parameters for processing programs, data as results obtained through such processing and the like. For example, the memory of the user device 3110 may store instructions, algorithms, and/or executable codes for the actions of the processor of the user device 3110 described below.

The memory of the user device 3110 may store a facial image captured through the camera module.

The memory of the user device 3110 may store the actual distance of MRD1, actual distance of MRD2 and/or actual distance of Radial MPLD obtained from the server 3120.

The memory of the user device 3110 may store patient data obtained from the server 3120. The specific details regarding the types of patient data have been described in 4. Treatment process monitoring, 10. Clinical trial monitoring, and 11. Post-treatment monitoring, so a duplicate description is omitted.

The memory may be implemented with a nonvolatile semiconductor memory, HDD, SSD, SDD, flash memory, RAM, ROM, EEPROM, or other types of nonvolatile recording media.

The processor of the user device 3110 may control the overall action of the user device 3110 and may perform the actions according to instructions, algorithms, and/or executable codes stored in the memory of the user device 3110.

The processor of the user device 3110 may receive a request for capturing a facial image from the server 3120 through the communication device of the user device 3110.

The processor of the user device 3110 may capture the patient's facial image by using the camera module of the user device 3110. The specific details on facial image capture have been described above, so a duplicate description IS omitted.

The processor of the user device 3110 may transmit the facial image to the server 3120 through the communication device of the user device 3110. Alternatively, the processor of the user device 3110 may transmit the facial to the server 3120 via another external device. The specific details related to transmitting the facial image have been described in 4. Treatment process monitoring, 10. Clinical trial monitoring, and 11. Post-treatment monitoring, so a duplicate description is omitted.

The processor of the user device 3110 may receive the actual distance of MRD1, actual distance of MRD2 and/or actual distance of Radial MPLD from the server 3120 through the communication device of the user device 3110.

The processor of the user device 3110 may display the actual distance of MRD1, actual distance of MRD2 and/or actual distance of Radial MPLD through the user interface of the user device 3110.

According to one embodiment, the processor of the user device 3110 may provide the obtained actual distance of MRD1, the actual distance of MRD2, and/or the actual distance of Radial MPLD as specific numerical values through the user interface. Specifically, the numerical values may be provided for each of the two eyes through the user interface. For example, if the actual distance of MRD1 for the left eye is estimated to be 2.7 mm and the actual distance of MRD1 for the right eye is estimated to be 3 mm, the processor of the user device 3110 may provide the value of MRD1 for the left eye as 2.7 mm and the value of MRD1 for the right eye as 3 mm through the user interface of the user device 3110.

According to one embodiment, the processor of the user device 3110 may provide a graph of the actual distance of MRD1, the actual distance of MRD2, and/or the actual distance of Radial MPLD obtained through the user interface.

Figure 32:
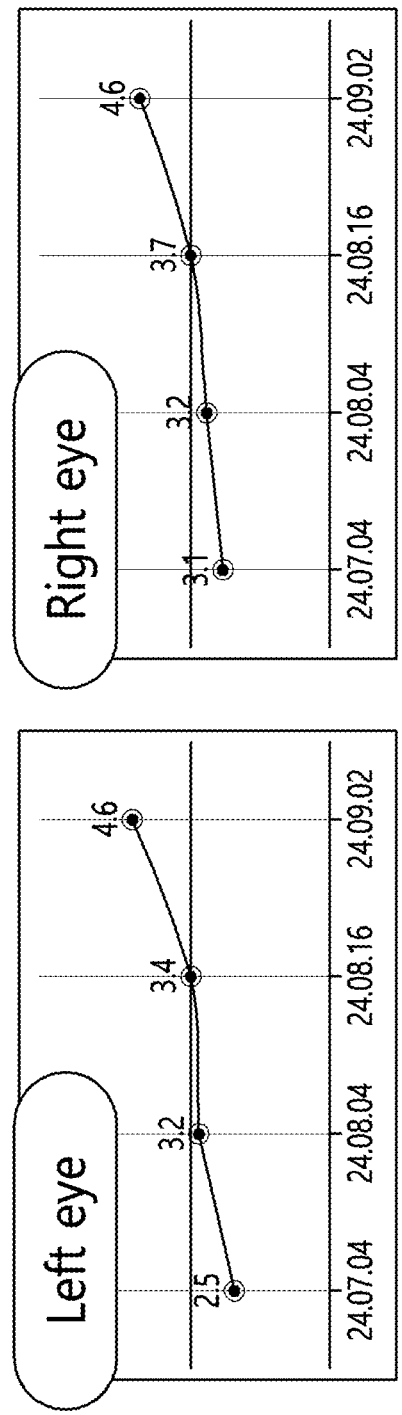
FIG. 32 is a view illustrating a UI that provides a graph of the actual distance of MRD1, the actual distance of MRD2, and/or the actual distance of Radial MPLD according to one embodiment.

FIG. 32 is a view illustrating a UI that provides a graph of the actual distance of MRD1, the actual distance of MRD2, and/or the actual distance of Radial MPLD according to one embodiment.

Referring to FIG. 32, the processor of the user device 3110 may provide a line graph of the estimated actual distance of MRD1, the actual distance of MRD1, and/or the actual distance of Radial MPLD on a daily and/or weekly basis through the user interface.

As another example, although not illustrated separately, the processor of the user device 3110 may provide a bar graph of the estimated actual distance of MRD1, the actual distance of MRD1, and/or the actual distance of Radial MPLD on a daily and/or weekly basis through the user interface.

According to one embodiment, the processor of the user device 3110 may provide the actual distance of Radial MPLD as a picture, by visualizing, rather than a specific number through a user interface.

Figure 33A:
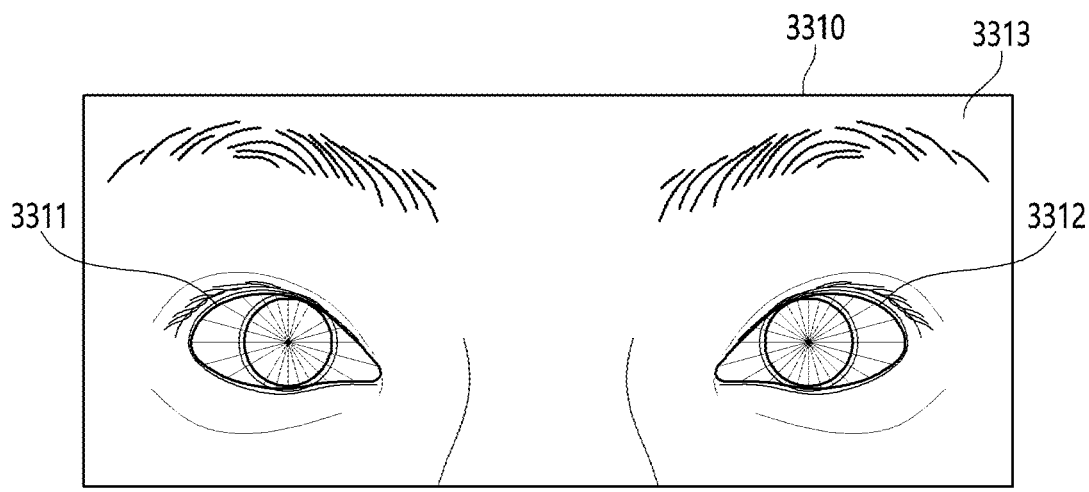
FIGS. 33A and 33B are views illustrating a UI providing a visualized Radial MPLD according to one embodiment.
Figure 33B:
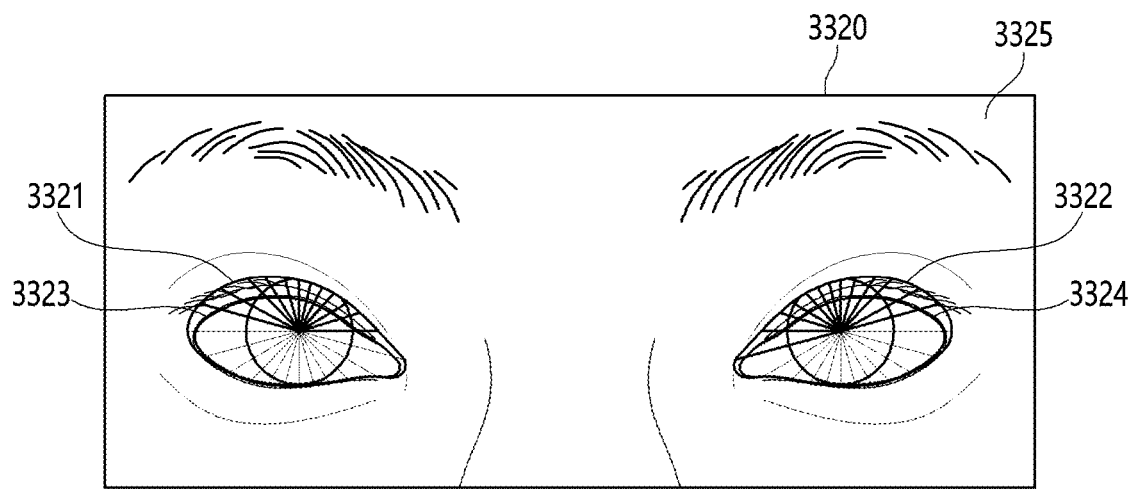

FIGS. 33A and 33B are views illustrating a UI providing a visualized Radial MPLD according to one embodiment.

Referring to FIG. 33A, the UI providing a visualized Radial MPLD may include a visualization interface 3310, a visualization indicator 3311 and 3312, and a facial image 3313.

The visualization interface 3310 may display the visualization indicator 3311, 3312 and the facial image 3313.

The visualization indicators 3311 and 3312 may be a Radial MPLD that is visualized and displayed as a picture.

The visualization indicators 3311 and 3312 may include lines indicating the outline of the pupil and iris area, the outline of the eyeball area, and the distance of the Radial MPLD at each angle.

As shown in FIG. 33A, the visualization indicators 3311 and 3312 may be displayed at the eye positions of the facial image 3313.

For a specific example, as shown in FIG. 33A, the visualization indicator 3311 may display the outline of the eyeball area, the outline of the pupil area, and the angular distance of the Radial MPLD as lines corresponding to the patient's right eye in the facial image.

For another example, as shown in FIG. 33A, the visualization indicator 3312 may display the outline of the eyeball area, the outline of the pupil area, and the angular distance of the Radial MPLD as lines corresponding to the patient's left eye in the facial image.

According to one embodiment, the processor of the user device 3110 may provide the visualization indicators by overlapping them on one facial image through a user interface.

Referring to FIG. 33B, the UI providing the visualized Radial MPLD may include a visualization interface 3320, visualization indicators 3321, 3322, 3323, 3324, and a facial image 3325.

The visualization indicators 3321, 3322, 3323, 3324 may be displayed by overlapping them on one facial image 3325. Specifically, first visualization indicators 3321, 3322 obtained based on a first facial image captured at a first time point and second visualization indicators 3323, 3324 obtained based on a second facial image captured at a second time point may be displayed in a state of being overlapped on one facial image 3325.

At this time, the visualization indicators 3321, 3322, 3323, 3324 may be displayed in a state of being overlapped on one facial image 3325 by adjusting the center position of pupil and iris and the size of the pupil of the visualization indicators 3321, 3322, 3323, 3324 to be the same.

For example, if the second visualization indicator 3323, 3324 is a currently obtained Radial MPLD and the first visualization indicator 3321, 3322 is a previously obtained Radial MPLD, the size and position of the first visualization indicator 3321, 3322 may be adjusted such that the center position of pupil and iris and pupil radius size corresponding to the first visualization indicator 3321, 3322 obtained in the past become identical to the center position of pupil and iris and pupil radius size corresponding to the currently obtained second visualization indicator 3323, 3324.

At this time, as shown in FIG. 33B, the second visualization indicator 3323 may display the outline of the eyeball area, the outline of the pupil and iris area, and the angular distance of the Radial MPLD as lines, corresponding to the patient's right eye shown in the second facial image 3325.

The first visualization indicator 3321 may display the outline of the eyeball area, the outline of the pupil and iris area, and the angular distance of the Radial MPLD as lines corresponding to the patient's right eye which are included in the first facial image, not the second facial image 3325.

Accordingly, the first visualization indicator 3321 may be different from the outline of the eyeball area, the outline of the pupil and iris area, and/or the angular distance of the Radial MPLD of the second visualization indicator 3323, but is not limited thereto.

Meanwhile, as shown in FIG. 33B, the second visualization indicator 3324 may display the outline of the eyeball area, the outline of the pupil and iris area, and the angular distance of the Radial MPLD as lines, corresponding to the patient's left eye shown in the second facial image 3325.

The first visualization indicator 3322 may display the outline of the eyeball area, the outline of the pupil and iris area, and the angular distance of the Radial MPLD as lines corresponding to the patient's left eye which are included in the first facial image, not the second facial image 3325.

Accordingly, the first visualization indicator 3322 may be different from the outline of the eyeball area, the outline of the pupil and iris area, and/or the angular distance of the Radial MPLD of the second visualization indicator 3324, but is not limited thereto.

By adjusting the size and position of the visualization indicator in this way, it may be confirmed that the outline of the pupil and iris area of the first visualization indicators 3321, 3322 and the outline of the pupil and iris area of the second visualization indicator 3323, 3324 are displayed overlapping with the same position and size, as shown in FIG. 33B.

As described above, if the Radial MPLD obtained at multiple time points are visualized and displayed in an overlapping state, the change in the Radial MPLD over time may be easily confirmed.

The visualization indicators 3321, 3322, 3323, 3324 may display the distance with a large change among the distances of the Radial MPLD at each angle with an emphasized line. For example, the distances with a large change among the distances of the Radial MPLD may be displayed with a darker color or a different color than the other lines.

The processor of the user device 3110 may receive patient data from the server 3120 through the communication device of the user device 3110. The processor of the user device 3110 may display the patient data through the user interface of the user device 3110. The specific details related to the patient data have been described in 4. Treatment process monitoring, 10. Clinical trial monitoring, and 11. Post-treatment monitoring, so a duplicate description is omitted.

The processor of the user device 3110 may display the patient's facial image through the user interface of the user device 3110.

The processor may be implemented with components such as a central processing unit, a graphics processing unit, a digital signal processing unit, a state machine, an application-specific integrated circuit, a radio frequency integrated circuit, and a combination thereof.

The user device 3110 may include a user input device and/or a photographing device such as a smartphone, a tablet, a desktop, a laptop, and a digital camera.

(2) Server 3120

The server 3120 is a device that estimates and/or determines a patient's condition by using data related to the patient and generates estimated data about the patient.

The server 3120 may include a communication device, memory, and a processor.

The communication device of the server 3120 may transmit and/or receive data and/or information to and/or from the outside through wired and/or wireless communication. The communication device may perform bidirectional or unidirectional communication.

The communication device of the server 3120 may include a wireless communication module and/or a wired communication module. The wireless communication module may include a Wi-Fi communication module, a cellular communication module, etc.

The memory of the server 3120 may store various processing programs, parameters for processing the programs, data as results obtained through such processing and the like. For example, the memory of the server 3120 may store instructions, algorithms, and/or executable codes for the actions of the processor of the server 3120 described below.

The memory of the server 3120 may store a patient's facial image obtained from the user device 3110.

The memory of the server 3120 may store patient data obtained from the user device 3110. The specific details regarding the types of patient data have been described in 4. Treatment process monitoring, 10. Clinical trial monitoring, and 11. Post-treatment monitoring, so a duplicate description is omitted.

The memory of the server 3120 may store the actual distance of MRD1, the actual distance of MRD2 and/or the actual distance of Radial MPLD.

The memory may be implemented as a nonvolatile semiconductor memory, a hard disk drive HDD, a solid state disk SSD, a silicon disk drive SDD, flash memory, a random access memory RAM, a read only memory ROM, an electrically erasable programmable read-only memory EEPROM, other types of tangible nonvolatile recording media, or the like.

The processor of the server 3120 may control the overall action of the server 3120 and may perform actions according to instructions, algorithms, and/or executable codes, which are stored in the memory of the server 3120.

The processor of the server 3120 may receive patient data from the user device 3110 through the communication device of the server 3120. The processor of the server 3120 may request capturing a facial image from the user device 3110 through the communication device of the server 3120. The processor of the server 3120 may receive the facial image from the user device 3110 through the communication device of the server 3120. Specific details on receiving the patient data, requesting the facial image, and receiving the facial image has been described in 4. Treatment process monitoring, 10. Clinical trial monitoring, and 11. Post-treatment monitoring, so a duplicate description is omitted.

The processor of the server 3120 may determine MRD1, MRD2 and/or Radial MPLD values by using the facial images.

The processor of the server 3120 may transmit the MRD1, MRD2 and/or Radial MPLD values and/or patient data to the user device 3110 through the communication device of the server 3120.

The processor of the server 3120 may determine whether the patient's thyroid ophthalmopathy is worsened or not on the basis of the MRD1, MRD2 and/or Radial MPLD values.

Meanwhile, the processor may be implemented with components such as a central processing unit CPU, a graphics processing unit GPU, a digital signal processor DSP, a state machine, an application-specific integrated circuit ASIC, a radio frequency integrated circuit RFIC, and a combination thereof.

Meanwhile, although the user device 3110 and the server 3120 are described as being distinguished from each other, the user device 3110 and the server 3120 may also be implemented as a single device.

(3) Experimental Example of the System for Estimating Eye-Related Variables

Hereinafter, the performance experiment of the system for estimating eye-related variables is described.

The system for estimating eye-related variables is a system that the above-mentioned method for estimating MRD1, MRD2 and/or Radial MPLD values based on the facial image were applied.

The above-mentioned method applied in the system for estimating MRD1, MRD2 and/or Radial MPLD values based on the facial used the image segmentation model that receives, as input, a facial image and outputs a facial image in which the pupil and iris area and the eye area are detected.

In order to conduct an experiment to verify the performance of the system for estimating eye-related variables, 119 test facial images (238 eyes are included in the 119 test facial images) were used as training data for the image segmentation model.

The image segmentation model was trained by (i) selecting all pixels corresponding to the eye that is exposed to the outside, including the lacrimal caruncle, and not covered by the upper and lower eyelids in the facial image, and labeling the region including these pixels as the eyeball area, (ii) selecting all pixels that appear as the color of the pupil and iris in the facial image, finding the smallest circle that may contain all of these pixels, and labeling the pupil and iris area based on the smallest circle found.

The image segmentation model of the system for estimating eye-related variables receives, as input, a facial identified from a test facial image by using a library such as MediaPipe, and outputs a facial image in which the eyeball and eyelid boundaries detected based on the eyeball area, the pupil and iris area, and the center position of pupil and iris detected based on the pupil and iris area.

The system for estimating eye-related variables estimated the eye-related variables MRD1, MRD2, and/or Radial MPLD values using the center position of pupil and iris and the eyeball and eyelid boundaries output by the image segmentation model.

The MRD1, MRD2, and Radial MPLD values measured by an ophthalmologist in the test facial image were set as correct answers, and the values estimated by the system for estimating eye-related variables were compared, and the Pearson correlation coefficient and MAPE values were confirmed.

Specifically, the test facial image had a sticker with a diameter of 5 mm attached to the subject's forehead, and the ophthalmologist measured the MRD1, MRD2, and/or Radial MPLD values on the test facial image using the information that the sticker's diameter was 5 mm.

As a result, the Pearson correlation coefficient and MAPE values for each of the MRD1, MRD2, and Radial MPLD values are shown in the table below.

|  | Radial MPLD | MRD1 | MRD2 |
| --- | --- | --- | --- |
| Correlation | 0.9756 | 0.9826 | 0.9450 |
| MAPE | 0.0593 | 0.0649 | 0.0408 |

Through the above experimental results, it is confirmed that when the system estimates the Radial MPLD, MRD1, and MRD2 values, the Pearson correlation coefficient is 0.9756, 0.9826, 0.9450, and 0.9174, respectively, achieving the evaluation criterion of 0.9 or higher. Also, it is confirmed that the MAPE was 0.0593, 0.0649, 0.0408, and 0.0684, respectively, achieving the evaluation criterion of 0.1 or lower.

Through the above experimental results, it is confirmed that when the system according to the disclosure of this application is used, it is possible to estimate highly accurate MRD1, MRD2, and/or Radial MPLD values only with a facial image captured such that the patient's eyes are included without the patient having to attach a separate marker, such as a sticker, whose actual size is known in advance.

The methods according to the exemplary embodiments described above may be implemented in the form of program instructions executable through various computer means, and be recorded in a computer-readable media. The computer-readable media may include program instructions, data files, data structures, and the like alone or in combination. The program instructions recorded on the media may be designed and configured specifically for the exemplary embodiments or may be publicly known and available to those skilled in the art regarding computer software. Examples of the computer-readable recording media include a magnetic medium such as a hard disk, a floppy disk, and a magnetic tape, an optical medium such as a CD-ROM, a DVD, a magneto-optical medium such as a floptical disk, and a hardware device specially configured to store and perform program instructions, the hardware device including a read-only memory (ROM), a random access memory (RAM), a flash memory, etc. That is, the computer-readable recording media may include a non-transitory recording medium. Examples of the computer instructions include not only machine language code generated by a compiler, but also high-level language code executable by a computer using an interpreter or the like. The hardware device described above may be configured to operate by one or more software modules to perform the actions of the exemplary embodiments, and vice versa.

The present disclosure described above is capable of various substitutions, modifications, and changes without departing from a scope of the technical idea of the present disclosure for those skilled in the art to which the present disclosure pertains. Therefore, the present disclosure is not limited by the above-described exemplary embodiments and attached drawings. In addition, the exemplary embodiments described in the present document are not intended to be limited in application, but all or part of each of the exemplary embodiments may also be selectively combined and configured so that various modifications may be made. Furthermore, the steps constituting each exemplary embodiment may be used individually or in combination with the steps constituting other exemplary embodiments.

The invention claimed is:

1. A method for estimating MRD1 (Margin Reflex Distance 1) value of a subject, performed by one or more processors, comprising:
receiving, by a communication unit, a frontal facial image in which at least a portion of an eyeball and an eyelid of one eye of the subject are all represented, wherein the frontal facial image comprises a plurality of pixels, each pixel of the plurality of pixels comprises at least one of pixel values, wherein the pixel values are not depth value which indicates calculated distance information;
identifying a boundary between the eyeball of the one eye of the subject and the eyelid of the one eye of the subject, wherein the boundary comprises a first boundary between the eyeball of the one eye of the subject and an upper eyelid of the one eye of the subject;
identifying a cornea area of the one eye of the subject using the frontal facial image, wherein the cornea area comprises an iris and a pupil of the one eye of the subject;
identifying a central point of the cornea area of the one eye of the subject;
obtaining a pixel distance value of MRD1, wherein the pixel distance value of MRD1 is a pixel distance from the central point of the cornea area to the first boundary along a vertical axis of the frontal facial image;
obtaining a pixel distance value of a radius of the cornea area;
selecting a reference distance value corresponding to the subject from among a plurality of pre-stored values based on at least one of the subject's gender, race and age, wherein the reference distance value is related to the radius of the cornea area; and
estimating a MRD1 value of the one eye based on the pixel distance value of MRD1, the pixel distance value of the radius of the cornea area and the reference distance value.

2. The method of claim 1, wherein the method further comprises adjusting an orientation of the frontal facial image.

3. The method of claim 2, wherein the frontal facial image represents both eyes of the subject,
wherein the adjusting the orientation of the frontal facial image comprises:
identifying a second cornea area of the other eye of the subject;
identifying a second central point of the second cornea area of the other eye of the subject; and
adjusting the orientation of the frontal facial image so that a straight line connecting the central point of the cornea area of the one eye of the subject and the second central point of the second cornea area of the other eye of the subject becomes horizontal.

4. The method of claim 1, wherein the boundary between the eyeball of the one eye of the subject and the eyelid of the one eye of the subject, the cornea area of the one eye of the subject and the central point of the cornea area of the one eye of the subject are identified using a pre-trained segmentation model and the frontal facial image.

5. The method of claim 1, wherein the frontal facial image further represents a second eyeball and a second eyelid of the other eye of the subject, and
wherein the method further comprises:
identifying a boundary between the second eyeball of the other eye of the subject and the second eyelid of the other eye of the subject, wherein the boundary comprises a second boundary between the second eyeball of the other eye of the subject and an upper eyelid of the other eye of the subject;
identifying a second cornea area of the other eye of the subject using the frontal facial image, wherein the second cornea area comprises an iris and a pupil of the other eye of the subject;
identifying a second central point of the second cornea area of the other eye of the subject;
obtaining a second pixel distance value of MRD1 of the other eye of the subject, wherein the second pixel distance value of MRD1 is a pixel distance from the second central point of the second cornea area to the second boundary along the vertical axis of the frontal facial image;
obtaining a second pixel distance value of a radius of the second cornea area; and
estimating a second MRD1 value of the other eye based on the second pixel distance value of MRD1, the second pixel distance value of the radius of the second cornea area and the reference distance value.

6. The method of claim 5, wherein the method further comprises:
outputting both of the MRD1 value of the one eye and the second MRD1 value of the other eye, wherein the MRD1 value indicates a MRD1 value of the one eye of the subject and the second MRD1 value indicates a MRD1 value of the other eye of the subject.

7. The method of claim 1, wherein the boundary comprises a second boundary between the eyeball of the one eye of the subject and a lower eyelid of the one eye of the subject, and
wherein the method further comprises:
obtaining a pixel distance value of MRD2 (Margin Reflex Distance 2) based on the central point of the cornea area and the boundary between the eyeball and the eyelid, wherein the pixel distance value of MRD2 is a pixel distance from the central point of the cornea area to the second boundary between the eyeball and the lower eyelid along the vertical axis of the frontal facial image; and
estimating a MRD2 value based on the pixel distance value of MRD 2, the pixel distance value of the radius of the cornea area and the reference distance value.

8. The method of claim 1, wherein the method further comprises:
obtaining a pixel distance values of Radial MPLD (Mid-Pupil Lid Distance) based on the central point of the cornea area and the boundary between the eyeball and the eyelid, wherein the pixel distance values of Radial MPLD are a set of pixel distances from the central point of the cornea area to the boundary between the eyeball and the eyelid for each unit angle; and
estimating Radial MPLD value based on the pixel distance values of Radial MPLD, the pixel distance value of the radius of the cornea area and the reference distance value.

9. A method for estimating MRD 2 (Margin Reflex Distance 2) value of a subject, performed by one or more processors, comprising:
receiving, by a communication unit, a frontal facial image in which at least a portion of an eyeball and an eyelid of one eye of the subject are all represented, wherein the frontal facial image comprises a plurality of pixels, each pixel of the plurality of pixels comprises at least one of pixel values, wherein the pixel values are not depth value which indicates calculated distance information;
identifying a boundary between the eyeball of the one eye of the subject and the eyelid of the one eye of the subject, wherein the boundary comprises a first boundary between the eyeball of the one eye of the subject and a lower eyelid of the one eye of the subject;
identifying a cornea area of the one eye of the subject using the frontal facial image, wherein the cornea area comprises an iris and a pupil of the one eye of the subject;
obtaining a pixel distance value of MRD2, wherein the pixel distance of MRD2 is a pixel distance from a central point of the cornea area to the first boundary along a vertical axis of the frontal facial image;
obtaining a pixel distance value of a radius of the cornea area;
selecting a reference distance value corresponding to the subject from among a plurality of pre-stored values based on at least one of the subject's gender, race and age, wherein the reference distance value is related to the radius of the cornea area; and
estimating a MRD2 value of the one eye based on the pixel distance value of MRD2, the pixel distance value of the radius of the cornea area and the reference distance value.

10. The method of claim 9, wherein the method further comprises adjusting an orientation of the frontal facial image.

11. The method of claim 10, wherein the frontal facial image represents both eyes of the subject,
wherein the adjusting the orientation of the frontal facial image comprises:
identifying a second cornea area of the other eye of the subject;
identifying a second central point of the second cornea area of the other eye of the subject; and
adjusting the orientation of the frontal facial image so that a straight line connecting the central point of the cornea area of the one eye of the subject and the second central point of the second cornea area of the other eye of the subject becomes horizontal.

12. The method of claim 9, wherein the boundary between the eyeball of the one eye of the subject and the eyelid of the one eye of the subject and the cornea area of the one eye of the subject and the central point of the cornea area of the one eye of the subject are identified using a pre-trained segmentation model and the frontal facial image.

13. The method of claim 9, wherein the frontal facial image further represents a second eyeball and a second eyelid of the other eye of the subject, and
wherein the method further comprises:
identifying a boundary between the second eyeball of the other eye of the subject and the second eyelid of the other eye of the subject, wherein the boundary comprises a second boundary between the second eyeball of the other eye of the subject and a lower eyelid of the other eye of the subject;
identifying a second cornea area of the other eye of the subject using the frontal facial image, wherein the second cornea area comprises an iris and a pupil of the other eye of the subject;
identifying a second central point of the second cornea area of the other eye of the subject;
obtaining a second pixel distance value of MRD2 of the other eye of the subject, wherein the second pixel distance value of MRD2 is a pixel distance from the second central point of the second cornea area to the second boundary along the vertical axis of the frontal facial image;
obtaining a second pixel distance value of a radius of the second cornea area; and
estimating a second MRD2 value of the other eye based on the second pixel distance value of MRD2, the second pixel distance value of the radius of the second cornea area and the reference distance value.

14. The method of claim 13, wherein the method further comprises:
outputting both of the MRD2 value and the second MRD2 value, wherein the MRD2 value indicates a MRD2 value of the one eye of the subject and the second MRD2 value indicates a MRD2 value of the other eye of the subject.

15. A method for estimating MPLD (Mid-Pupil Lid Distance) value of a subject, performed by one or more processors, comprising:
receiving, by a communication unit, a frontal facial image in which at least a portion of an eyeball and an eyelid of one eye of the subject are all represented, wherein the frontal facial image comprises a plurality of pixels, each pixel of the plurality of pixels comprises at least one of pixel values, wherein the pixel values are not depth value which indicates calculated distance information;
identifying a boundary between the eyeball of the one eye of the subject and the eyelid of the one eye of the subject;
identifying a cornea area of the one eye of the subject using the frontal facial image, wherein the cornea area comprises an iris and a pupil of the one eye of the subject;
identifying a central point of the cornea area of the one eye of the subject;
obtaining a pixel distance value of MPLD (Mid-Pupil Lid Distance), wherein the pixel distance value of MPLD is a pixel distance from the central point of the cornea area to the boundary along a predetermined angle direction;
obtaining a pixel distance value of a radius of the cornea area;
selecting a reference distance value corresponding to the subject from among a plurality of pre-stored values based on at least one of the subject's gender, race and age, wherein the reference distance value is related to the radius of the cornea area; and
estimating a MPLD value of the one eye based on the pixel distance value of MPLD, the pixel distance value of the radius of the cornea area and the reference distance value.

16. The method of claim 15, wherein the frontal facial image further represents a second eyeball and a second eyelid of the other eye of the subject, and wherein the method further comprises:
identifying a second boundary between the second eyeball of the other eye of the subject and the second eyelid of the other eye of the subject;
identifying a second cornea area of the other eye of the subject using the frontal facial image, wherein the second cornea area comprises an iris and a pupil of the other eye of the subject;
identifying a second central point of the second cornea area of the other eye of the subject;
obtaining a second pixel distance value of MPLD of the other eye of the subject, wherein the second pixel distance value of MPLD is a pixel distance from the second central point of the second cornea area to the second boundary along the predetermined angle direction;
obtaining a second pixel distance value of a radius of the second cornea area; and
estimating a second MPLD value of the other eye based on the second pixel distance value of MPLD, the second pixel distance value of the radius of the second cornea area and the reference distance value.

17. The method of claim 15, wherein the predetermined angle direction is corresponding to a 90-degree angle direction, and
wherein the MPLD value of the one eye is corresponding to a MRD1 (Margin Reflex Distance 1) value of the one eye.

18. The method of claim 17, wherein the boundary comprises a first boundary between the eyeball of the one eye of the subject and an upper eyelid of the one eye of the subject,
wherein the MRD1 value represents a distance value from the central point of the cornea area to a central point of the first boundary, and
wherein the 90-degree angle direction is corresponding to a direction from the central point of the cornea area to the first boundary along a vertical axis of the frontal facial image.

19. The method of claim 15, wherein the predetermined angle direction is corresponding to a 270-degree angle direction, and
wherein the MPLD value of the one eye is corresponding to a MRD2 (Margin Reflex Distance 2) Value of the one eye.

20. The method of claim 19, wherein the boundary comprises a first boundary between the eyeball of the one eye of the subject and a lower eyelid of the one eye of the subject,
wherein the MRD2 value represents a distance value from the central point of the cornea area to a central point of the first boundary, and
wherein the 270-degree angle direction is corresponding to a direction from the central point of the cornea area to the first boundary along a vertical axis of the frontal facial image.

* * * * *